US008992918B2

(12) United States Patent
Strittmatter

(10) Patent No.: US 8,992,918 B2
(45) Date of Patent: Mar. 31, 2015

(54) REACTIVATION OF AXON GROWTH AND RECOVERY IN CHRONIC SPINAL CORD INJURY

(75) Inventor: Stephen M. Strittmatter, Guilford, CT (US)

(73) Assignee: Yale University, New Haven, CT (US)

( * ) Notice: Subject to any disclaimer, the term of this patent is extended or adjusted under 35 U.S.C. 154(b) by 767 days.

(21) Appl. No.: 12/922,370

(22) PCT Filed: Mar. 13, 2009

(86) PCT No.: PCT/US2009/001635
§ 371 (c)(1),
(2), (4) Date: Jan. 6, 2011

(87) PCT Pub. No.: WO2009/114197
PCT Pub. Date: Sep. 17, 2009

(65) Prior Publication Data
US 2011/0117094 A1 May 19, 2011

Related U.S. Application Data

(60) Provisional application No. 61/069,233, filed on Mar. 13, 2008.

(51) Int. Cl.
A61K 38/00 (2006.01)
A61K 31/7088 (2006.01)
A61K 51/04 (2006.01)
C07K 14/705 (2006.01)
C07K 16/28 (2006.01)

(52) U.S. Cl.
CPC ......... A61K 31/7088 (2013.01); A61K 51/0406 (2013.01); C07K 14/705 (2013.01); C07K 16/2863 (2013.01); C07K 2319/30 (2013.01); A61K 38/00 (2013.01)
USPC .................................................... 424/134.1

(58) Field of Classification Search
CPC .............. A61K 38/00; A61K 31/7088; A61K 51/0406; C07K 2317/76; C07K 2319/30; C07K 14/705; C07K 16/2863
USPC ................. 424/134.1, 135.1, 172.1; 514/17.7
See application file for complete search history.

(56) References Cited

U.S. PATENT DOCUMENTS

| 7,119,165 B2 | 10/2006 | Strittmatter |
| 7,173,118 B2 | 2/2007 | Strittmatter et al. |
| 7,456,255 B2 | 11/2008 | Strittmatter et al. |
| 7,465,705 B2 | 12/2008 | Lee et al. |
| 7,893,032 B2 | 2/2011 | Strittmatter |
| 2002/0012965 A1 | 1/2002 | Strittmatter |
| 2003/0124704 A1 | 7/2003 | Strittmatter et al. |
| 2003/0134414 A1 | 7/2003 | Ferguson |
| 2005/0271655 A1 | 12/2005 | Lee et al. |
| 2006/0058223 A1 | 3/2006 | Mi et al. |
| 2007/0065429 A1 | 3/2007 | Lee et al. |
| 2008/0045926 A1 | 2/2008 | Relton et al. |
| 2008/0219984 A1 | 9/2008 | Strittmatter |
| 2008/0274112 A1 | 11/2008 | Lee et al. |
| 2009/0099078 A1 | 4/2009 | Lee et al. |
| 2009/0111753 A1 | 4/2009 | Strittmatter |
| 2009/0175850 A1 | 7/2009 | Strittmatter et al. |
| 2010/0278831 A1 | 11/2010 | Strittmatter |
| 2011/0129477 A1 | 6/2011 | Strittmatter et al. |
| 2012/0058125 A1 | 3/2012 | Strittmatter et al. |
| 2012/0219567 A1 | 8/2012 | Strittmatter et al. |

FOREIGN PATENT DOCUMENTS

| WO | WO 01/51520 A2 | 7/2001 |
| WO | WO 02/29059 A2 | 4/2002 |
| WO | WO 03/031462 A2 | 4/2003 |
| WO | WO 2004/093893 A2 | 11/2004 |
| WO | WO 2005/074972 A2 | 8/2005 |
| WO | WO 2006/047049 A2 | 5/2006 |
| WO | WO 2007/008732 A2 | 1/2007 |
| WO | WO 2007/089601 A2 | 8/2007 |
| WO | WO 2007/133746 A2 | 11/2007 |
| WO | WO 2008/027526 A1 | 3/2008 |

OTHER PUBLICATIONS

Basso, D.M., et al., "A Sensitive and Reliable Locomotor Rating Scale For Open Field Testing in Rats," *J. Neurotrauma* 12(1):1-21, Mary Ann Liebert, United States (1995).
Basso, D.M., et al., "MASCIS Evaluation of Open Field Locomotor Scores: Effects of Experience and Teamwork on Reliability," *J. Neurotrauma* 13(7):343-59, Mary Ann Liebert, United States (1996).
Brittis, P.A. and Flanagan, J.G., "Nogo domains and a Nogo receptor: implications for axon regeneration," *Neuron* 30(1):11-14, Cell Press, United States (2001).
Cafferty, W.B.J. and Strittmatter, S.M., "The Nogo-Nogo receptor pathway limits a spectrum of adult CNS axonal growth," *J. Neurosci.* 26(47):12242-50, Society for Neuroscience, United States (2006).
Cafferty, W.B.J., et al., Response to Correspondence: Kim et al., 'Axon Regeneration in Young Adult Mice Lacking Nogo-A/B,' *Neuron* 54(2):195-9, Cell Press, United States (2007).
Cafferty, W.B.J., et al., "Functional axonal regeneration through astrocytic scar genetically modified to digest chondroitin sulfate proteoglycans," *J. Neurosci.* 27(9):2176-85, Society for Neuroscience, United States (2007).
Chen, M.S., et al., "Nogo-A is a myelin-associated neurite outgrowth inhibitor and an antigen for monoclonal antibody IN-1," *Nature* 403(6768):434-39, Nature Publishing Group, England (2000).

(Continued)

*Primary Examiner* — Gregory S Emch
(74) *Attorney, Agent, or Firm* — Sterne, Kessler, Goldstein & Fox P.L.L.C.

(57) ABSTRACT

Disclosed are methods of treating chronic nervous system diseases or injuries, e.g., chronic spinal cord injury, using Nogo receptor antagonists, including Nogo receptor-1 (NgR1) polypeptides, Nogo receptor-1 antibodies and antigen-binding fragments thereof, soluble Nogo receptors and fusion proteins thereof, and polynucleotides. Also disclosed are methods of noninvasively monitoring axonal growth during and after treatment with an axonal growth promoting agent.

26 Claims, 5 Drawing Sheets

(56) References Cited

OTHER PUBLICATIONS

Dimou, L., et al., "Nogo-A-deficient mice reveal strain-dependent differences in axonal regeneration," *J. Neurosci.* 26(21):5591-603, Society for Neuroscience, United States (2006).

Domeniconi, M., et al., "Myelin-associated glycoprotein interacts with the Nogo66 receptor to inhibit neurite outgrowth," *Neuron* 35(2):283-90, Cell Press, United States (2002).

Fournier, A.E., et al., "Identification of a Receptor Mediating Nogo-66 Inhibition of Axonal Regeneration," *Nature* 409(6818):341-46, Nature Publishing Group, England (2001).

Fujiyoshi, K., et al., "In vivo tracing of neural tracts in the intact and injured spinal cord of marmosets by diffusion tensor tractography," *J. Neurosci.* 27(44):11991-98, Society for Neuroscience, United States (2007).

Grandpre, T., et al., "Identification of the Nogo Inhibitor of Axon Regeneration as a Reticulon Protein," *Nature* 403(6768):439-44, Nature Publishing Group, England (2000).

Grandpre, T., et al., "Nogo-66 receptor antagonist peptide promotes axonal regeneration," *Nature* 417(6888):547-51, Nature Publishing Group, England (2002).

Grimpe, B., et al., "The critical role of basement membrane-independent laminin γ1 chain during axon regeneration in the CNS," *J. Neurosci.* 22(8):3144-60, Society for Neuroscience, United States (2002).

Huang, Y., et al., "Comparative evaluation in nonhuman primates of five PET radiotracers for imaging the serotonin transporters: [$^{11}$C]McN 5652, [$^{11}$C]ADAM, [$^{11}$C]DASB, [$^{11}$C]DAPA, and [$^{11}$C]AFM," *J. Cereb. Blood Flow Metab.* 22(11):1377-98, Nature Pub. Group, United States (2002).

Huang, Y., et al., "A PET imaging agent with fast kinetics: synthesis and in vivo evaluation of the serotonin transporter ligand [$^{11}$C]2-[2-dimethylaminomethylphenylthio)]-5-fluorophenylamine ([$^{11}$C]AFA)," *Nucl. Med. Biol.* 31(6):727-38, Pergamon, United States (2004).

Huang, Y., et al., "A new positron emission tomography imaging agent for the serotonin transporter: synthesis, pharmacological characterization, and kinetic analysis of [$^{11}$C]2-[2-(dimethylaminomethyl)phenylthio]-5-fluoromethylphenylamine ([$^{11}$C]AFM), " *Nucl. Med. Biol.* 31(5):543-56, Pergamon, United States (2004).

Jones, L.L., et al., "NG2 is a major chondroitin sulfate proteoglycan produced after spinal cord injury and is expressed by macrophages and oligodendrocyte progenitors," *J. Neurosci.* 22(7):2792-803, Society for Neuroscience, United States (2002).

Kim, J.E., et al., "Nogo-66 Receptor Prevents Raphespinal and Rubrospinal Axon Regeneration and Limits Functional Recovery From Spinal Cord Injury," *Neuron* 44(3):439-51, Cell Press, United States (2004).

Kim, J.E., et al., "Axon regeneration in young adult mice lacking Nogo-A/B, " *Neuron* 38(2):187-99, Cell Press, United States (2003).

Lee, J.K., et al., "Nogo receptor antagonism promotes stroke recovery by enhancing axonal plasticity," *J. Neurosci.* 24(27):6209-17, Society for Nueroscience, United States (2004).

Li, S. and Strittmatter, S.M., "Delayed systemic Nogo-66 receptor antagonist promotes recovery from spinal cord injury," *J. Neurosci.* 23(10):4219-27, Society for Neuroscience, United States (2003).

Li, S., et al., "Blockade of Nogo-66, myelin-associated glycoprotein, and oligodendrocyte myelin glycoprotein by soluble Nogo-66 receptor promotes axonal sprouting and recovery after spinal injury," *J. Neurosci.* 24(46):10511-20, Society for Neuroscience, United States (2004).

Li, S., et al. "Transgenic inhibition of Nogo-66 receptor function allows axonal sprouting and improved locomotion after spinal injury," *Mol. Cell. Neurosci.* 29(1):26-39, Academic Press, United States (2005).

Liu, B.P., et al., "Myelin-associated glycoprotein as a functional ligand for the Nogo-66 receptor," *Science* 297(5584):1190-93, American Association for the Advancement of Science, United States (2002).

Liu, B.P., et al., "Extracellular Regulators of Axonal Growth in the Adult Central Nervous System," *Philos. Trans. R. Soc. B.* 361(1473):1593-610, England (2006).

McKerracher, L., et al., "Identification of myelin-associated glycoprotein as a major myelin-derived inhibitor of neurite growth," *Neuron* 13(4):805-11, Cell Press, United States (1994).

Mikol, D.D. and Stefansson, K., "A phosphatidylinositol-linked peanut agglutinin-binding glycoprotein in central nervous system myelin and on oligodendrocytes," *J. Cell Biol.* 106(4):1273-79, Rockefeller University Press, United States (1988).

Mukhopadhyay, G., et al., "A novel role for myelin-associated glycoprotein as an inhibitor of axonal regeneration," *Neuron* 13(3):757-67, Cell Press, United States (1994).

Park, J.H., et al., "Alzheimer precursor protein interaction with the Nogo-66 receptor reduces amyloid-beta plaque deposition," *J. Neurosci.* 26(5):1386-95, Society for Neuroscience, United States (2006).

Rossignol, S., et al., "Spinal Cord Injury: Time to Move?" *J. Neurosci.* 27(44):11782-11792, Society for Neuroscience, United States (2007).

Wang, K.C., et al., "Oligodentrocyte-myelin glycoprotein is a Nogo receptor ligand that inhibits neurite outgrowth," *Nature* 417(6892):941-77, Nature Publishing Group, England (2002).

Wang, X., et al., "Delayed Nogo receptor therapy improves recovery from spinal cord contusion," *Ann. Neurol.* 60(5):540-49, Wiley-Liss, United States (2006).

Young, W., "Spinal cord contusion models," *Prog. Brain Res.* 137:231-55, Elsevier, Netherlands (2002).

International Search Report dated Sep. 16, 2009 for International Application No. PCT/US09/01635, International Searching Authority, United States.

Written Opinion dated Sep. 16, 2009 for International Application No. PCT/US09/01635, International Searching Authority, United States.

International Preliminary Report on Patentability dated Sep. 14, 2010 for International Application No. PCT/US2009/001635, The International Bureau of WIPO, Switzerland.

Fawcett, J.W., et al., "Guidelines for the conduct of clinical trials for spinal cord injury as develolped by the ICCP panel: spontaneous recovery after spinal cord injury and statistical power needed for therapeutic clinical trials," *Spinal Cord* 45:190-205, International Spinal Cord Society, England (2007).

Fu, Q., et al., "Nonsteroid Anti-Inflammatory Drugs Promote Axon Regeneration via RhoA Inhibition, " *The Journal of Neuroscience* 27(15):4154-4164, Society for Neuroscience, United States (2007).

Zhou, Y., et al., "Nonsteroidal Anti-Inflammatory Drugs Can Lower Amyloidogenic $A\beta_{42}$ Inhibiting Rho," *Science* 302:1215-1217, American Association for the Advancement of Science, United States (2003).

National Spinal Cord Injury Statistical Center, "Spinal Cord Injury Facts and Figures at a Glance," The University of Alabama at Birmingham, United States (2006).

Chivatakarn, O., et al., "The Nogo-66 receptor NgR1 is required only for the acute growth cone-collapsing but not the chronic growth-inhibitory actions of myelin inhibitors," *J. Neurosci.* 27(27):7117-7124, Society for Neuroscience, United States (2007).

Steward, O., et al., "A re-assessment of the effects of Nogo-66 receptor antagonist on regenerative growth of axons and locomotor recovery after spinal cord injury in mice," *Exp. Neurol.* 209(2):446-468, Elsevier, Netherlands (2008).

SEQUENCE LISTING

```
<160> NUMBER OF SEQ ID NOS: 31

<210> SEQ ID NO 1
<211> LENGTH: 15
<212> TYPE: PRT
<213> ORGANISM: Artificial Sequence
<220> FEATURE:
<223> OTHER INFORMATION: Synthetic linker

<400> SEQUENCE: 1

Gly Gly Gly Gly Ser Gly Gly Gly Ser Gly Gly Gly Gly Ser
1               5                   10                  15

<210> SEQ ID NO 2
<211> LENGTH: 10
<212> TYPE: PRT
<213> ORGANISM: Artificial Sequence
<220> FEATURE:
<223> OTHER INFORMATION: Synthetic linker

<400> SEQUENCE: 2

Gly Gly Gly Gly Ser Gly Gly Gly Gly Ser
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic linker

<400> SEQUENCE: 3

Glu Ser Gly Arg Ser Gly Gly Gly Ser Gly Gly Gly Gly Ser
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Synthetic linker

<400> SEQUENCE: 4

Glu Gly Lys Ser Ser Gly Ser Gly Ser Glu Ser Lys Ser Thr
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic linker
```

```
<400> SEQUENCE: 5

Glu Gly Lys Ser Ser Gly Ser Gly Ser Glu Ser Lys Ser Thr Gln
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Synthetic linker

<400> SEQUENCE: 6

Glu Gly Lys Ser Ser Gly Ser Gly Ser Glu Ser Lys Val Asp
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic linker

<400> SEQUENCE: 7

Gly Ser Thr Ser Gly Ser Gly Lys Ser Ser Glu Gly Lys Gly
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Synthetic linker

<400> SEQUENCE: 8

Lys Glu Ser Gly Ser Val Ser Ser Glu Gln Leu Ala Gln Phe Arg Ser
1               5                   10                  15

Leu Asp

<210> SEQ ID NO 9
<211> LENGTH: 16
<212> TYPE: PRT
<213> ORGANISM: Artificial Sequence
<220> FEATURE:
<223> OTHER INFORMATION: Synthetic linker

<400> SEQUENCE: 9

Glu Ser Gly Ser Val Ser Ser Glu Glu Leu Ala Phe Arg Ser Leu Asp
1               5                   10                  15

<210> SEQ ID NO 10
<211> LENGTH: 473
<212> TYPE: PRT
<213> ORGANISM: Homo sapiens

<400> SEQUENCE: 10

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
                20                  25                  30

Cys Tyr Asn Glu Pro Lys Val Thr Thr Ser Cys Pro Gln Gln Gly Leu
            35                  40                  45

Gln Ala Val Pro Val Gly Ile Pro Ala Ala Ser Gln Arg Ile Phe Leu
        50                  55                  60
```

-continued

```
His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                 85                  90                  95

Asp Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
            115                 120                 125

Leu Gly Arg Leu His Thr Leu His Leu Asp Arg Cys Gly Leu Gln Glu
        130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Arg His Ile Asn Asp Ser Pro Phe
370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
            450                 455                 460

Val Leu Trp Thr Val Leu Gly Pro Cys
465                 470
```

<210> SEQ ID NO 11
<211> LENGTH: 473
<212> TYPE: PRT
<213> ORGANISM: Rattus

<400> SEQUENCE: 11

| Met | Lys | Arg | Ala | Ser | Ser | Gly | Gly | Ser | Arg | Leu | Leu | Ala | Trp | Val | Leu |
|---|---|---|---|---|---|---|---|---|---|---|---|---|---|---|---|
| 1 | | | | 5 | | | | | 10 | | | | | 15 | |

Trp Leu Gln Ala Trp Arg Val Ala Thr Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Thr Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Asn
        275                 280                 285

Leu Pro Gln Arg Leu Ala Gly Arg Asp Leu Lys Arg Leu Ala Ala Ser
    290                 295                 300

Asp Leu Glu Gly Cys Ala Val Ala Ser Gly Pro Phe Arg Pro Phe Gln
305                 310                 315                 320

Thr Asn Gln Leu Thr Asp Glu Glu Leu Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
    370                 375                 380

-continued

```
Gly Thr Leu Pro Gly Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg Arg
                405                 410                 415

Pro Gly Cys Ser Arg Lys Asn Arg Thr Arg Ser His Cys Arg Leu Gly
                420                 425                 430

Gln Ala Gly Ser Gly Ser Ser Gly Thr Gly Asp Ala Glu Gly Ser Gly
                435                 440                 445

Ala Leu Pro Ala Leu Ala Cys Ser Leu Ala Pro Leu Gly Leu Ala Leu
            450                 455                 460

Val Leu Trp Thr Val Leu Gly Pro Cys
465                 470

<210> SEQ ID NO 12
<211> LENGTH: 473
<212> TYPE: PRT
<213> ORGANISM: Mus

<400> SEQUENCE: 12

Met Lys Arg Ala Ser Ser Gly Gly Ser Arg Leu Leu Ala Trp Val Leu
1               5                   10                  15

Trp Leu Gln Ala Trp Arg Val Ala Thr Pro Cys Pro Gly Ala Cys Val
                20                  25                  30

Cys Tyr Asn Glu Pro Lys Val Thr Thr Ser Cys Pro Gln Gln Gly Leu
            35                  40                  45

Gln Ala Val Pro Thr Gly Ile Pro Ala Ser Ser Gln Arg Ile Phe Leu
        50                  55                  60

His Gly Asn Arg Ile Ser His Val Pro Ala Ala Ser Phe Gln Ser Cys
65              70                  75                  80

Arg Asn Leu Thr Ile Leu Trp Leu His Ser Asn Ala Leu Ala Arg Ile
                85                  90                  95

Asp Ala Ala Ala Phe Thr Gly Leu Thr Leu Leu Glu Gln Leu Asp Leu
            100                 105                 110

Ser Asp Asn Ala Gln Leu His Val Val Asp Pro Thr Thr Phe His Gly
        115                 120                 125

Leu Gly His Leu His Thr Leu His Leu Asp Arg Cys Gly Leu Arg Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Met Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Asn
        275                 280                 285
```

```
Leu Pro Gln Arg Leu Ala Asp Arg Asp Leu Lys Arg Leu Ala Ala Ser
        290                 295                 300

Asp Leu Glu Gly Cys Ala Val Ala Ser Gly Pro Phe Arg Pro Ile Gln
305                 310                 315                 320

Thr Ser Gln Leu Thr Asp Glu Glu Leu Leu Ser Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
    370                 375                 380

Gly Thr Leu Pro Ser Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Ala Ser Gly Thr Gly Asp Ala Glu Gly Ser Gly
        435                 440                 445

Ala Leu Pro Ala Leu Ala Cys Ser Leu Ala Pro Leu Gly Leu Ala Leu
    450                 455                 460

Val Leu Trp Thr Val Leu Gly Pro Cys
465                 470

<210> SEQ ID NO 13
<211> LENGTH: 344
<212> TYPE: PRT
<213> ORGANISM: Homo sapiens

<400> SEQUENCE: 13

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
```

```
            180                 185                 190
Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala
            340

<210> SEQ ID NO 14
<211> LENGTH: 310
<212> TYPE: PRT
<213> ORGANISM: Homo sapiens

<400> SEQUENCE: 14

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205
```

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
                260                 265                 270

Ala Trp Leu Gln Lys Phe Arg Gly Ser Ser Glu Val Pro Cys Ser
                275                 280                 285

Leu Pro Gln Arg Leu Ala Gly Arg Asp Leu Lys Arg Leu Ala Ala Asn
290                 295                 300

Asp Leu Gln Gly Cys Ala
305                 310

<210> SEQ ID NO 15
<211> LENGTH: 344
<212> TYPE: PRT
<213> ORGANISM: Rattus

<400> SEQUENCE: 15

Met Lys Arg Ala Ser Ser Gly Gly Ser Arg Leu Pro Thr Trp Val Leu
1               5                   10                  15

Trp Leu Gln Ala Trp Arg Val Ala Thr Pro Cys Pro Gly Ala Cys Val
                20                  25                  30

Cys Tyr Asn Glu Pro Lys Val Thr Thr Ser Arg Pro Gln Gln Gly Leu
                35                  40                  45

Gln Ala Val Pro Ala Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
                100                 105                 110

Ser Asp Asn Ala Gln Leu Arg Val Val Asp Pro Thr Thr Phe Arg Gly
            115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
                260                 265                 270

Ala Trp Leu Gln Lys Phe Arg Gly Ser Ser Ser Gly Val Pro Ser Asn
        275                 280                 285

Leu Pro Gln Arg Leu Ala Gly Arg Asp Leu Lys Arg Leu Ala Thr Ser
290                 295                 300

Asp Leu Glu Gly Cys Ala Val Ala Ser Gly Pro Phe Arg Pro Phe Gln
305                 310                 315                 320

Thr Asn Gln Leu Thr Asp Glu Glu Leu Leu Gly Leu Pro Lys Cys Cys
            325                 330                 335

Gln Pro Asp Ala Ala Asp Lys Ala
            340

<210> SEQ ID NO 16
<211> LENGTH: 310
<212> TYPE: PRT
<213> ORGANISM: Rattus

<400> SEQUENCE: 16

Met Lys Arg Ala Ser Ser Gly Gly Ser Arg Leu Pro Thr Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Arg Pro Gln Gln Gly Leu
        35                  40                  45

Gln Ala Val Pro Ala Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Gly Val Pro Ser Asn
        275                 280                 285

Leu Pro Gln Arg Leu Ala Gly Arg Asp Leu Lys Arg Leu Ala Thr Ser

Asp Leu Glu Gly Cys Ala
305                310

<210> SEQ ID NO 17
<211> LENGTH: 310
<212> TYPE: PRT
<213> ORGANISM: Homo sapiens
<220> FEATURE:
<223> OTHER INFORMATION: Human NgR1 mutant

<400> SEQUENCE: 17

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Ala Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Ala Ala
305                 310

<210> SEQ ID NO 18
<211> LENGTH: 310
<212> TYPE: PRT

<213> ORGANISM: Rattus
<220> FEATURE:
<223> OTHER INFORMATION: Rat NgR1 mutant

<400> SEQUENCE: 18

```
Met Lys Arg Ala Ser Ser Gly Gly Ser Arg Leu Pro Thr Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Arg Pro Gln Gln Gly Leu
        35                  40                  45

Gln Ala Val Pro Ala Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Ala Arg Ala Arg Pro Leu Trp
            260                 265                 270

Ala Trp Leu Gln Lys Phe Arg Gly Ser Ser Ser Gly Val Pro Ser Asn
        275                 280                 285

Leu Pro Gln Arg Leu Ala Gly Arg Asp Leu Lys Arg Leu Ala Thr Ser
    290                 295                 300

Asp Leu Glu Gly Ala Ala
305                 310
```

<210> SEQ ID NO 19
<211> LENGTH: 344
<212> TYPE: PRT
<213> ORGANISM: Homo sapiens
<220> FEATURE:
<223> OTHER INFORMATION: Human NgR1 mutant

<400> SEQUENCE: 19

```
Met Lys Arg Ala Ser Ala Gly Gly Ser Arg Leu Leu Ala Trp Val Leu
1               5                   10                  15
```

```
Trp Leu Gln Ala Trp Gln Val Ala Ala Pro Cys Pro Gly Ala Cys Val
                20                  25                  30

Cys Tyr Asn Glu Pro Lys Val Thr Thr Ser Cys Pro Gln Gln Gly Leu
             35                  40                  45

Gln Ala Val Pro Val Gly Ile Pro Ala Ala Ser Gln Arg Ile Phe Leu
         50                  55                  60

His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                 85                  90                  95

Asp Ala Ala Phe Thr Gly Leu Ala Leu Leu Glu Gln Leu Asp Leu
                100                 105                 110

Ser Asp Asn Ala Gln Leu Arg Ser Val Asp Pro Ala Thr Phe His Gly
            115                 120                 125

Leu Gly Arg Leu His Thr Leu His Leu Asp Arg Cys Gly Leu Gln Glu
        130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Ala Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
290                 295                 300

Asp Leu Gln Gly Ala Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala
            340

<210> SEQ ID NO 20
<211> LENGTH: 8
<212> TYPE: PRT
<213> ORGANISM: Artificial Sequence
<220> FEATURE:
<223> OTHER INFORMATION: Synthetic epitope

<400> SEQUENCE: 20

Asp Tyr Lys Asp Asp Asp Asp Lys
1               5

<210> SEQ ID NO 21
<211> LENGTH: 8
```

```
<212> TYPE: PRT
<213> ORGANISM: Artificial Sequence
<220> FEATURE:
<223> OTHER INFORMATION: Synthetic epitope

<400> SEQUENCE: 21

Asp Tyr Lys Asp Glu Asp Asp Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic epitope

<400> SEQUENCE: 22

Ala Trp Arg His Pro Gln Phe Gly Gly
1               5

<210> SEQ ID NO 23
<211> LENGTH: 11
<212> TYPE: PRT
<213> ORGANISM: Artificial Sequence
<220> FEATURE:
<223> OTHER INFORMATION: Synthetic epitope

<400> SEQUENCE: 23

Tyr Thr Asp Ile Glu Met Asn Arg Leu Gly Lys
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Synthetic epitope

<400> SEQUENCE: 24

His His His His His His
1               5

<210> SEQ ID NO 25
<211> LENGTH: 13
<212> TYPE: PRT
<213> ORGANISM: Influenza virus

<400> SEQUENCE: 25

Tyr Pro Tyr Asp Val Pro Asp Tyr Ala Ile Glu Gly Arg
1               5                   10

<210> SEQ ID NO 26
<211> LENGTH: 11
<212> TYPE: PRT
<213> ORGANISM: Homo sapiens

<400> SEQUENCE: 26

Glu Gln Lys Leu Leu Ser Glu Glu Asp Leu Asn
1               5                   10

<210> SEQ ID NO 27
<211> LENGTH: 1719
<212> TYPE: DNA
<213> ORGANISM: Homo sapiens

<400> SEQUENCE: 27
```

| | |
|---|---|
| agcccagcca gagccgggcg gagcggagcg cgccgagcct cgtcccgcgg ccgggccggg | 60 |
| gccgggccgt agcggcggcg cctggatgcg gacccggccg cggggagacg ggcgcccgcc | 120 |
| ccgaaacgac tttcagtccc cgacgcgccc cgcccaaccc ctacgatgaa gagggcgtcc | 180 |
| gctggaggga gccggctgct ggcatgggtg ctgtggctgc aggcctggca ggtggcagcc | 240 |
| ccatgcccag gtgcctgcgt atgctacaat gagcccaagg tgacgacaag ctgccccccag | 300 |
| cagggcctgc aggctgtgcc cgtgggcatc cctgctgcca gccagcgcat cttcctgcac | 360 |
| ggcaaccgca tctcgcatgt gccagctgcc agcttccgtg cctgccgcaa cctcaccatc | 420 |
| ctgtggctgc actcgaatgt gctggcccga attgatgcgg ctgccttcac tggcctggcc | 480 |
| ctcctggagc agctggacct cagcgataat gcacagctcc ggtctgtgga ccctgccaca | 540 |
| ttccacggcc tgggccgcct acacacgctg cacctggacc gctgcggcct gcaggagctg | 600 |
| ggcccggggc tgttccgcgg cctggctgcc ctgcagtacc tctacctgca ggacaacgcg | 660 |
| ctgcaggcac tgcctgatga caccttccgc gacctgggca acctcacaca cctcttcctg | 720 |
| cacggcaacc gcatctccag cgtgcccgag cgcgccttcc gtgggctgca cagcctcgac | 780 |
| cgtctcctac tgcaccagaa ccgcgtggcc catgtgcacc cgcatgcctt ccgtgacctt | 840 |
| ggccgcctca tgacactcta tctgtttgcc aacaatctat cagcgctgcc cactgaggcc | 900 |
| ctggcccccc tgcgtgccct gcagtacctg aggctcaacg acaaccctg ggtgtgtgac | 960 |
| tgccgggcac gcccactctg ggcctggctg cagaagttcc gcggctcctc ctccgaggtg | 1020 |
| ccctgcagcc tcccgcaacg cctggctggc cgtgacctca acgcctagc tgccaatgac | 1080 |
| ctgcagggct cgcgctgtggc caccggccct taccatccca tctggaccgg cagggccacc | 1140 |
| gatgaggagc cgctggggct tcccaagtgc tgccagccag atgccgctga caaggcctca | 1200 |
| gtactggagc ctggaagacc agcttcggca ggcaatgcgc tgaagggacg cgtgccgccc | 1260 |
| ggtgacagcc cgccgggcaa cggctctggc ccacggcaca tcaatgactc acccctttggg | 1320 |
| actctgcctg gctctgctga gccccgctc actgcagtgc ggcccgaggg ctccgagcca | 1380 |
| ccagggttcc ccacctcggg ccctcgccgg aggccaggct gttcacgcaa gaaccgcacc | 1440 |
| cgcagccact gccgtctggg ccaggcaggc agcggggtg gcgggactgg tgactcagaa | 1500 |
| ggctcaggtg ccctacccag cctcacctgc agcctcaccc cctgggcct ggcgctggtg | 1560 |
| ctgtggacag tgcttgggcc ctgctgaccc ccagcggaca caagagcgtg ctcagcagcc | 1620 |
| aggtgtgtgt acatacgggg tctctctcca cgccgccaag ccagccgggc ggccgacccg | 1680 |
| tggggcaggc caggccaggt cctccctgat ggacgcctg | 1719 |

<210> SEQ ID NO 28
<211> LENGTH: 1422
<212> TYPE: DNA
<213> ORGANISM: Rattus norvegicus

<400> SEQUENCE: 28

| | |
|---|---|
| atgaagaggg cgtcctccgg aggaagccgg ctgccgacat gggtgttatg gctacaggcc | 60 |
| tggagggtag caacgccctg ccctggtgcc tgtgtgtgct acaatgagcc caaggtcaca | 120 |
| acaagccgcc cccagcaggg cctgcaggct gtacccgctg gcatcccagc ctccagccag | 180 |
| agaatcttcc tgcacggcaa ccgaatctct acgtgccag ccgccagctt ccagtcatgc | 240 |
| cggaatctca ccatcctgtg gctgcactca aatgcgctgg ccgggattga tgccgcggcc | 300 |
| ttcactggtc tgaccctcct ggagcaacta gatcttagtg acaatgcaca gctccgtgtc | 360 |
| gtggacccca ccacgttccg tggcctgggc cacctgcaca cgctgcacct agaccgatgc | 420 |

```
ggcctgcagg agctggggcc tggcctattc cgtgggctgg cagctctgca gtacctctac    480
ctacaagaca caacctgca ggcacttccc gacaacacct tccgagacct gggcaacctc    540
acgcatctct ttctgcatgg caaccgtatc cccagtgttc ctgagcacgc tttccgtggc    600
ttgcacagtc ttgaccgtct cctcttgcac agaaccatg tggctcgtgt gcacccacat    660
gccttccggg accttggccg actcatgacc ctctacctgt tgccaacaa cctctccatg    720 ctccccgcag aggtcctagt gccctgagg tctctgcagt acctgcgact caatgacaac    780
ccctgggtgt gtgactgcag ggcacgtccg ctctgggcct ggctgcagaa gttccgaggt    840
tcctcatccg gggtgcccag caacctaccc aacgcctgg caggccgtga tctgaagcgc    900
ctggctacca gtgacttaga ggggttgtgct gtggcttcgg ggcccttccg tcccttccag    960
accaatcagc tcactgatga ggagctgctg ggcctcccca gtgctgcca gccggatgct   1020 gcagacaagg cctcagtact ggaacccggg aggccggcgt ctgttggaaa tgcactcaag   1080
ggacgtgtgc ctcccggtga cactccacca ggcaatggct caggcccacg gcacatcaat   1140
gactctccat ttgggacttt gcccggctct gcagagcccc cactgactgc cctgcggcct   1200
gggggttccg agcccccggg actgcccacc acgggccccc gcaggaggcc aggttgttcc   1260
agaaagaacc gcacccgtag ccactgccgt ctgggccagg caggaagtgg gagcagtgga   1320
actggggatg cagaaggttc gggggccctg cctgccctgg cctgcagcct tgctcctctg   1380
ggccttgcac tggtactttg gacagtgctt gggccctgct ga                      1422
```

<210> SEQ ID NO 29
<211> LENGTH: 1892
<212> TYPE: DNA
<213> ORGANISM: Mus musculus

<400> SEQUENCE: 29

```
agccgcagcc cgcgagccca gcccggcccg gtagagcgga gcgccggagc ctcgtcccgc     60
ggccgggccg ggaccgggcc ggagcagcgg cgcctggatg cggacccggc cgcgcgcaga    120
cgggcgcccg ccccgaagcc gcttccagtg cccgacgcgc cccgctcgac cccgaagatg    180
aagagggcgt cctccggagg aagcaggctg ctggcatggg tgttatggct acaggcctgg    240
agggtagcaa caccatgccc tggtgcttgt gtgtgctaca atgagcccaa ggtaacaaca    300
agctgccccc agcagggtct gcaggctgtg cccactggca tcccagcctc tagccagcga    360
atcttcctgc atggcaaccg aatctctcac gtgccagctg cgagcttcca gtcatgccga    420
aatctcacta tcctgtggct gcactctaat gcgctggctc ggatcgatgc tgctgccttc    480
actggtctga ccctcctgga gcaactagat cttagtgata atgcacagct tcatgtcgtg    540 gacctacca cgttcacgg cctgggccac ctgcacacac tgcacctaga ccgatgtggc    600
ctgcgggagc tgggtcccgg cctattccgt ggactagcag ctctgcagta cctctaccta    660
caagacaaca atctgcaggc actccctgac aacacctttc gagacctggg caacctcacg    720
catctctttc tgcatggcaa ccgtatcccc agtgtgcctg agcacgcttt ccgtggcctg    780
cacagtcttg accgcctcct cttgcaccag aaccatgtgg ctcgtgtgca cccacatgcc    840
ttccgggacc ttggccgcct catgaccctc tacctgtttg ccaacaacct ctccatgctg    900
cctgcagagg tcctaatgcc cctgaggtct ctgcagtacc tgcgactcaa tgacaacccc    960
tgggtgtgtg actgccgggc acgtccactc tgggcctggc tgcagaagtt ccgaggttcc   1020
tcatcagagg tgccctgcaa cctgccccaa cgcctggcag accgtgatct taagcgcctc   1080
```

```
gctgccagtg acctagaggg ctgtgctgtg gcttcaggac ccttccgtcc catccagacc    1140
agtcagctca ctgatgagga gctgctgagc ctccccaagt gctgccagcc agatgctgca    1200
gacaaagcct cagtactgga acccgggagg ccagcttctg ccggaaacgc cctcaaggga    1260
cgtgtgcctc ccggtgacac tccaccaggc aatggctcag ccctcggca catcaatgac     1320 tctccatttg gaactttgcc cagctctgca gagcccccac tgactgccct gcggcctggg    1380
ggttccgagc caccaggact tcccaccact ggtccccgca ggaggccagg ttgttcccgg    1440
aagaatcgca cccgcagcca ctgccgtctg ggccaggcgg gaagtggggc cagtggaaca    1500
ggggacgcag agggttcagg ggctctgcct gctctggcct gcagccttgc tcctctgggc    1560
cttgcactgg tactttggac agtgcttggg ccctgctgac cagccaccag ccaccaggtg    1620
tgtgtacata tggggtctcc ctccacgccg ccagccagag ccaggacag gctctgaggg      1680 gcaggccagg ccctccctga cagatgcctc cccaccagcc cacccccatc tccacccat     1740 catgtttaca gggttccggg ggtggcgttt gttccagaac gccacctccc acccggatcg    1800
cggtatatag agatatgaat tttattttac ttgtgtaaaa tatcggatga cgtggaataa    1860
agagctcttt tcttaaaaaa aaaaaaaaaa aa                                  1892
```

<210> SEQ ID NO 30
<211> LENGTH: 200
<212> TYPE: DNA
<213> ORGANISM: Artificial Sequence
<220> FEATURE:
<223> OTHER INFORMATION: Synthetic general structure for an
      oligonucleotide used in preparation of siRNA molecule
<220> FEATURE:
<221> NAME/KEY: misc_feature
<222> LOCATION: (1)..(200)
<223> OTHER INFORMATION: n is a, g, c, t, or u
<220> FEATURE:
<221> NAME/KEY: misc_feature
<222> LOCATION: (2)..(200)
<223> OTHER INFORMATION: nucleotide may be missing

<400> SEQUENCE: 30

```
nnnnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn                                                200
```

<210> SEQ ID NO 31
<211> LENGTH: 200
<212> TYPE: DNA
<213> ORGANISM: Artificial Sequence
<220> FEATURE:
<223> OTHER INFORMATION: Synthetic general structure for an
      oligonucleotide used in preparation of siRNA molecule
<220> FEATURE:
<221> NAME/KEY: misc_feature
<222> LOCATION: (1)..(200)
<223> OTHER INFORMATION: n is a, g, c, t, or u
<220> FEATURE:
<221> NAME/KEY: misc_feature
<222> LOCATION: (2)..(200)
<223> OTHER INFORMATION: nucleotide may be missing

<400> SEQUENCE: 31

```
nnnnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn    120
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 180 |
| nnnnnnnnnn | nnnnnnnnnn | | | | | 200 |

REACTIVATION OF AXON GROWTH AND RECOVERY IN CHRONIC SPINAL CORD INJURY

CROSS-REFERENCE TO RELATED APPLICATIONS

This application is the National Stage of International Application Number PCT/US2009/001635, filed Mar. 13, 2009, which claims the benefit of U.S. Provisional Application No. 61/069,233, filed Mar. 13, 2008, all of which are incorporated by reference herein.

REFERENCE TO A SEQUENCE LISTING SUBMITTED ELECTRONICALLY VIA EFS-WEB

The content of the electronically submitted sequence listing (Name: sequence-listing.txt, Size: 43,931 bytes; and Date of Creation: Sep. 13, 2010) is herein incorporated by reference in its entirety.

FIELD OF THE INVENTION

This invention relates to neurobiology and diseases or injuries related thereto. More particularly, this invention relates to methods of treating chronic nervous system diseases or injuries, e.g., chronic spinal cord injury, using Nogo-receptor antagonists, including Nogo receptor-1 (NgR1) polypeptides, Nogo receptor-1 antibodies and antigen-binding fragments thereof, soluble Nogo receptors and fusion proteins thereof, and polynucleotides. This invention further relates to methods of monitoring treatment of chronic nervous system diseases or injuries, e.g., chronic spinal cord injury (SCI).

BACKGROUND OF THE INVENTION

Nerve cell function is greatly influenced by the contact between the neuron and other cells in its immediate environment (U. Rutishauser, T. M. Jessell, *Physiol. Rev.* 68:819 (1988)). These cells include specialized glial cells, oligodendrocytes in the central nervous system (CNS), and Schwann cells in the peripheral nervous system (PNS), which ensheathe the neuronal axon with myelin (an insulating structure of multi-layered membranes) (G. Lemke, in *An Introduction to Molecular Neurobiology*, Z. Hall, Ed. (Sinauer, Sunderland, Mass.), p. 281 (1992)).

While CNS neurons have the capacity to regenerate after injury, they are inhibited from doing so because of the presence of inhibitory proteins present in myelin and possibly also by other types of molecules normally found in their local environment (Brittis and Flanagan, *Neuron* 30:11-14 (2001); Jones et al., *J. Neurosc.* 22:2792-2803 (2002); Grimpe et al., *J. Neurosci.* 22:3144-3160 (2002)). Thus, nervous system diseases or injuries, such as spinal cord injury (SCI), traumatic brain injury, or chronic deficits after stroke, cause profound and persistent neurological deficits. Much of the disability below the level of injury is due to the interruption of axonal connectivity.

Myelin plays a role in interrupting axonal connectivity by limiting axonal growth and neurological recovery after SCI (B. P. Liu et al., *Philos. Trans. R. Soc. Lond. B. Biol. Sci.* 361:1593-1610 (2006)). Amongst the inhibitory myelin proteins are Nogo-A (Rtn4A) (Chen et al., *Nature* 403:434-439 (2000); Grandpre et al., *Nature* 403:439-444 (2000)), myelin associated glycoprotein (MAG, Siglec-4) (McKerracher et al., *Neuron* 13:805-811 (1994); Mukhopadhyay et al., *Neuron* 13:757-767 (1994)), and oligodendrocyte myelin glycoprotein (OMgp) (Mikol and Stefansson, *J. Cell. Biol.* 106:1273-1279 (1988)).

Each of these proteins has been separately shown to be a ligand for the neuronal Nogo receptor-1 (NgR1, Rtn4R) protein expressed by axons (Wang et al., *Nature* 417:941-944 (2002); Liu et al., *Science* 297:1190-93 (2002); Grandpre et al., *Nature* 403:439-444 (2000); Chen et al., *Nature* 403:434-439 (2000); Domeniconi et al., *Neuron* 35:283-90 (2002); X. Wang et al., *Ann. Neurol.* 60:540-49 (2006)). NgR1 is a glycophosphatidylinositol (GPI)-anchored membrane protein that contains eight leucine rich repeats (Fournier et al., *Nature* 409:341-346 (2001)). Upon interaction with an inhibitory protein, e.g., NogoA, MAG and OMgp, the NgR1 complex transduces signals that lead to growth cone collapse and inhibition of neurite outgrowth.

Recent advances have identified compounds that protect neuronal elements immediately after injury and/or stimulate the growth of axons when administered within several days of SCI (S. Rossignol et al., *J. Neurosci.* 27:11782-92 (2007); B. P. Liu et al., *Philos. Trans. R. Soc. Lond. B. Biol. Sci.* 361:1593-1610 (2006)). For example, soluble NgR1(310)ecto-Fc protein infused into the CNS within a week of spinal cord dorsal hemisection, stroke, or spinal cord contusion increases axonal growth responses and improves behavioral recovery (S. Li et al., *J. Neurosci.* 24:10511-20 (2004); J. K. Lee et al., *J. Neurosci.* 24:6209-17 (2004); D. M. Basso et al., *J. Neurotrauma* 12:1-21 (1995)).

Clinical trials are now testing the efficacy of compounds that block myelin inhibitors in these instances of acute nervous system disease or injury, such as acute SCI (S. Rossignol et al., *J. Neurosci.* 27:11782-92 (2007). However, because SCI frequently occurs in young adults and improved supportive care has dramatically increased life expectancy, the prevalence of chronic SCI is more than twenty times the annual incidence of acute SCI (A. E. Fournier et al., *Nature* 409:341-46 (2001)). Neuroprotective strategies are clearly too late to benefit chronic SCI, and axonal growth promoting strategies have only shown benefit during the acute, after-injury period. Thus, therapeutic advances for acute spinal cord injuries have been considered incapable of re-activating axonal growth and recovery in the much more prevalent condition of chronic SCI. The prevailing opinion is that blockade of axonal growth inhibitors can be beneficial only in a time frame close to the trauma, when the injured axon has the highest potential for growth. This leaves cellular transplantation, but not pharmacological intervention, as the only therapeutic potential for chronic SCI.

Therefore, there exists an urgent need for therapeutic methods for treating chronic nervous system diseases or injuries, including chronic SCI, and for non-invasive methods of monitoring said treatment.

SUMMARY OF THE INVENTION

The present invention is directed to the use of Nogo receptor-1 antagonists for treating chronic SCI. The invention features methods and molecules useful for treating chronic SCI and for monitoring said treatment of chronic SCI.

In certain embodiments, the invention includes a method of treating chronic SCI in a mammal, comprising administering to a mammal in need thereof a therapeutically effective amount of a Nogo-receptor antagonist. In some embodiments, the Nogo-receptor antagonist stimulates axonal growth.

In certain embodiments, the invention includes a method of treating a mammal displaying signs or symptoms of chronic SCI, comprising administering to a mammal in need thereof a therapeutically effective amount of a Nogo-receptor antagonist to said mammal. In some embodiments, the Nogo-receptor antagonist stimulates axonal growth.

In certain embodiments, the invention includes a method for stimulating axonal growth following chronic SCI, comprising administering a therapeutically effective amount of a Nogo-receptor antagonist.

In some embodiments, the chronic SCI is a spinal contusion. In some embodiments, the mammal is a human. In one embodiment, the spinal contusion is in a human.

In some embodiments, the Nogo-receptor antagonist is administered by bolus injection, chronic infusion, or implantation of a controlled-release system. In some embodiments, the Nogo-receptor antagonist is administered directly into the central nervous system, intracerebroventricularly, intrathecally. In some embodiments, the Nogo-receptor antagonist is administered parenterally, intraventricularly, orally, by inhalation spray, topically, rectally, nasally, buccally, vaginally, or via an implanted reservoir.

In some embodiments, the therapeutically effective amount is from 0.001 mg/k to 10 mg/kg of Nogo-receptor antagonist. In some embodiments, the therapeutically effective amount is from 0.01 mg/kg to 1.0 mg/kg. In one embodiment, the therapeutically effective amount is from 0.05 mg/kg to 5 mg/kg.

In some embodiments, the Nogo-receptor antagonist is administered at a time selected from the group consisting of: (a) greater than a week after the initial injury; (b) two weeks or greater after the initial injury; (c) three weeks or greater after the initial injury; (d) four weeks or greater after the initial injury; (e) two months or greater after the initial injury; (f) three months or greater after the initial injury; (g) four months or greater after the initial injury; (h) five months or greater after the initial injury; (i) six months or greater after the initial injury; (j) seven months or greater after the initial injury; (k) eight months or greater after the initial injury; (l) nine months or greater after the initial injury; (m) ten months or greater after the initial injury; (n) eleven months or greater after the initial injury; and (o) twelve months or greater after the initial injury. In one embodiment, the Nogo-receptor antagonist is administered three months or greater after the initial injury.

In some embodiments, the Nogo-receptor antagonist is a Nogo receptor-1 polypeptide. In some embodiments, the Nogo receptor-1 polypeptide is a soluble Nogo receptor-1 polypeptide. In some embodiments, the soluble Nogo receptor-1 polypeptide is 90% identical to a reference amino acid sequence selected from the group consisting of: (a) amino acids 26 to 310 of SEQ ID NO:10 or 11; (b) amino acids 26 to 344 of SEQ ID NO:10 or 11; (c) amino acids 26 to 445 of SEQ ID NO:10 or 11; (d) amino acids 26 to 309 of SEQ ID NO:10 or 11; (e) amino acids 27 to 310 of SEQ ID NO:10 or 11; (f) amino acids 28 to 344 of SEQ ID NO:10 or 11; (g) amino acids 29 to 445 of SEQ ID NO:10 or 11; (h) amino acids 30 to 309 of SEQ ID NO:10 or 11; (i) amino acids 1 to 310 of SEQ ID NO:10 or 11; (j) amino acids 1 to 344 of SEQ ID NO:10 or 11; (k) amino acids 1 to 445 of SEQ ID NO:10 or 11; (l) amino acids 1 to 309 of SEQ ID NO:10 or 11; (m) variants or derivatives of any of said reference amino acid sequences; and (n) a combination of one or more of said reference amino acid sequences or variants or derivatives thereof.

In some embodiments, the soluble Nogo receptor-1 polypeptide is selected from the group consisting of: (a) amino acids 26 to 310 of SEQ ID NO:10 or 11; (b) amino acids 26 to 344 of SEQ ID NO:10 or 11; (c) amino acids 26 to 445 of SEQ ID NO:10 or 11; (d) amino acids 26 to 309 of SEQ ID NO:10 or 11; (e) amino acids 27 to 310 of SEQ ID NO:10 or 11; (f) amino acids 28 to 344 of SEQ ID NO:10 or 11; (g) amino acids 29 to 445 of SEQ ID NO:10 or 11; (h) amino acids 30 to 309 of SEQ ID NO:10 or 11; (i) amino acids 1 to 310 of SEQ ID NO:10 or 11; (j) amino acids 1 to 344 of SEQ ID NO:10 or 11; (k) amino acids 1 to 445 of SEQ ID NO:10 or 11; (l) amino acids 1 to 309 of SEQ ID NO:10 or 11; (m) variants or derivatives of any of said reference amino acid sequences; and (n) a combination of one or more of said reference amino acid sequences or variants or derivatives thereof.

In some embodiments, the soluble Nogo receptor-1 polypeptide comprises an amino acid sequence selected from the group consisting of: (a) amino acids 26 to 310 of human NgR1 (SEQ ID NO:14) with up to ten conservative amino acid substitutions; (b) amino acids 26 to 344 of human NgR1 (SEQ ID NO:13) with up to ten conservative amino acid substitutions; (c) amino acids 27 to 310 of rat NgR1 (SEQ ID NO:16) with up to ten conservative amino acid substitutions; and (d) amino acids 27 to 344 of rat NgR1 (SEQ ID NO:15) with up to ten conservative amino acid substitutions. In one embodiment, the soluble Nogo receptor-1 polypeptide comprises amino acids 26 to 310 of human NgR1 (SEQ ID NO:14).

In some embodiments, the soluble Nogo receptor-1 polypeptide comprises an amino acid sequence identical to a reference amino acid sequence except that at least one cysteine residue of said reference amino acid sequence is substituted with a different amino acid, wherein said reference amino acid sequence is selected from the group consisting of: (i) amino acids a to 445 of SEQ ID NO:10; (iii) amino acids 27 to b of SEQ ID NO:10; and (iii) amino acids a to b of SEQ ID NO:10, wherein a is any integer from 25 to 35, and b is any integer from 300 to 450; and wherein said polypeptide stimulates axonal growth following chronic spinal cord injury. In some embodiments, the C266 of said reference amino acid sequence is substituted with a different amino acid. In some embodiments, the C309 of said reference amino acid sequence is substituted with a different amino acid. In some embodiments, the C335 of said reference amino acid sequence is substituted with a different amino acid. In some embodiments, the C266 and C309 of said reference amino acid sequence are substituted with different amino acids. In some embodiments, the C309 and C335 of said reference amino acid sequence are substituted with different amino acids. In some embodiments, the different amino acid is alanine.

In some embodiments, the Nogo receptor-1 polypeptide further comprises a non-NgR1 moiety. In some embodiments, the non-NgR1 moiety is a heterologous polypeptide fused to said Nogo receptor-1 polypeptide. In some embodiments, the heterologous polypeptide is selected from the group consisting of (a) serum albumin; (b) an Fc region; (c) a signal peptide; (d) a polypeptide tag; and (e) a combination of two or more of said heterologous polypeptides. In some embodiments, the Fc region is selected from the group consisting of: an IgA Fc region; an IgD Fc region; an IgG Fc region, an IgE Fc region; and an IgM Fc region. In one embodiment, the Fc region is an IgG Fc region. In some embodiments, a peptide linker is situated between the Nogo receptor-1 polypeptide and said IgG Fc region. In one embodiment, the peptide linker comprises SEQ ID NO:2 $(G_4S)_2$. In some embodiments, the polypeptide tag is selected from the group consisting of: FLAG tag; Strep tag; polyhistidine tag; VSV-G tag; influenza virus hemagglutinin (HA) tag; and c-Myc tag.

In some embodiments, the non-NgR1 moiety is a polymer conjugated to said Nogo receptor-1 polypeptide. In some embodiments, the polymer is selected from the group consisting of a polyalkylene glycol, a sugar polymer, and a polypeptide. In some embodiments, the polymer is a polyalkylene glycol. In some embodiments, the polyalkylene glycol is polyethylene glycol (PEG). In some embodiments, the soluble NgR1 polypeptide is conjugated to 1, 2, 3, or 4 polymers. In some embodiments, the total molecular weight of the polymers is from 5,000 Da to 100,000 Da.

In some embodiments, the Nogo receptor-1 polypeptide is a cyclic polypeptide. In some embodiments, the cyclic polypeptide further comprises a first molecule linked at the N-terminus and a second molecule linked at the C-terminus; wherein said first molecule and said second molecule are joined to each other to form said cyclic molecule. In some embodiments, the first and second molecules are selected from the group consisting of: a biotin molecule, a cysteine residue, and an acetylated cysteine residue. In some embodiments, the first molecule is a biotin molecule attached to the N-terminus and said second molecule is a cysteine residue attached to the C-terminus of said polypeptide. In some embodiments, the first molecule is an acetylated cysteine residue attached to the N-terminus and said second molecule is a cysteine residue attached to the C-terminus of said polypeptide. In one embodiment, the C-terminal cysteine has an $NH_2$ moiety attached.

In some embodiments, the Nogo receptor-1 antagonist comprises an antibody or antigen-binding fragment thereof that binds to a mammalian Nogo-receptor. In some embodiments, the antibody is selected from the group consisting of a polyclonal antibody, a monoclonal antibody, a Fab fragment, a Fab' fragment, an $F(ab')_2$ fragment, an Fv fragment, an Fd fragment, a diabody, and a single-chain antibody. In some embodiments, the antibody or antigen-binding fragment thereof binds to a polypeptide bound by a monoclonal antibody produced by a hybridoma selected from the group consisting of: HB 7E11 (ATCC accession No. PTA-4587), HB 1H2 (ATCC accession No. PTA-4584), HB 3G5 (ATCC accession No. PTA-4586), HB 5B10 (ATCC accession No. PTA-4588), and HB 2F7 (ATCC accession No. PTA-4585).

In some embodiments, the Nogo-receptor antagonist is a an isolated polynucleotide selected from the group consisting of (a) an antisense polynucleotide; (b) a ribozyme; (c) a small interfering RNA (siRNA); and (d) a small-hairpin RNA (shRNA). In some embodiments, the polynucleotide is an antisense polynucleotide comprising at least 10 bases complementary to the coding portion of the NgR1 mRNA.

In certain embodiments, the invention includes a method of non-invasively monitoring axonal growth after treatment with an axonal growth promoting agent, comprising imaging [$^{11}$C]AFM binding to 5HTT in the affected spinal cord using Positron Emission Tomography.

In certain embodiments, the invention includes a method for monitoring axonal growth during treatment with an axonal growth promoting agent, comprising: (a) administering an axonal growth promoting agent to a mammal; and (b) imaging [$^{11}$C]AFM binding to 5HTT in the treated spinal cord using Positron Emission Tomography.

In certain embodiments, the invention includes a method for determining axonal growth following treatment with an axonal growth promoting agent, comprising: (a) administering [$^{11}$C]AFM to a mammal treated with an axonal growth promoting agent; (b) imaging [$^{11}$C]AFM binding to 5HTT in said mammal using Positron Emission Tomography; and (c) measuring lumbar uptake of [$^{11}$C]AFM as a proportion of cervical uptake of [$^{11}$C]AFM. In one embodiment, an increased ratio of lumbar uptake to cervical uptake in a mammal treated with an axonal growth promoting agent compared to the ratio of a mammal not treated with an axonal growth promoting agent is indicative of axonal growth.

In some embodiments, the treatment is for chronic SCI. In some embodiments, the treatment is for a spinal contusion.

In some embodiments, the axonal growth promoting agent is a Nogo-receptor antagonist. In some embodiments, the Nogo-receptor antagonist is selected from the group consisting of: (a) the Nogo-receptor polypeptide as described herein; (b) the antibody or antigen-binding fragment thereof as described herein; and (c) polynucleotides as described herein.

DETAILED DESCRIPTION OF THE INVENTION

Definitions and General Techniques

Figures 1A, 1B, 1C:
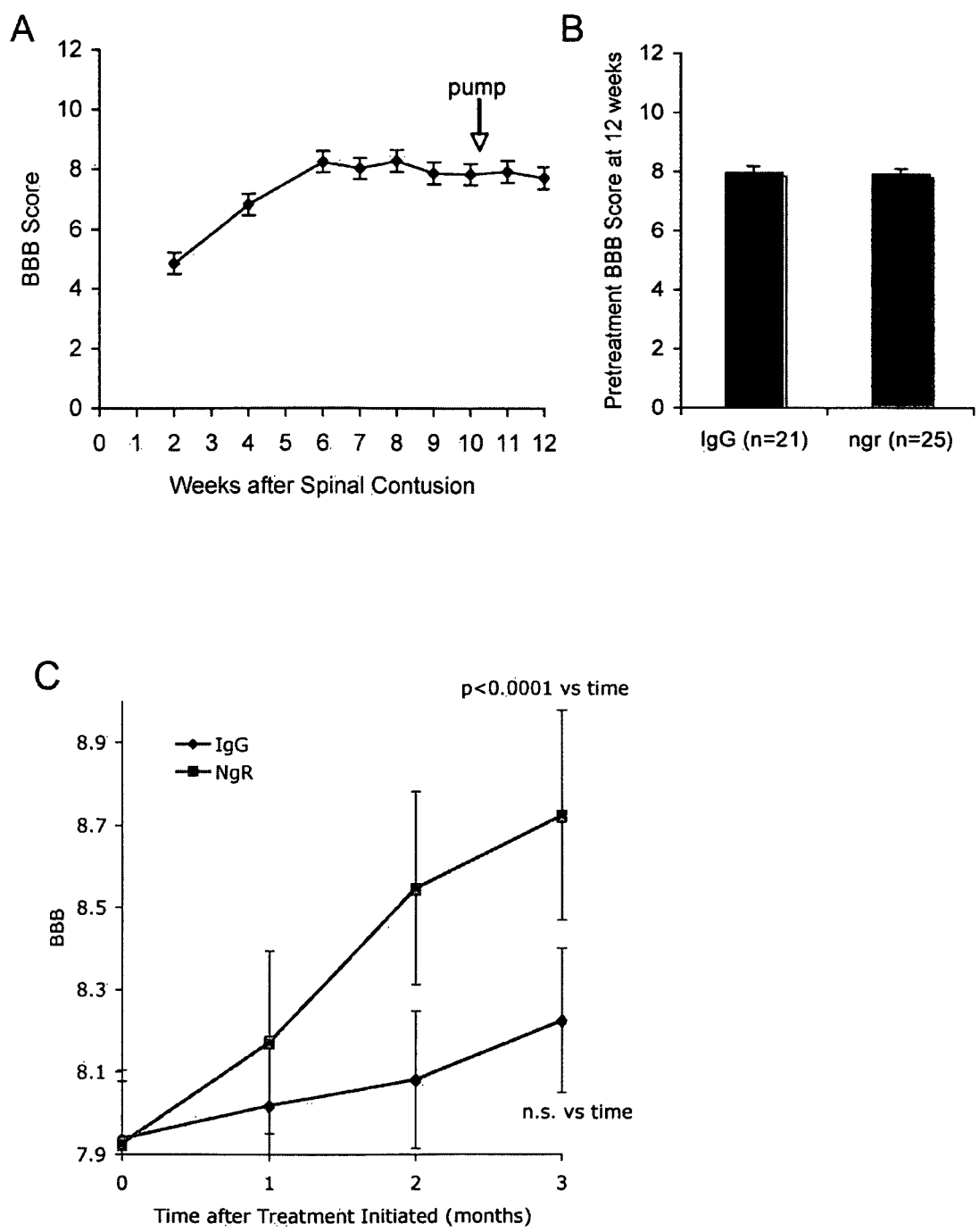
FIG. 1A is a graph depicting BBB score as a function of time for chronically spinal cord contused rats prior to treatment. Rats underwent a spinal cord contusion without therapeutic intervention and were monitored by BBB scoring (mean±sem, n=46). The BBB scores plateau by 6 weeks after contusion. A cannula connected to an osmotic minipump containing PBS was implanted into the right lateral ventricle at 10 weeks post-contusion injury (pump) without significant deficit from surgery.
FIG. 1B is a graph depicting the BBB score for each treatment group prior to initiation of treatment. Two weeks after the cannula implantation (12 weeks post-contusion injury), animals were assigned to one of two treatment groups. The PBS minipumps were replaced with new osmotic minipumps filled with 2.25 mg AA-NgR(310)ecto-Fc (0.29 mg/kg/day) or 2.25 mg rat IgG in 2 ml PBS. The locomotor BBB scores from the IgG (n=21) and AA-NgR(310)ecto-Fc-treated (n=25) groups were indistinguishable at the initiation of treatment.
FIG. 1C is a graph depicting BBB score as a function of time during treatment of the chronically spinal cord contused rats. Data are mean±sem for n=21 or 25 per group. Repeated measures ANOVA tests versus time are reported.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

Although methods and materials similar or equivalent to those described herein can be used in practice or testing of the present invention, suitable methods and materials are described below. The materials, methods and examples are illustrative only, and are not intended to be limiting. Other features and advantages of the invention will be apparent from the detailed description and from the claims.

Throughout this specification and claims, the word "comprise," or variations such as "comprises" or "comprising," will be understood to imply the inclusion of a stated integer or group of integers but not the exclusion of any other integer or group of integers.

In order to further define this invention, the following terms and definitions are herein provided.

It is to be noted that the term "a" or "an" entity, refers to one or more of that entity; for example, "an immunoglobulin molecule," is understood to represent one or more immunoglobulin molecules. As such, the terms "a" (or "an"), "one or more," and "at least one" can be used interchangeably herein.

As used herein, the term "consists of," or variations such as "consist of" or "consisting of," as used throughout the specification and claims, indicate the inclusion of any recited integer or group of integers, but that no additional integer or group of integers may be added to the specified method, structure or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

As used herein, "antibody" means an intact immunoglobulin, or an antigen-binding fragment thereof. Antibodies of this invention can be of any isotype or class (e.g., M, D, G, E, and A) or any subclass (e.g., G1-4, A1-2) and can have either a kappa (κ) or lambda (λ) light chain.

As used herein, "Fc" means a portion of an immunoglobulin heavy chain that comprises one or more heavy chain constant region domains, CH1, CH2, and CH3. For example, a portion of the heavy chain constant region of an antibody that is obtainable by papain digestion.

As used herein, "NogoR fusion protein" means a protein comprising a soluble Nogo receptor-1 moiety fused to a heterologous polypeptide.

As used herein, "humanized antibody" means an antibody in which at least a portion of the non-human sequences are replaced with human sequences. Examples of how to make humanized antibodies may be found in U.S. Pat. Nos. 6,054,297, 5,886,152, and 5,877,293.

As used herein, "chimeric antibody" means an antibody that contains one or more regions from a first antibody and one or more regions from at least one other antibody. The first antibody and the additional antibodies can be from the same or different species.

As used herein, "Nogo receptor," "NogoR," "NogoR-1," "NgR," "NgR-1," "NgR1" and "NGR1" each means Nogo receptor-1.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides," "dipeptides," "tripeptides," "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide for use in the methods of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By using the term "isolated" to describe an isolated polypeptide or a fragment, variant, or derivative thereof, it is intended that the polypeptide, or a fragment, variant, or derivative thereof, is not in its natural milieu. No particular level of purification is required. For example, an isolated polypeptide can be removed from its native or natural environment. Recombinantly produced polypeptides and proteins expressed in host cells are considered isolated for purposes of the invention, as are native or recombinant polypeptides which have been separated, fractionated, or partially or substantially purified by any suitable technique.

A "polypeptide fragment" refers to a short amino acid sequence of a larger polypeptide. Protein fragments may be "free-standing," or comprised within a larger polypeptide of which the fragment forms a part of region. Representative examples of polypeptide fragments for use in the methods of the invention, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, and about 100 amino acids or more in length.

The terms "fragment," "variant," "derivative," and "analog" when referring to a polypeptide for use in the methods of the present invention include any polypeptide which retains at least some biological activity. Polypeptides as described herein may include fragment, variant, or derivative molecules therein without limitation, so long as the polypeptide still serves its function. NgR1 polypeptides and polypeptide fragments for use in the methods of the present invention may include proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. NgR1 polypeptides and polypeptide fragments for use in the methods of the present invention may comprise variant regions, including fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. NgR1 polypeptides and polypeptide fragments for use in the methods of the invention may comprise conservative or non-conservative amino acid substitutions, deletions or additions. NgR1 polypeptides and polypeptide fragments may also include derivative molecules. Variant polypeptides may also be referred to herein as "polypeptide analogs." As used herein a "derivative" of a polypeptide or a polypeptide fragment refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

As used herein the term "disulfide bond" includes the covalent bond formed between two sulfur atoms. The amino acid cysteine comprises a thiol group that can form a disulfide bond or bridge with a second thiol group.

As used herein, "fusion protein" means a protein comprising a first polypeptide linearly connected, via peptide bonds, to a second, polypeptide. The first polypeptide and the second polypeptide may be identical or different, and they may be directly connected, or connected via a peptide linker (see below).

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can contain the nucleotide sequence of the full-length cDNA sequence, including the untranslated 5' and 3' sequences and the coding sequences. A polynucleotide may comprise a conventional phosphodiester bond or a non-conventional bond (e.g., an amide bond, such as found in peptide nucleic acids (PNA)). The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. Polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an NgR polypeptide or polypeptide fragment for use in the methods of the invention contained in a vector is considered isolated for purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids according to the methods of the present invention further include such molecules produced synthetically. In addition, a polynucleotide or a nucleic acid may be or may include a regulatory element such as a promoter, ribosome binding site, or a transcription terminator.

As used herein, a "coding region" is a portion of a nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid for use in the methods of the invention may encode heterologous coding regions, either fused or unfused to a nucleic acid encoding an NgR polypeptide or polypeptide fragment. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide for use in the methods of the present invention is RNA, for example, in the form of messenger RNA (mRNA).

Polynucleotide and nucleic acid coding regions used in the methods of the present invention may be associated with additional coding regions which encode secretory or signal peptides, which direct the secretion of a polypeptide encoded by a polynucleotide herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused," and "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

A "linker" sequence is a series of one or more amino acids separating two polypeptide coding regions in a fusion protein. A typical linker comprises at least 5 amino acids. Additional linkers comprise at least 10 or at least 15 amino acids. In certain embodiments, the amino acids of a peptide linker are selected so that the linker is hydrophilic. The linker (Gly-Gly-Gly-Gly-Ser)$_3$ (G$_4$S)$_3$ (SEQ ID NO:1) is a preferred linker that is widely applicable to many antibodies as it provides sufficient flexibility. Other linkers include (Gly-Gly-Gly-Gly-Ser)$_2$ (G$_4$S)$_2$ (SEQ ID NO:2), Glu Ser Gly Arg Ser Gly Gly Gly Gly Ser Gly Gly Gly Gly Ser (SEQ ID NO:3), Glu Gly Lys Ser Ser Gly Ser Gly Ser Glu Ser Lys Ser Thr (SEQ ID NO:4), Glu Gly Lys Ser Ser Gly Ser Gly Ser Glu Ser Lys Ser Thr Gln (SEQ ID NO:5), Glu Gly Lys Ser Ser Gly Ser Gly Ser Glu Ser Lys Val Asp (SEQ ID NO:6), Gly Ser Thr Ser Gly Ser Gly Lys Ser Ser Glu Gly Lys Gly (SEQ ID NO:7), Lys Glu Ser Gly Ser Val Ser Ser Glu Gln Leu Ala Gln Phe Arg Ser Leu Asp (SEQ ID NO:8), and Glu Ser Gly Ser Val Ser Ser Glu Glu Leu Ala Phe Arg Ser Leu Asp (SEQ ID NO:9). Examples of shorter linkers include fragments of the above linkers, and examples of longer linkers include combinations of the linkers above, combinations of fragments of the linkers above, and combinations of the linkers above with fragments of the linkers above.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes, without limitation, transcription of the gene into messenger RNA (mRNA), transfer RNA (tRNA), small hairpin RNA (shRNA), small interfering RNA (siRNA) or any other RNA product, and the translation of such mRNA into polypeptide(s), as well as any processes which regulate either transcription or translation. If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the terms "treat" or "treatment" refer to therapeutic treatment, wherein the object is to prevent or slow down (lessen) an undesired physiological change or disorder, such as the progression of the effects of a chronic nervous system disease or injury, including but not limited to, a chronic spinal cord injury. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder.

As used herein, the term "acute nervous system disease or injury" refers to a disease or injury that has not persisted after the onset of the disease of or initial injury to the nervous system for longer than a week. Treatment of an acute nervous system disease or injury is initiated within a week or less of the onset of disease or the initial injury, for example, 7 days or less, or 6 days or less, or 5 days or less, or 4 days or less, or 3 days or less, or 2 days or less, or 1 day or less.

As used herein, the term "chronic nervous system disease or injury" refers to a disease or injury that has persisted after the onset of the disease of or initial injury to the nervous system for a long period of time, for example, greater than a week. Treatment of a chronic nervous system disease or injury is initiated greater than a week after an onset of disease or an initial injury. For example, treatment of a chronic nervous system disease or injury is initiated two weeks or greater after an onset of disease or an initial injury, or three weeks or greater after an onset of disease or an initial injury, or four weeks or greater after an onset of disease or an initial injury. Additional examples of treatment of chronic nervous system disease or injury include initiation of treatment one month or greater after the onset of disease or initial injury, or two months or greater after the onset of disease or initial injury, or three months or greater after the onset of disease or initial injury, or four months or greater after the onset of disease or initial injury, or five months or greater after the onset of disease or initial injury, or six months or greater after the onset of disease or initial injury, or seven months or greater after the onset of disease or initial injury, or eight months or greater after the onset of disease or initial injury, or nine months or greater after the onset of disease or initial injury, or ten months or greater after the onset of disease or initial injury, or eleven months or greater after the onset of disease or initial injury, or twelve months or greater after the onset of disease or initial injury. Treatment of chronic nervous system disease or injury can also include a period of time of one year or greater after the onset of disease or initial injury. In a particular aspect, the treatment of chronic nervous system disease or injury is initiated three months or greater after the onset of disease or initial injury.

As used herein, the term "acute spinal cord injury" refers to an injury that has not persisted after the initial spinal cord injury for longer than a week. Treatment of acute spinal cord injury is initiated within a week or less of an initial spinal cord injury, for example, 7 days or less, or 6 days or less, or 5 days or less, or 4 days or less, or 3 days or less, or 2 days or less, or 1 day or less.

As used herein, the term "chronic spinal cord injury" refers to an injury that has persisted after the initial spinal cord injury for a long period of time, for example, greater than a week. Treatment of chronic spinal cord injury is initiated greater than a week after an initial spinal cord injury. For example, treatment of a chronic SCI is initiated two weeks or greater after the initial injury, or three weeks or greater after the initial injury, or four weeks or greater after the initial injury. Additional examples of treatment of chronic SCI include initiation of treatment one month or greater after the initial injury, or two months or greater after the initial injury, or three months or greater after the initial injury, or four months or greater after the initial injury, or five months or greater after the initial injury, or six months or greater after the initial injury, or seven months or greater after the initial injury, or eight months or greater after the initial injury, or nine months or greater after the initial injury, or ten months or greater after the initial injury, or eleven months or greater after the initial injury, or twelve months or greater after the initial injury. Treatment of chronic SCI can also include a period of time of one year or greater after the initial injury. In a particular aspect, the treatment of chronic SCI is initiated three months or greater after the initial injury.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

As used herein, a "therapeutically effective amount" refers to an amount effective, at dosages and for periods of time necessary, to achieve the desired therapeutic result. A therapeutic result may be, e.g., lessening of symptoms, prolonged survival, improved mobility, and the like. A therapeutic result need not be a "cure".

As used herein, "noninvasively monitoring" refers to techniques that do not require insertion of an instrument or device through the skin or a body orifice, such as but not limited to imaging techniques. Imaging techniques can include the use of Positron Emission Tomography (PET), which images the concentrations of biologically active molecules attached to positron-emitting radionuclides, e.g., [$^{11}$C]2-[2-(dimethylaminomethylphenylthio)]-5-fluoromethylphenylamine ([$^{11}$C]AFM), in vivo.

The term "axonal growth promoting agent" refers to any agent that promotes or stimulates the growth of axons. Examples of axonal growth promoting agents include, but are not limited to, Nogo receptor antagonists, including NgR1 polypeptides, NgR1 antibodies and antigen-binding fragments thereof, soluble Nogo receptors and fusion proteins thereof, and/or polynucleotides.

Nogo Receptor Antagonists

Any Nogo receptor antagonist may be used in the methods of the invention. For example, Nogo receptor antagonists that may be used in the methods of the invention include, but are not limited to: Nogo receptor-1 polypeptides, Nogo receptor-1 antibodies and antigen-binding fragments thereof, soluble Nogo receptors and fusion proteins thereof, and polynucleotides.

Nogo Receptor-1 Polypeptides

Certain Nogo receptor-1 polypeptides and polypeptide fragments useful, e.g., for promoting neurite outgrowth, promoting neuronal survival, promoting axonal survival, or inhibiting signal transduction by the NgR1 signaling complex can be used in the methods of the present invention. Typically, the polypeptides and polypeptide fragments useful in the methods of the invention act to block NgR1-mediated inhibition of neuronal survival, neurite outgrowth or axonal regeneration of central nervous system (CNS) neurons.

The human NgR1 polypeptide is shown below as SEQ ID NO:10.

```
Full-Length Human NgR1 (SEQ ID NO: 10):
MKRASAGGSRLLAWVLWLQAWQVAAPCPGACVCYNEPKVTTSCPQQGLQA

VPVGIPAASQRIFLHGNRISHVPAASFRACRNLTILWLHSNVLARIDAAA

FTGLALLEQLDLSDNAQLRSVDPATFHGLGRLHTLHLDRCGLQELGPGLF

RGLAALQYLYLQDNALQALPDDTFRDLGNLTHLFLHGNRISSVPERAFRG

LHSLDRLLLHQNRVAHVHPHAFRDLGRLMTLYLFANNLSALPTEALAPLR

ALQYLRLNDNPWVCDCRARPLWAWLQKFRGSSSEVPCSLPQRLAGRDLKR

LAANDLQGCAVATGPYHPIWTGRATDEEPLGLPKCCQPDAADKASVLEPG

RPASAGNALKGRVPPGDSPPGNGSGPRHINDSPFGTLPGSAEPPLTAVRP

EGSEPPGFPTSGPRRRPGCSRKNRTRSHCRLGQAGSGGGTGDSEGSGAL

PSLTCSLTPLGLALVLWTVLGPC
```

The rat NgR1 polypeptide is shown below as SEQ ID NO:11.

```
Full-Length Rat NgR1 (SEQ ID NO: 11):
MKRASSGGSRLLAWVLWLQAWRVATPCPGACVCYNEPKVTTSCPQQGLQA

VPTGIPASSQRIFLHGNRISYVPAASFQSCRNLTILWLHSNALAGIDAAA

FTGLTLLEQLDLSDNAQLRVVDPTTFRGLGHLHTLHLDRCGLQELGPGLF

RGLAALQYLYLQDNNLQALPDNTFRDLGNLTHLFLHGNRIPSVPEHAFRG

LHSLDRLLLHQNHVARVHPHAFRDLGRLMTLYLFANNLSMLPAEVLVPLR

SLQYLRLNDNPWVCDCRARPLWAWLQKFRGSSSEVPCNLPQRLAGRDLKR

LAASDLEGCAVASGPFRPFQTNQLTDEELLGLPKCCQPDAADKASVLEPG

RPASAGNALKGRVPPGDTPPGNGSGPRHINDSPFGTLPGSAEPPLTALRP

GGSEPPGLPTTGPRRRPGCSRKNRTRSHCRLGQAGSGSSGTGDAEGSGAL

PALACSLAPLGLALVLWTVLGPC
```

The mouse NgR1 polypeptide is shown below as SEQ ID NO:12.

```
Full-Length Mouse NgR1 (SEQ ID NO: 12):
MKRASSGGSRLLAWVLWLQAWRVATPCPGACVCYNEPKVTTSCPQQGLQA

VPTGIPASSQRIFLHGNRISHVPAASFQSCRNLTILWLHSNALARIDAAA

FTGLTLLEQLDLSDNAQLHVVDPTTFHGLGHLHTLHLDRCGLRELGPGLF

RGLAALQYLYLQDNNLQALPDNTFRDLGNLTHLFLHGNRIPSVPEHAFRG

LHSLDRLLLHQNHVARVHPHAFRDLGRLMTLYLFANNLSMLPAEVLMPLR

SLQYLRLNDNPWVCDCRARPLWAWLQKFRGSSSEVPCNLPQRLADRDLKR

LAASDLEGCAVASGPFRPIQTSQLTDEELLSLPKCCQPDAADKASVLEPG

RPASAGNALKGRVPPGDTPPGNGSGPRHINDSPFGTLPSSAEPPLTALRP

GGSEPPGLPTTGPRRRPGCSRKNRTRSHCRLGQAGSGASGTGDAEGSGAL

PALACSLAPLGLALVLWTVLGPC
```

Soluble Nogo Receptor-1 Polypeptides

Full-length Nogo receptor-1 consists of a signal sequence, a N-terminus region (NT), eight leucine rich repeats (LRR), a LRRCT region (a leucine rich repeat domain C-terminal of the eight leucine rich repeats), a C-terminus region (CT) and a GPI anchor.

The NgR domain designations used herein are defined as follows:

TABLE 1

Example NgR domains

| Domain | hNgR (SEQ ID: 10) | rNgR (SEQ ID NO: 11) | mNgR (SEQ ID NO: 12) |
|---|---|---|---|
| Signal Seq. | 1-26 | 1-26 | 1-26 |
| LRRNT | 27-56 | 27-56 | 27-56 |
| LRR1 | 57-81 | 57-81 | 57-81 |
| LRR2 | 82-105 | 82-105 | 82-105 |
| LRR3 | 106-130 | 106-130 | 106-130 |

TABLE 1-continued

Example NgR domains

| Domain | hNgR (SEQ ID: 10) | rNgR (SEQ ID NO: 11) | mNgR (SEQ ID NO: 12) |
|---|---|---|---|
| LRR4 | 131-154 | 131-154 | 131-154 |
| LRR5 | 155-178 | 155-178 | 155-178 |
| LRR6 | 179-202 | 179-202 | 179-202 |
| LRR7 | 203-226 | 203-226 | 203-226 |
| LRR8 | 227-250 | 227-250 | 227-250 |
| LRRCT | 260-309 | 260-309 | 260-309 |
| CTS (CT Signaling) | 310-445 | 310-445 | 310-445 |
| GPI | 446-473 | 446-473 | 446-473 |

Some embodiments of the invention provide a soluble Nogo receptor-1 polypeptide for use in the methods of the invention. Soluble Nogo receptor-1 polypeptides for use in the methods of the invention comprise an NT domain, 8 LRRs, and an LRRCT domain and lack a signal sequence and a functional GPI anchor (i.e., no GPI anchor or a GPI anchor that lacks the ability to efficiently associate to a cell membrane).

In some embodiments, a soluble Nogo receptor-1 polypeptide comprises a heterologous LRR. In some embodiments a soluble Nogo receptor-1 polypeptide comprises 2, 3, 4, 5, 6, 7, or 8 heterologous LRRs. A heterologous LRR means an LRR obtained from a protein other than Nogo receptor-1. Exemplary proteins from which a heterologous LRR can be obtained are toll-like receptor (TLR1.2); T-cell activation leucine repeat rich protein; deceorin; OMgp; insulin-like growth factor binding protein acidic labile subunit slit and robo; and toll-like receptor 4.

In some embodiments, the methods of the invention use a soluble Nogo receptor-1 polypeptide of 319 amino acids (soluble Nogo receptor-1 344, sNogoR1-344, or sNogoR344) (residues 26-344 of SEQ ID NOs: 13 and 15 or residues 27-344 of SEQ ID NO:15). In some embodiments, the invention provides a soluble Nogo receptor-1 polypeptide of 285 amino acids (soluble Nogo receptor-1 310, sNogoR1-310, or sNogoR310) (residues 26-310 of SEQ ID NOs: 14 and 16 or residues 27-310 of SEQ ID NO:16).

TABLE 1

Sequences of Human and Rat Nogo receptor-1 Polypeptides

| | |
|---|---|
| SEQ ID NO: 13 (human 1-344) | MKRASAGGSRLLAWVLWLQAWQVAAPCPGACVCYNEPK VTTSCPQQGLQAVPVGIPAASQRIFLHGNRISHVPAASFRAC RNLTILWLHSNVLARIDAAAFTGLALLEQLDLSDNAQLRSV DPATFHGLGRLHTLHLDRCGLQELGPGLFRGLAALQYLYLQ DNALQALPDDTFRDLGNLTHLFLHGNRISSVPERAFRGLHSL DRLLLHQNRVAHVHPHAFRDLGRLMTLYLFANNLSALPTE ALAPLRALQYLRLNDNPWVCDCRARPLWAWLQKFRGSSSE VPCSLPQRLAGRDLKRLAANDLQGCAVATGPYHPIWTGRA TDEEPLGLPKCCQPDAADKA |
| SEQ ID NO: 14 (human 1-310) | MKRASAGGSRLLAWVLWLQAWQVAAPCPGACVCYNEPK VTTSCPQQGLQAVPVGIPAASQRIFLHGNRISHVPAASFRAC RNLTILWLHSNVLARIDAAAFTGLALLEQLDLSDNAQLRSV DPATFHGLGRLHTLHLDRCGLQELGPGLFRGLAALQYLYLQ DNALQALPDDTFRDLGNLTHLFLHGNRISSVPERAFRGLHSL DRLLLHQNRVAHVHPHAFRDLGRLMTLYLFANNLSALPTE ALAPLRALQYLRLNDNPWVCDCRARPLWAWLQKFRGSSSE VPCSLPQRLAGRDLKRLAANDLQGCA |
| SEQ ID NO: 15 (rat 1-344) | MKRASSGGSRLPTWVLWLQAWRVATPCPGACVCYNEPKV TTSRPQQGLQAVPAGIPASSQRIFLHGNRISYVPAASFQSCRN LTILWLHSNALAGIDAAAFTGLTLLEQLDLSDNAQLRVVDP TTFRGLGHLHTLHLDRCGLQELGPGLFRGLAALQYLYLQD NNLQALPDNTFRDLGNLTHLFLHGNRIPSVPEHAFRGLHSL DRLLLHQNHVARVHPHAFRDLGRLMTLYLFANNLSMLPAE VLVPLRSLQYLRLNDNPWVCDCRARPLWAWLQKFRGSSSG |

TABLE 1-continued

Sequences of Human and Rat Nogo receptor-1 Polypeptides

| | |
|---|---|
| | VPSNLPQRLAGRDLKRLATSDLEGCAVASGPFRPFQTNQLT<br>DEELLGLPKCCQPDAADKA |
| SEQ ID NO: 16<br>(rat 1-310) | MKRASSGGSRLPTWVLWLQAWRVATPCPGACVCYNEPKV<br>TTSRPQQGLQAVPAGIPASSQRIFLHGNRISYVPAASFQSCRN<br>LTILWLHSNALAGIDAAAFTGLTLLEQLDLSDNAQLRVVDP<br>TTFRGLGHLHTLHLDRCGLQELGPGLFRGLAALQYLYLQD<br>NNLQALPDNTFRDLGNLTHLFLHGNRIPSVPEHAFRGLHSL<br>DRLLLHQNHVARVHPHAFRDLGRLMTLYLFANNLSMLPAE<br>VLVPLRSLQYLRLNDNPWVCDCRARPLWAWLQKFRGSSSG<br>VPSNLPQRLAGRDLKRLATSDLEGCA |
| SEQ ID NO: 17<br>(human 1-310<br>with ala<br>substitutions at<br>amino acid<br>positions 266<br>and 309) | MKRASAGGSRLLAWVLWLQAWQVAAPCPGACVCYNEPK<br>VTTSCPQQGLQAVPVGIPAASQRIFLHGNRISHVPAASFRAC<br>RNLTILWLHSNVLARIDAAAFTGLALLEQLDLSDNAQLRSV<br>DPATFHGLGRLHTLHLDRCGLQELGPGLFRGLAALQYLYLQ<br>DNALQALPDDTFRDLGNLTHLFLHGNRISSVPERAFRGLHSL<br>DRLLLHQNRVAHVHPHAFRDLGRLMTLYLFANNLSALPTE<br>ALAPLRALQYLRLNDNPWVCD<u>A</u>RARPLWAWLQKFRGSSSE<br>VPCSLPQRLAGRDLKRLAANDLQG<u>A</u>A |
| SEQ ID NO: 18<br>(rat 1-310 with<br>ala substitutions<br>at amino acid<br>positions 266<br>and 309) | MKRASSGGSRLPTWVLWLQAWRVATPCPGACVCYNEPKV<br>TTSRPQQGLQAVPAGIPASSQRIFLHGNRISYVPAASFQSCRN<br>LTILWLHSNALAGIDAAAFTGLTLLEQLDLSDNAQLRVVDP<br>TTFRGLGHLHTLHLDRCGLQELGPGLFRGLAALQYLYLQD<br>NNLQALPDNTFRDLGNLTHLFLHGNRIPSVPEHAFRGLHSL<br>DRLLLHQNHVARVHPHAFRDLGRLMTLYLFANNLSMLPAE<br>VLVPLRSLQYLRLNDNPWVCD<u>A</u>RARPLWAWLQKFRGSSSG<br>VPSNLPQRLAGRDLKRLATSDLEG<u>A</u>A |
| SEQ ID NO: 19<br>(human 1-344<br>with ala<br>substitutions at<br>amino acid<br>positions 266<br>and 309) | MKRASAGGSRLLAWVLWLQAWQVAAPCPGACVCYNEPK<br>VTTSCPQQGLQAVPVGIPAASQRIFLHGNRISHVPAASFRAC<br>RNLTILWLHSNVLARIDAAAFTGLALLEQLDLSDNAQLRSV<br>DPATFHGLGRLHTLHLDRCGLQELGPGLFRGLAALQYLYLQ<br>DNALQALPDDTFRDLGNLTHLFLHGNRISSVPERAFRGLHSL<br>DRLLLHQNRVAHVHPHAFRDLGRLMTLYLFANNLSALPTE<br>ALAPLRALQYLRLNDNPWVCD<u>A</u>RARPLWAWLQKFRGSSSE<br>VPCSLPQRLAGRDLKRLAANDLQG<u>A</u>AVATGPYHPIWTGRA<br>TDEEPLGLPKCCQPDAADKA |

In some embodiments of the invention, the soluble Nogo receptor-1 polypeptide for use in the methods of the invention is 70%, 75%, 80%, 85%, 90%, 95%, or 100% identical to a reference amino acid sequence selected from the group consisting of: (a) amino acids 26 to 310 of SEQ ID NO:10 or 11; (b) amino acids 26 to 344 of SEQ ID NO:10 or 11; (c) amino acids 26 to 445 of SEQ ID NO:10 or 11; (d) amino acids 26 to 309 of SEQ ID NO:10 or 11; (e) amino acids 27 to 310 of SEQ ID NO:10 or 11; (f) amino acids 28 to 344 of SEQ ID NO:10 or 11; (g) amino acids 29 to 445 of SEQ ID NO:10 or 11; (h) amino acids 30 to 309 of SEQ ID NO:10 or 11; (i) amino acids 1 to 310 of SEQ ID NO:10 or 11; (j) amino acids 1 to 344 of SEQ ID NO:10 or 11; (k) amino acids 1 to 445 of SEQ ID NO:10 or 11; (l) amino acids 1 to 309 of SEQ ID NO:10 or 11; (m) variants or derivatives of any of said reference amino acid sequences; and (n) a combination of one or more of said reference amino acid sequences or variants or derivatives thereof.

By "reference amino acid sequence" is meant the specified sequence without the introduction of any amino acid substitutions. As one of ordinary skill in the art would understand, if there are no amino acid substitutions, the soluble Nogo receptor-1 polypeptide for use in the methods of the invention comprises an amino acid sequence which is 100% identical to the reference amino acid sequence.

In one embodiment, the methods of the invention use a soluble Nogo receptor-1 polypeptide comprising an amino acid sequence identical to a soluble Nogo receptor-1 polypeptide except that at least one cysteine residue is substituted with a different amino acid, wherein said polypeptide stimulates axonal growth in chronic spinal cord injury.

Exemplary amino acid substitutions for polypeptide fragments according to this embodiment include substitutions of individual cysteine residues with different amino acids. Any different amino acid may be substituted for a cysteine in the polypeptides of the invention. Which different amino acid is used depends on a number of criteria, for example, the effect of the substitution on the conformation of the polypeptide fragment, the charge of the polypeptide fragment, or the hydrophilicity of the polypeptide fragment. Amino acid substitutions for the amino acids of the polypeptides of the invention and the reference amino acid sequence can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Typical amino acids to substitute for cysteines in the reference amino acid include alanine, serine, threonine, in particular, alanine. Making such substitutions through engineering of a polynucleotide encoding the polypeptide fragment is well within the routine expertise of one of ordinary skill in the art.

Cysteine residues that can be substituted in human NgR1 include C27, C31, C33, C43, C80, C140, C264, C266, C287, C309, C335, C336, C419, C429, C455 and C473. Cysteine residues that can substituted in rat NgR1 include C27, C31, C33, C80, C140, C264, C266, C287, C309, C335, C336, C419, C429, C455 and C473. Cysteine residues that can substituted in mouse NgR1 include C27, C31, C33, C43, C80, C140, C264, C266, C287, C309, C335, C336, C419, C429, C455 and C473.

In some embodiments, the soluble Nogo receptor-1 polypeptide for use in the methods of the invention is a component of a fusion protein that further comprises a heterologous polypeptide. In some embodiments, the heterologous polypeptide is an immunoglobulin constant domain. In some embodiments, the immunoglobulin constant domain is a heavy chain constant domain. In some embodiments, the heterologous polypeptide is an Fc fragment. In some embodiments the Fc is joined to the C-terminal end of the soluble Nogo receptor-1 polypeptide. In some embodiments the fusion Nogo receptor-1 protein is a dimer. The invention further encompasses variants, analogs, or derivatives of polypeptide fragments as described above.

Exemplary soluble NgR-Fc fusion proteins with cysteine substitutions are Ala-Ala-human(h)NgR1(310)-Fc which comprises Fc joined to the C-terminal end of a soluble polypeptide with the amino acid sequence of SEQ ID NO:17, Ala-Ala-rat(r)NgR1(310)-Fc which comprises Fc joined to the C-terminal end of a soluble polypeptide with the amino acid sequence of SEQ ID NO:18, and Ala-Ala-human(h)NgR1(344)-Fc which comprises Fc joined to the C-terminal end of a soluble polypeptide with the amino acid sequence of SEQ ID NO:19.

In the present invention, a polypeptide for use in the methods of the invention can be composed of amino acids joined to each other by peptide bonds or modified peptide bonds, i.e., peptide isosteres, and may contain amino acids other than the 20 gene-encoded amino acids (e.g., non-naturally occurring amino acids). The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide.

Also, a given polypeptide for use in the methods of the invention may contain many types of modifications. Polypeptides may be branched, for example, as a result of ubiquitination, and they may be cyclic, with or without branching. Cyclic, branched, and branched cyclic polypeptides may result from natural processes or may be made by synthetic methods. Modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

Polypeptides described herein for use in the methods of the invention may be cyclic. Cyclization of the polypeptides reduces the conformational freedom of linear peptides and results in a more structurally constrained molecule. Many methods of peptide cyclization are known in the art. For example, "backbone to backbone" cyclization by the formation of an amide bond between the N-terminal and the C-terminal amino acid residues of the peptide. The "backbone to backbone" cyclization method includes the formation of disulfide bridges between two α-thio amino acid residues (e.g., cysteine, homocysteine). Certain peptides of the present invention include modifications on the N- and C-terminus of the peptide to form a cyclic polypeptide. Such modifications include, but are not limited, to cysteine residues, acetylated cysteine residues, cysteine residues with a NH2 moiety and biotin. Other methods of peptide cyclization are described in Li & Roller, *Curr. Top. Med. Chem.* 3:325-341 (2002) and U.S. Patent Publication No. U.S. 2005-0260626 A1, which are incorporated by reference herein in their entirety.

In methods of the present invention, an NgR1 polypeptide or polypeptide fragment of the invention can be administered directly as a preformed polypeptide, or indirectly through a nucleic acid vector. In some embodiments of the invention, an NgR1 polypeptide or polypeptide fragment of the invention is administered in a method that includes: (1) transforming or transfecting an implantable host cell with a nucleic acid, e.g., a vector, that expresses an NgR1 polypeptide or polypeptide fragment of the invention; and (2) implanting the transformed host cell into a mammal, at the site of a disease, disorder or injury. For example, the transformed host cell can be implanted at the site of a chronic SCI. In some embodiments of the invention, the implantable host cell is removed from a mammal, temporarily cultured, transformed or transfected with an isolated nucleic acid encoding an NgR1 polypeptide or polypeptide fragment thereof, and implanted back into the same mammal from which it was removed. The cell can be, but is not required to be, removed from the same site at which it is implanted. Such embodiments, sometimes known as ex vivo gene therapy, can provide a continuous supply of the NgR1 polypeptide or polypeptide fragment thereof, localized at the site of action, for a limited period of time.

Additional details regarding NgR polypeptides for use in the methods of the invention and methods and materials for obtaining these molecules are described below and can also be found in U.S. Pat. No. 7,465,705 and U.S. Patent Appl. No. 2008/0274112, both of which are incorporated by reference in their entirety.

Fusion Proteins and Conjugated Polypeptides

Some embodiments of the methods of the invention involve the use of an NgR1 polypeptide that is not the full-length NgR1 protein, e.g., polypeptide fragments of NgR1, fused to a non-NgR1 moiety to form a fusion protein. Such fusion proteins can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the non-NgR1 moiety can be inert or biologically active. Also, it can be chosen to be stably fused to a NgR1 polypeptide or to be cleavable, in vitro or in vivo. Heterologous moieties to accomplish these other objectives are known in the art.

In some embodiments, the polypeptides for use in the methods of the invention further comprise a heterologous polypeptide. In some embodiments, the heterologous polypeptide is an immunoglobulin constant domain. In some embodiments, the immunoglobulin constant domain is a heavy chain constant domain. In some embodiments, the heterologous polypeptide is an Fc fragment. In some embodiments the Fc is joined to the C-terminal end of the polypeptides for use in the methods of the invention. In some embodiments the fusion is a dimer. The methods of the invention further encompass the use of variants, analogs, or derivatives of polypeptide fragments as described above.

As an alternative to expression of a fusion protein, a chosen heterologous moiety can be preformed and chemically conjugated to the NgR polypeptide for use in the methods of the invention. In most cases, a chosen heterologous moiety will function similarly, whether fused or conjugated to the NgR polypeptide. Therefore, in the following discussion of heterologous amino acid sequences, unless otherwise noted, it is to be understood that the heterologous sequence can be joined to the NgR polypeptide in the form of a fusion protein or as a chemical conjugate.

NgR1 aptamers and antibodies and fragments thereof for use in the methods disclosed herein may also be recombinantly fused to a heterologous polypeptide at the N- or C-terminus or chemically conjugated (including covalent and non-covalent conjugations) to polypeptides or other compositions. For example, NgR1 antagonist aptamers and antibodies and fragments thereof may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

NgR1 antagonist polypeptides, aptamers, and antibodies and fragments thereof for use in the methods disclosed herein include derivatives that are modified, i.e., by the covalent attachment of any type of molecule such that covalent attachment does not prevent the NgR1 antagonist polypeptide, aptamer, or antibody from inhibiting the biological function of NgR1. For example, but not by way of limitation, the NgR1 antagonist polypeptides, aptamers and antibodies and fragments thereof for use in the methods of the present invention may be modified e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

NgR1 antagonist polypeptides, aptamers and antibodies and fragments thereof for use in the methods disclosed herein can be composed of amino acids joined to each other by peptide bonds or modified peptide bonds, i.e., peptide isosteres, and may contain amino acids other than the 20 gene-encoded amino acids. NgR1 antagonist polypeptides, aptamers and antibodies and fragments thereof may be modified by natural processes, such as posttranslational processing, or by chemical modification techniques which are well known in the art. Such modifications are well described in basic texts and in more detailed monographs, as well as in a voluminous research literature. Modifications can occur anywhere in the NgR1 antagonist polypeptide, aptamer or antibody or fragments thereof, including the peptide backbone, the amino acid side-chains and the amino or carboxyl termini, or on moieties such as carbohydrates. It will be appreciated that the same type of modification may be present in the same or varying degrees at several sites in a given NgR1 antagonist polypeptide, aptamer or antibody or fragments thereof. Also, a given NgR1 antagonist polypeptide, aptamer or antibody or fragments thereof may contain many types of modifications. NgR1 antagonist polypeptides, aptamers or antibodies or fragments thereof may be branched, for example, as a result of ubiquitination, and they may be cyclic, with or without branching. Cyclic, branched, and branched cyclic NgR1 antagonist polypeptides, aptamers and antibodies or fragments thereof may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The heterologous polypeptide to which the NgR1 antagonist polypeptide, aptamer or antibody or fragments thereof is fused is useful to target the NgR1 antagonist polypeptide, aptamer or antibody or fragments thereof. NgR1 antagonist fusion proteins, aptamers and antibodies or fragments thereof can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the NgR1 antagonist polypeptide, aptamer or antibody or fragments thereof or to be cleavable, in vitro or in vivo. Heterologous moieties to accomplish these other objectives are known in the art.

As an alternative to expression of an NgR1 antagonist fusion polypeptide, aptamer or antibody or fragments thereof, a chosen heterologous moiety can be preformed and chemically conjugated to the antagonist polypeptide, aptamer, or antibody. In most cases, a chosen heterologous moiety will function similarly, whether fused or conjugated to the NgR1 antagonist polypeptide, aptamer, or antibody or fragments thereof. Therefore, in the following discussion of heterologous amino acid sequences, unless otherwise noted, it is to be understood that the heterologous sequence can be joined to the NgR1 antagonist polypeptide, aptamer, or antibody or fragments thereof in the form of a fusion protein or as a chemical conjugate.

Pharmacologically active polypeptides such as NgR1 antagonist polypeptides, aptamers, or antibodies or fragments thereof may exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of relatively small polypeptides such as polypeptide fragments of the NgR signaling domain can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known. Examples include serum albumins such as, e.g., bovine serum albumin (BSA) or human serum albumin (HSA).

Due to its long half-life, wide in vivo distribution, and lack of enzymatic or immunological function, essentially fulllength human serum albumin (HSA), or an HSA fragment, is commonly used as a heterologous moiety. Through application of methods and materials such as those taught in Yeh et al., *Proc. Natl. Acad. Sci. USA*, 89:1904-08 (1992) and Syed et al., *Blood* 89:3243-52 (1997), HSA can be used to form a fusion protein or polypeptide conjugate that displays pharmacological activity by virtue of the NgR polypeptide moiety while displaying significantly increased in vivo stability, e.g., 10-fold to 100-fold higher. The C-terminus of the HSA can be fused to the N-terminus of the NgR polypeptide moiety. Since HSA is a naturally secreted protein, the HSA signal sequence can be exploited to obtain secretion of the fusion protein into the cell culture medium when the fusion protein is produced in a eukaryotic, e.g., mammalian, expression system.

In certain embodiments, NgR1 antagonist polypeptides, aptamers, antibodies, and antibody fragments thereof for use in the methods of the present invention further comprise a targeting moiety. Targeting moieties include a protein or a peptide which directs localization to a certain part of the body, for example, to the brain or compartments therein. In certain embodiments, NgR1 antagonist polypeptides, aptamers, antibodies or antibody fragments thereof for use in the methods of the present invention are attached or fused to a brain targeting moiety. The brain targeting moieties are attached covalently (e.g., direct, translational fusion, or by chemical linkage either directly or through a spacer molecule, which can be optionally cleavable) or non-covalently attached (e.g., through reversible interactions such as avidin:biotin, protein A:IgG, etc.). In other embodiments, the NgR1 antagonist polypeptides, aptamers, antibodies, or antibody fragments thereof for use in the methods of the present invention thereof are attached to one more brain targeting moieties. In additional embodiments, the brain targeting moiety is attached to a plurality of NgR1 antagonist polypeptides, aptamers, antibodies, or antibody fragments thereof for use in the methods of the present invention.

A brain targeting moiety associated with an NgR1 antagonist polypeptide, aptamer, antibody, or antibody fragment thereof enhances brain delivery of such an NgR1 antagonist polypeptide, aptamer, antibody, or antibody fragment thereof. A number of polypeptides have been described which, when fused to a protein or therapeutic agent, delivers the protein or therapeutic agent through the blood brain barrier. Non-limiting examples include the single domain antibody FC5 (Abulrob et al. (2005) *J. Neurochem.* 95, 1201-1214); mAB 83-14, a monoclonal antibody to the human insulin receptor (Pardridge et al. (1995) *Pharmacol. Res.* 12, 807-816); the B2, B6 and B8 peptides binding to the human transferrin receptor (hTfR) (Xia et al. (2000) *J. Virol.* 74, 11359-11366); the OX26 monoclonal antibody to the transferrin receptor (Pardridge et al. (1991) *J. Pharmacol. Exp. Ther.* 259, 66-70); diptheria toxin conjugates (see, e.g., Gaillard et al., *International Congress Series* 1277:185-198 (2005); and SEQ ID NOs: 1-18 of U.S. Pat. No. 6,306,365. The contents of the above references are incorporated herein by reference in their entirety.

Enhanced brain delivery of an NgR1 composition is determined by a number of means well established in the art. For example, administering to an animal a radioactively labelled NgR1 antagonist polypeptide, aptamer, antibody, or antibody fragment thereof linked to a brain targeting moiety; determining brain localization; and comparing localization with an equivalent radioactively labelled NgR1 antagonist polypeptide, aptamer, antibody, or antibody fragment thereof that is not associated with a brain targeting moiety. Other means of determining enhanced targeting are described in the above references.

Some embodiments of the invention employ an NgR polypeptide moiety fused to a hinge and Fc region, i.e., the C-terminal portion of an Ig heavy chain constant region, in the methods of the invention. In some embodiments, amino acids in the hinge region may be substituted with different amino acids. Exemplary amino acid substitutions for the hinge region according to these embodiments include substitutions of individual cysteine residues in the hinge region with different amino acids. Any different amino acid may be substituted for a cysteine in the hinge region. Amino acid substitutions for the amino acids of the polypeptides of the invention and the reference amino acid sequence can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Typical amino acids to substitute for cysteines in the reference amino acid include alanine, serine, threonine, in particular, serine and alanine. Making such substitutions through engineering of a polynucleotide encoding the polypeptide fragment is well within the routine expertise of one of ordinary skill in the art.

Potential advantages of an NgR-polypeptide-Fc fusion include solubility, in vivo stability, and multivalency, e.g., dimerization. The Fc region used can be an IgA, IgD, or IgG Fc region (hinge-CH2-CH3). Alternatively, it can be an IgE or IgM Fc region (hinge-CH2-CH3-CH4). An IgG Fc region is generally used, e.g., an IgG1 Fc region or IgG4 Fc region. Materials and methods for constructing and expressing DNA encoding Fc fusions are known in the art and can be applied to obtain fusions without undue experimentation. Some embodiments of the invention employ a fusion protein such as those described in Capon et al., U.S. Pat. Nos. 5,428,130 and 5,565,335.

The signal sequence is a polynucleotide that encodes an amino acid sequence that initiates transport of a protein across the membrane of the endoplasmic reticulum. Signal sequences useful for constructing an immunofusion include antibody light chain signal sequences, e.g., antibody 14.18 (Gillies et al., *J. Immunol. Meth.*, 125:191-202 (1989)), antibody heavy chain signal sequences, e.g., the MOPC141 antibody heavy chain signal sequence (Sakano et al., *Nature* 286:5774 (1980)). Alternatively, other signal sequences can be used. See, e.g., Watson, *Nucl. Acids Res.* 12:5145 (1984). The signal peptide is usually cleaved in the lumen of the endoplasmic reticulum by signal peptidases. This results in the secretion of an immunofusion protein containing the Fc region and the NgR polypeptide moiety.

In some embodiments, the DNA sequence may encode a proteolytic cleavage site between the secretion cassette and the NgR polypeptide moiety. Such a cleavage site may provide, e.g., for the proteolytic cleavage of the encoded fusion protein, thus separating the Fc domain from the target protein. Useful proteolytic cleavage sites include amino acid sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusion DNA is placed under the control of the enhancer and promoter of the human cytomegalovirus. See, e.g., Lo et al., *Biochim. Biophys. Acta* 1088:712 (1991); and Lo et al., *Protein Engineering* 11:495-500 (1998). An appropriate host cell can be transformed or transfected with a DNA that encodes an NgR1 polypeptide or polypeptide fragment of the invention and used for the expression and secretion of the polypeptide. Host cells that are typically used include immortal hybridoma cells, myeloma cells, 293 cells, Chinese hamster ovary (CHO) cells, Hela cells, and COS cells.

Fully intact, wild-type Fc regions display effector functions that normally are unnecessary and undesired in an Fc fusion protein for use in the methods of the present invention. Therefore, certain binding sites typically are deleted from the Fc region during the construction of the secretion cassette. For example, since coexpression with the light chain is unnecessary, the binding site for the heavy chain binding protein, Bip (Hendershot et al., *Immunol. Today* 8:111-14 (1987)), is deleted from the $C_H2$ domain of the Fc region of IgE, such that this site does not interfere with the efficient secretion of the immunofusion. Transmembrane domain sequences, such as those present in IgM, also are generally deleted.

The IgG1 Fc region is most often used. Alternatively, the Fc region of the other subclasses of immunoglobulin gamma (gamma-2, gamma-3 and gamma-4) can be used in the secretion cassette. The IgG1 Fc region of immunoglobulin gamma-1 is generally used in the secretion cassette and includes at least part of the hinge region, the $C_H2$ region, and the $C_H3$ region. In some embodiments, the Fc region of immunoglobulin gamma-1 is a $C_H2$-deleted-Fc, which includes part of the hinge region and the $C_H3$ region, but not the $C_H2$ region. A $C_H2$-deleted-Fc has been described by Gillies et al., *Hum. Antibod. Hybridomas* 1:47 (1990). In some embodiments, the Fc region of one of IgA, IgD, IgE, or IgM, is used.

NgR-polypeptide-moiety-Fc fusion proteins for use in the methods of the invention can be constructed in several different configurations. In one configuration the C-terminus of the NgR polypeptide moiety is fused directly to the N-terminus of the Fc hinge moiety. In a slightly different configuration, a short polypeptide, e.g., 2-10 amino acids, is incorporated into the fusion between the N-terminus of the NgR polypeptide moiety and the C-terminus of the Fc moiety. In the alternative configuration, the short polypeptide is incorporated into the fusion between the C-terminus of the NgR polypeptide moiety and the N-terminus of the Fc moiety. An exemplary embodiment of this configuration is NgR1(310)-2XG$_4$S-Fc, which is amino acids 26-310 of SEQ ID NO:10 linked to (Gly-Gly-Gly-Gly-Ser)$_2$ (SEQ ID NO:2) which is linked to Fc. Such a linker provides conformational flexibility, which may improve biological activity in some circumstances. If a sufficient portion of the hinge region is retained in the Fc moiety, the NgR-polypeptide-moiety-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Any of a number of cross-linkers that contain a corresponding amino-reactive group and thiol-reactive group can be used to link an NgR polypeptide or polypeptide fragment for use in the methods of the invention to serum albumin. Examples of suitable linkers include amine reactive cross-linkers that insert a thiol-reactive maleimide, e.g., SMCC, AMAS, BMPS, MBS, EMCS, SMPB, SMPH, KMUS, and GMBS. Other suitable linkers insert a thiol-reactive haloacetate group, e.g., SBAP, SIA, STAB. Linkers that provide a protected or non-protected thiol for reaction with sulfhydryl groups to product a reducible linkage include SPDP, SMPT, SATA, and SATP. Such reagents are commercially available (e.g., Pierce Chemical Company, Rockford, Ill.).

Conjugation does not have to involve the N-terminus of an NgR polypeptide or polypeptide fragment of the invention or the thiol moiety on serum albumin. For example, NgR-polypeptide-albumin fusions can be obtained using genetic engineering techniques, wherein the NgR polypeptide moiety is fused to the serum albumin gene at its N-terminus, C-terminus, or both.

NgR polypeptides for use in the methods of the invention can be fused to a polypeptide tag. The term "polypeptide tag," as used herein, is intended to mean any sequence of amino acids that can be attached to, connected to, or linked to an NgR polypeptide and that can be used to identify, purify, concentrate or isolate the NgR polypeptide. The attachment of the polypeptide tag to the NgR polypeptide may occur, e.g., by constructing a nucleic acid molecule that comprises: (a) a nucleic acid sequence that encodes the polypeptide tag, and (b) a nucleic acid sequence that encodes an NgR polypeptide. Exemplary polypeptide tags include, e.g., amino acid sequences that are capable of being post-translationally modified, e.g., amino acid sequences that are biotinylated. Other exemplary polypeptide tags include, e.g., amino acid sequences that are capable of being recognized and/or bound by an antibody (or fragment thereof) or other specific binding reagent. Polypeptide tags that are capable of being recognized by an antibody (or fragment thereof) or other specific binding reagent include, e.g., those that are known in the art as "epitope tags." An epitope tag may be a natural or an artificial epitope tag. Natural and artificial epitope tags are known in the art, including, e.g., artificial epitopes such as FLAG, Strep, or poly-histidine peptides.

Natural and artificial epitope tags are known in the art, including, e.g., artificial epitopes such as FLAG, Strep, or poly-histidine peptides. FLAG peptides include the sequence Asp-Tyr-Lys-Asp-Asp-Asp-Asp-Lys (SEQ ID NO:20) or Asp-Tyr-Lys-Asp-Glu-Asp-Asp-Lys (SEQ ID NO:21) (Einhauer, A. and Jungbauer, A., *J. Biochem. Biophys. Methods* 49:1-3:455-465 (2001)). The Strep epitope has the sequence Ala-Trp-Arg-His-Pro-Gln-Phe-Gly-Gly (SEQ ID NO:22). The VSV-G epitope can also be used and has the sequence Tyr-Thr-Asp-Ile-Glu-Met-Asn-Arg-Leu-Gly-Lys (SEQ ID NO:23). Another artificial epitope is a poly-His sequence having six histidine residues (His-His-His-His-His-His) (SEQ ID NO:24)). Naturally-occurring epitopes include the influenza virus hemagglutinin (HA) sequence Tyr-Pro-Tyr-Asp-Val-Pro-Asp-Tyr-Ala-Ile-Glu-Gly-Arg (SEQ ID NO:25) recognized by the monoclonal antibody 12CA5 (Murray et al., *Anal. Biochem.* 229:170-179 (1995)) and the eleven amino acid sequence from human c-myc (Myc) recognized by the monoclonal antibody 9E10 (Glu-Gln-Lys-Leu-Leu-Ser-Glu-Glu-Asp-Leu-Asn (SEQ ID NO:26) (Manstein et al., *Gene* 162:129-134 (1995)). Another useful epitope is the tripeptide Glu-Glu-Phe which is recognized by the monoclonal antibody YL 1/2. (Stammers et al., *FEBS Lett.* 283:298-302(1991)).

In certain embodiments, the NgR polypeptide and the polypeptide tag for use in the methods of the invention may be connected via a linking amino acid sequence. As used herein, a "linking amino acid sequence" may be an amino acid sequence that is capable of being recognized and/or cleaved by one or more proteases. Amino acid sequences that can be recognized and/or cleaved by one or more proteases are known in the art. Exemplary amino acid sequences are those that are recognized by the following proteases: factor VIIa, factor IXa, factor Xa, APC, t-PA, u-PA, trypsin, chymotrypsin, enterokinase, pepsin, cathepsin B,H,L,S,D, cathepsin G, renin, angiotensin converting enzyme, matrix metalloproteases (collagenases, stromelysins, gelatinases), macrophage elastase, Cir, and Cis. The amino acid sequences that are recognized by the aforementioned proteases are known in the art. Exemplary sequences recognized by certain proteases can be found, e.g., in U.S. Pat. No. 5,811,252.

Polypeptide tags can facilitate purification using commercially available chromatography media.

In some embodiments of the invention, an NgR polypeptide fusion construct for use in the methods of the invention is used to enhance the production of an NgR polypeptide moiety in bacteria. In such constructs, a bacterial protein normally expressed and/or secreted at a high level is employed as the N-terminal fusion partner of an NgR1 polypeptide or polypeptide fragment of the invention. See, e.g., Smith et al., *Gene* 67:31 (1988); Hopp et al., *Biotechnology* 6:1204 (1988); La Vallie et al., *Biotechnology* 11:187 (1993).

By fusing an NgR polypeptide moiety at the amino and carboxy termini of a suitable fusion partner, bivalent or tetravalent forms of an NgR1 polypeptide or polypeptide fragment for use in the methods of the invention can be obtained. For example, an NgR polypeptide moiety can be fused to the amino and carboxy termini of an Ig moiety to produce a bivalent monomeric polypeptide containing two NgR polypeptide moieties. Upon dimerization of two of these monomers, by virtue of the Ig moiety, a tetravalent form of an NgR polypeptide is obtained. Such multivalent forms can be used to achieve increased binding affinity for the target. Multivalent forms of an NgR1 polypeptide or polypeptide fragment for use in the methods of the invention also can be obtained by placing NgR polypeptide moieties in tandem to form concatamers, which can be employed alone or fused to a fusion partner such as Ig or HSA.

Conjugated Polymers (Other than Polypeptides)

In some embodiments of the methods of the invention an NgR polypeptide or polypeptide fragment of the invention is conjugated (covalently linked) to one or more polymers. Examples of polymers suitable for such conjugation include polypeptides (discussed above), sugar polymers and polyalkylene glycol chains. Typically, but not necessarily, a polymer is conjugated to the NgR polypeptide or polypeptide fragment of the invention for the purpose of improving one or more of the following: solubility, stability, or bioavailability.

The class of polymer generally used for conjugation to an NgR polypeptide or polypeptide fragment of the invention is a polyalkylene glycol. Polyethylene glycol (PEG) is most frequently used. PEG moieties, e.g., 1, 2, 3, 4 or 5 PEG polymers, can be conjugated to each NgR polypeptide to increase serum half life, as compared to the NgR polypeptide alone. PEG moieties are non-antigenic and essentially biologically inert. PEG moieties used in the practice of the invention may be branched or unbranched.

The number of PEG moieties attached to the NgR polypeptide and the molecular weight of the individual PEG chains can vary. In general, the higher the molecular weight of the polymer, the fewer polymer chains attached to the polypeptide. Usually, the total polymer mass attached to an NgR polypeptide or polypeptide fragment is from 20 kDa to 40 kDa. Thus, if one polymer chain is attached, the molecular weight of the chain is generally 20-40 kDa. If two chains are attached, the molecular weight of each chain is generally 10-20 kDa. If three chains are attached, the molecular weight is generally 7-14 kDa.

The polymer, e.g., PEG, can be linked to the NgR polypeptide through any suitable, exposed reactive group on the polypeptide. The exposed reactive group(s) can be, e.g., an N-terminal amino group or the epsilon amino group of an internal lysine residue, or both. An activated polymer can react and covalently link at any free amino group on the NgR polypeptide. Free carboxylic groups, suitably activated carbonyl groups, hydroxyl, guanidyl, imidazole, oxidized carbohydrate moieties and mercapto groups of the NgR polypeptide (if available) also can be used as reactive groups for polymer attachment.

In a conjugation reaction, from about 1.0 to about 10 moles of activated polymer per mole of polypeptide, depending on polypeptide concentration, is typically employed. Usually, the ratio chosen represents a balance between maximizing the reaction while minimizing side reactions (often non-specific) that can impair the desired pharmacological activity of the NgR polypeptide moiety. Preferably, at least 50% of the biological activity (as demonstrated, e.g., in any of the assays described herein or known in the art) of the NgR polypeptide is retained, and most preferably nearly 100% is retained.

The polymer can be conjugated to the NgR polypeptide using conventional chemistry. For example, a polyalkylene glycol moiety can be coupled to a lysine epsilon amino group of the NgR polypeptide. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS and norleucine-NHS, SC. These reagents are commercially available. Additional amine-reactive PEG linkers can be substituted for the succinimidyl moiety. These include, e.g., isothiocyanates, nitrophenylcarbonates (PNP), epoxides, benzotriazole carbonates, SC-PEG, tresylate, aldehyde, epoxide, carbonylimidazole and PNP carbonate. Conditions are usually optimized to maximize the selectivity and extent of reaction. Such optimization of reaction conditions is within ordinary skill in the art.

PEGylation can be carried out by any of the PEGylation reactions known in the art. See, e.g., *Focus on Growth Factors* 3: 4-10 (1992) and European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. PEG esterified to N-hydroxysuccinimide (NHS) is a frequently used activated PEG ester. As used herein, "acylation" includes without limitation the following types of linkages between the therapeutic protein and a water-soluble polymer such as PEG: amide, carbamate, urethane, and the like. See, e.g., *Bioconjugate Chem.* 5: 133-140 (1994). Reaction parameters are generally selected to avoid temperature, solvent, and pH conditions that would damage or inactivate the NgR polypeptide.

Generally, the connecting linkage is an amide and typically at least 95% of the resulting product is mono-, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, hydrophobic exchange chromatography, and electrophoresis.

PEGylation by alkylation generally involves reacting a terminal aldehyde derivative of PEG with an NgR1 polypeptide or polypeptide fragment of the invention in the presence of a reducing agent. In addition, one can manipulate the reaction conditions to favor PEGylation substantially only at the N-terminal amino group of the NgR polypeptide, i.e., a mono-PEGylated protein. In either case of mono-PEGylation or poly-PEGylation, the PEG groups are typically attached to the protein via a —CH2-NH— group. With particular reference to the —CH2- group, this type of linkage is known as an "alkyl" linkage.

Derivatization via reductive alkylation to produce an N-terminally targeted mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water-soluble polymer that contains a reactive group, such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water-soluble polymers. The polymer selected is typically modified to have a single reactive group, such as an active ester for acylation or an aldehyde for alkylation, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, e.g., Harris et al., U.S. Pat. No. 5,252,714). The polymer may be branched or unbranched. For the acylation reactions, the polymer(s) selected typically have a single reactive ester group. For reductive alkylation, the polymer(s) selected typically have a single reactive aldehyde group. Generally, the water-soluble polymer will not be selected from naturally occurring glycosyl residues, because these are usually made more conveniently by mammalian recombinant expression systems.

Methods for preparing a PEGylated NgR polypeptides for use in the methods of the invention generally includes the steps of (a) reacting an NgR1 polypeptide or polypeptide fragment of the invention with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case-by-case based on known parameters and the desired result. For example, a larger the ratio of PEG to protein, generally leads to a greater the percentage of poly-PEGylated product.

Reductive alkylation to produce a substantially homogeneous population of mono-polymer/NgR polypeptide generally includes the steps of: (a) reacting an NgR1 polypeptide or polypeptide fragment of the invention with a reactive PEG molecule under reductive alkylation conditions, at a pH suitable to permit selective modification of the N-terminal amino group of NgR; and (b) obtaining the reaction product(s).

For a substantially homogeneous population of mono-polymer/NgR polypeptide, the reductive alkylation reaction conditions are those that permit the selective attachment of the water-soluble polymer moiety to the N-terminus of a NgR polypeptide or polypeptide fragment of the invention. Such reaction conditions generally provide for pKa differences between the lysine side chain amino groups and the N-terminal amino group. For purposes of the present invention, the pH is generally in the range of 3-9, typically 3-6.

NgR polypeptides for use in the methods of the invention can include a tag, e.g., a moiety that can be subsequently released by proteolysis. Thus, the lysine moiety can be selectively modified by first reacting a His-tag modified with a low-molecular-weight linker such as Traut's reagent (Pierce Chemical Company, Rockford, Ill.) which will react with both the lysine and N-terminus, and then releasing the His tag. The polypeptide will then contain a free SH group that can be selectively modified with a PEG containing a thiol-reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce Chemical Company, Rockford, Ill.). Similarly one could react the protein with an amine-reactive linker that inserts a maleimide (e.g., SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH.

In some embodiments, the polyalkylene glycol moiety is coupled to a cysteine group of the NgR polypeptide. Coupling can be effected using, e.g., a maleimide group, a vinylsulfone group, a haloacetate group, or a thiol group.

Optionally, the NgR polypeptide is conjugated to the polyethylene-glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, generally at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

Antibodies

The methods of the invention may be performed using an antibody or an antigen-binding fragment thereof that specifically binds a Nogo receptor-1 polypeptide. The antibody or antigen-binding fragment for use in the methods of the invention may be produced in vivo or in vitro. Production of the antibody or antigen-binding fragment is discussed below.

An antibody or an antigen-binding fragment thereof for use in the methods of the invention inhibits the binding of Nogo receptor-1 to a ligand (e.g., NogoA, NogoB, NogoC, MAG, OMgp) and decreases myelin-mediated inhibition of neurite outgrowth and sprouting, particularly axonal growth, and attenuates myelin mediated growth cone collapse.

In some embodiments, the anti-Nogo receptor-1 antibody or antigen-binding fragment thereof is murine. In some embodiments, the Nogo receptor-1 is from rat. In other embodiments, the Nogo receptor-1 is human. In some embodiments the anti-Nogo receptor-1 antibody or antigen-binding fragment thereof is recombinant, engineered, humanized, and/or chimeric.

In some embodiments, the antibody is selected from the group consisting of: monoclonal 7E11 (ATCC® accession No. PTA-4587); monoclonal 1E12 (ATCC® accession No. PTA-4584); monoclonal 2F7 (ATCC® accession No. PTA-4585); monoclonal 3G5 (ATCC® accession No. PTA-4586); and monoclonal 5B10 (ATCC® accession No. PTA-4588).

Exemplary antigen-binding fragments are, Fab, Fab', $F(ab')_2$, Fv, Fd, dAb, and fragments containing complementarity determining region (CDR) fragments, single-chain antibodies (scFv), chimeric antibodies, diabodies and polypeptides that contain at least a portion of an immunoglobulin that is sufficient to confer specific antigen-binding to the polypeptide (e.g., immunoadhesins).

As used herein, Fd means a fragment that consists of the $V_H$ and $C_{H1}$ domains; Fv means a fragment that consists of the $V_L$ and $V_H$ domains of a single arm of an antibody; and dAb means a fragment that consists of a $V_H$ domain (Ward et al., Nature 341:544-546 (1989)). As used herein, single-chain antibody (scFv) means an antibody in which a $V_L$ region and a $V_H$ region are paired to form a monovalent molecule via a synthetic linker that enables them to be made as a single protein chain (Bird et al., Science 242:423-426 (1988) and Huston et al., Proc. Natl. Acad. Sci. USA 85:5879-5883 (1988)). As used herein, diabody means a bispecific antibody in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al., Proc. Natl. Acad. Sci. USA 90:6444-6448 (1993) and Poljak, R. J., et al., Structure 2:1121-1123 (1994)). As used herein, immunoadhesin that specifically binds an antigen of interest, means a molecule in which one or more CDRs may be incorporated, either covalently or noncovalently.

In some embodiments, a subunit polypeptide of a Nogo receptor-1 antibody is for use in the methods of the invention, wherein the subunit polypeptide is selected from the group consisting of: (a) a heavy chain or a variable region thereof; and (b) a light chain or a variable region thereof.

In some embodiments, the invention provides a nucleic acid encoding the heavy chain or the variable region thereof, or the light chain and the variable region thereof of a subunit polypeptide of a Nogo receptor-1 antibody for use in the methods of the invention.

In some embodiments, the invention provides a hypervariable region (CDR) of a Nogo receptor-1 antibody for use in the methods of the invention or a nucleic acid encoding a CDR.

Additional details regarding NgR1 antibodies and antigen binding fragments thereof for use in the methods of the invention and methods and materials for obtaining these molecules are described below and can also be found in U.S. Pat. No. 7,465,705 and U.S. Patent Appl. No. 2008/0274112, both of which are incorporated by reference in their entirety.

Immunization

Antibodies for use in the methods of the invention can be generated by immunization of a suitable host (e.g., vertebrates, including humans, mice, rats, sheep, goats, pigs, cattle, horses, reptiles, fishes, amphibians, and in eggs of birds, reptiles, and fish). Such antibodies may be polyclonal or monoclonal.

In some embodiments, the host is immunized with an immunogenic Nogo receptor-1 polypeptide for use in the methods of the invention. In other embodiments, the host is immunized with Nogo receptor-1 associated with the cell membrane of an intact or disrupted cell and antibodies for use in the methods of the invention are identified by binding to a Nogo receptor-1 polypeptide for use in the methods of the invention.

In some embodiments, the Nogo receptor-1 antigen is administered with an adjuvant to stimulate the immune response. Adjuvants often need to be administered in addition to antigen in order to elicit an immune response to the antigen. These adjuvants are usually insoluble or undegradable substances that promote nonspecific inflammation, with recruitment of mononuclear phagocytes at the site of immunization. Examples of adjuvants include, but are not limited to, Freund's adjuvant, RIBI (muramyl dipeptides), ISCOM (immunostimulating complexes) or fragments thereof.

For a review of methods for making antibodies, see e.g., Harlow and Lane, Antibodies, A Laboratory Manual (1988); Yelton, D. E. et al., Ann. Rev. of Biochem. 50:657-80. (1981); and Ausubel et al., Current Protocols in Molecular Biology (New York: John Wiley & Sons) (1989). Determination of immunoreactivity with an immunogenic Nogo receptor-1 polypeptide may be made by any of several methods well known in the art, including, e.g., immunoblot assay and ELISA.

Production of Antibodies and Antibody Producing Cell Lines

Monoclonal antibodies for use in the methods of the invention can made by standard procedures as described, e.g., in Harlow and Lane, Antibodies, A Laboratory Manual (1988), supra.

Briefly, at an appropriate period of time the animal is sacrificed and lymph node and/or splenic B-cells are immortalized by any one of several techniques that are well-known in the art, including but not limited to transformation, such as with EBV or fusion with an immortalized cell line, such as myeloma cells. Thereafter, the cells are clonally separated and the supernatants of each clone tested for production of an antibody specific for an immunogenic Nogo receptor-1 polypeptide. Methods of selecting, cloning and expanding hybridomas are well known in the art. Similarly, methods for identifying the nucleotide and amino acid sequence of the immunoglobulin genes are known in the art.

Other suitable techniques for producing an antibody for use in the methods of the invention involve in vitro exposure of lymphocytes to the Nogo receptor-1 or to an immunogenic polypeptide thereof, or alternatively, selection of libraries of antibodies in phage or similar vectors. See Huse et al., Science, 246:1275-81 (1989). Antibodies useful in the methods of the present invention may be employed with or without modification.

Antigens (in this case Nogo receptor-1 or an immunogenic polypeptide thereof) and antibodies can be labeled by joining, either covalently or non-covalently, a substance that provides for a detectable signal. Various labels and conjugation techniques are known in the art and can be employed in practicing the invention. Suitable labels include, but are not limited to, radionucleotides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced (see U.S. Pat. No. 4,816,567).

In some embodiments of the invention, an antibody for use in the methods of the invention has multiple binding specificities, such as a bifunctional antibody prepared by any one of a number of techniques known to those of skill in the art including the production of hybrid hybridomas, disulfide exchange, chemical cross-linking, addition of peptide linkers between two monoclonal antibodies, the introduction of two sets of immunoglobulin heavy and light chains into a particular cell line, and so forth (see below for more detailed discussion).

The antibodies for use in the methods of this invention may also be human monoclonal antibodies, for example those produced by immortalized human cells, by SCID-hu mice or other non-human animals capable of producing "human" antibodies.

Phage Display Libraries

Anti-Nogo receptor-1 antibodies for use in the methods of this invention can be isolated by screening a recombinant combinatorial antibody library. Exemplary combinatorial libraries are for binding to an immunogenic Nogo receptor-1 polypeptide, such as a scFv phage display library, prepared using $V_L$ and $V_H$ cDNAs prepared from mRNA derived from an animal immunized with an immunogenic Nogo receptor-1 polypeptide. Methodologies for preparing and screening such libraries are known in the art. There are commercially available methods and materials for generating phage display libraries (e.g., the Pharmacia Recombinant Phage Antibody System, catalog no. 27-9400-01; the Stratagene SurfZAP™ phage display kit, catalog no. 240612; and others from MorphoSys). There are also other methods and reagents that can be used in generating and screening antibody display libraries (see e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al., *Bio/Technology* 9:1370-1372 (1991); Hay et al., *Hum. Antibod. Hybridomas* 3:81-85; (1992) Huse et al., *Science* 246:1275-1281 (1989); McCafferty et al., *Nature* 348:552-554 (1990); Griffiths et al., *EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nucl. Acids Res.* 19:4133-4137 (1991); and Barbas et al., *Proc. Natl. Acad. Sci. USA* 88:7978-7982 (1991).

Following screening and isolation of an anti-Nogo receptor-1 antibody for use in the methods of the invention from a recombinant immunoglobulin display library, the nucleic acid encoding the selected antibody can be recovered from the display package (e.g., from the phage genome) and subcloned into other expression vectors by standard recombinant DNA techniques. If desired, the nucleic acid can be further manipulated to create other antibody forms for use in the methods of the invention, as described below. To express an antibody isolated by screening a combinatorial library, DNA encoding the antibody heavy chain and light chain or the variable regions thereof is cloned into a recombinant expression vector and introduced into a mammalian host cell, as described above.

Class Switching

Anti-Nogo receptor-1 antibodies for use in the methods of the invention can be of any isotype. An antibody of any desired isotype can be produced by class switching. For class switching, nucleic acids encoding $V_L$ or $V_H$, that do not include any nucleotide sequences encoding $C_L$ or $C_H$, are isolated using methods well known in the art. The nucleic acids encoding $V_L$ or $V_H$ are then operatively linked to a nucleotide sequence encoding a $C_L$ or $C_H$ from a desired class of immunoglobulin molecule. This may be achieved using a vector or nucleic acid that comprises a $C_L$ or $C_H$ chain, as described above. For example, an anti-Nogo receptor-1 antibody that was originally IgM may be class switched to an IgG. Further, the class switching may be used to convert one IgG subclass to another, e.g., from IgG1 to IgG2.

Mutated Antibodies

In other embodiments, antibodies or antigen-binding fragments for use in the methods of the invention may be mutated in the variable domains of the heavy and/or light chains to alter a binding property of the antibody. For example, a mutation may be made in one or more of the CDR regions to increase or decrease the $K_d$ of the antibody for Nogo receptor-1, to increase or decrease $K_{off}$, or to alter the binding specificity of the antibody. Techniques in site-directed mutagenesis are well known in the art. See e.g., Sambrook et al., *Molecular Cloning—A Laboratory Manual*, Cold Spring Harbor Laboratory Press (1989) and Ausubel et al., *Current Protocols in Molecular Biology* (New York: John Wiley & Sons) (1989). In a preferred embodiment, mutations are made at an amino acid residue that is known to be changed compared to germline in a variable region of an anti-Nogo receptor-1 antibody for use in the methods of the invention. In some embodiments, mutations are made at one or more amino acid residues that are known to be changed compared to the germline in a variable region of an anti-Nogo receptor-1 antibody. In another embodiment, a nucleic acid encoding an antibody heavy chain or light chain variable region is mutated in one or more of the framework regions. A mutation may be made in a framework region or constant domain to increase the half-life. A mutation in a framework region or constant domain also may be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions, or the constant domain in a single mutated antibody.

Fusion Antibodies and Immunoadhesins

In another embodiment, a fusion antibody or immunoadhesin for use in the methods of the invention may be made which comprises all or a portion of an anti-Nogo receptor-1 antibody for use in the methods of the invention linked to another polypeptide. In some embodiments, only the variable region of the anti-Nogo receptor-1 antibody is linked to the polypeptide. In other embodiments, the $V_H$ domain of an anti-Nogo receptor-1 antibody is linked to a first polypeptide, while the $V_L$ domain of the antibody is linked to a second polypeptide that associates with the first polypeptide in a manner that permits the $V_H$ and $V_L$ domains to interact with one another to form an antibody binding site. In other embodiments, the $V_H$ domain is separated from the $V_L$ domain by a linker that permits the $V_H$ and $V_L$ domains to interact with one another (see below under Single Chain Antibodies). The $V_H$-linker-$V_L$ antibody is then linked to a polypeptide of interest. The fusion antibody is useful to directing a polypeptide to a cell or tissue that expresses a Nogo receptor-1 ligand. The polypeptide of interest may be a therapeutic agent, such as a toxin, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

Single Chain Antibodies

The present invention includes the use of a single chain antibody (scFv) that binds a Nogo receptor-1 polypeptide in the methods of the invention. To produce the ScFv, $V_H$- and $V_L$-encoding DNA is operatively linked to DNA encoding a flexible linker, e.g., encoding the amino acid sequence (Gly$_4$-Ser)$_3$ (SEQ ID NO:1), such that the $V_H$ and $V_L$ sequences can be expressed as a contiguous single-chain protein, with the $V_L$ and $V_H$ regions joined by the flexible linker (see, e.g., Bird et al., *Science* 242:423-426 (1988); Huston et al., *Proc. Natl. Acad. Sci. USA* 85:5879-5883 (1988); McCafferty et al., *Nature* 348:552-554 (1990)). The single chain antibody may be monovalent, if only a single $V_H$ and $V_L$ are used, bivalent, if two $V_H$ and $V_L$ are used, or polyvalent, if more than two $V_H$ and VL are used.

Chimeric Antibodies

The methods of the present invention further include a bispecific antibody or antigen-binding fragment thereof in which one specificity is for a Nogo receptor-1 polypeptide. In one embodiment, a chimeric antibody for use in the methods of the invention can be generated that specifically binds to a Nogo receptor-1 polypeptide through one binding domain and to a second molecule through a second binding domain. The chimeric antibody can be produced through recombinant molecular biological techniques, or may be physically conjugated together. In addition, a single chain antibody containing more than one $V_H$ and $V_L$ for use in the methods of the invention may be generated that binds specifically to a polypeptide and to another molecule that is associated with attenuating myelin mediated growth cone collapse and inhibition of neurite outgrowth and sprouting. Such bispecific antibodies can be generated using techniques that are well known for example, Fanger et al., *Immunol Methods* 4: 72-81 (1994) and Wright and Harris, supra.

In some embodiments, the chimeric antibodies for use in the methods of the invention are prepared using one or more of the variable regions from an antibody. In another embodiment, the chimeric antibody is prepared using one or more CDR regions from said antibody.

Derivatized and Labeled Antibodies

An antibody or an antigen-binding fragment for use in the methods of the invention can be derivatized or linked to another molecule (e.g., another peptide or protein). In general, the antibody or antigen-binding fragment is derivatized such that binding to a polypeptide for use in the methods of the invention is not affected adversely by the derivatization or labeling. For example, an antibody or antibody portion for use in the methods of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate association of the antibody or antigen-binding fragment with another molecule (such as a streptavidin core region or a polyhistidine tag).

In some embodiments, a derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

In some embodiments, the derivatized antibody is a labeled antibody. Exemplary, detection agents with which an antibody or antibody portion may be derivatized are fluorescent compounds, including fluorescein, fluorescein isothiocyanate, rhodamine, 5-dimethylamine-1-napthalenesulfonyl chloride, phycoerythrin, lanthanide phosphors and the like. An antibody also may be labeled with enzymes that are useful for detection, such as horseradish peroxidase, β-galactosidase, luciferase, alkaline phosphatase, glucose oxidase and the like. In embodiments that are labeled with a detectable enzyme, the antibody is detected by adding additional reagents that the enzyme uses to produce a detectable reaction product. For example, horseradish peroxidase with hydrogen peroxide and diaminobenzidine. An antibody also may be labeled with biotin, and detected through indirect measurement of avidin or streptavidin binding. An antibody may also be labeled with a predetermined polypeptide epitopes recognized by a secondary reporter (e.g., leucine zipper pair sequences, binding sites for secondary antibodies, metal binding domains, epitope tags).

An anti-Nogo receptor-1 antibody or an antigen-fragment thereof also may be labeled with a radio-labeled amino acid. The radiolabel may be used for both diagnostic and therapeutic purposes. The radio-labeled anti-Nogo receptor-1 antibody may be used diagnostically, for example, for determining Nogo receptor-1 levels in a subject. Further, the radio-labeled anti-Nogo receptor-1 antibody may be used therapeutically for treating chronic spinal cord injury. Examples of labels for polypeptides include, but are not limited to, the following radioisotopes or radionucleotides—$^3$H, $^{14}$C, $^{15}$N, $^{35}$S, $^{90}$Y, $^{99}$Tc, $^{111}$In, $^{125}$I, $^{131}$I.

An anti-Nogo receptor-1 antibody or an antigen-fragment thereof for use in the methods of the invention may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

Characterization of Anti-Nogo Receptor-1 Antibodies

The class and subclass of anti-Nogo receptor-1 antibodies for use in the methods of the invention may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

Binding Affinity of Anti-Nogo Receptor-1 Antibody to Nogo Receptor-1

The binding affinity and dissociation rate of an anti-Nogo receptor-1 antibody for use in the methods of the invention to a Nogo receptor-1 polypeptide may be determined by any method known in the art. For example, the binding affinity can be measured by competitive ELISAs, RIAs, BIACORE™ or KINEXA™ technology. The dissociation rate also can be measured by BIACORET™ or KINEXA™ technology. The binding affinity and dissociation rate are measured by surface plasmon resonance using, e.g., a BIACORE™. The $K_d$ of 7E11 and 1H2 were determined to be $1 \times 10^{-7}$ M and $2 \times 10^{-8}$ M, respectively.

Inhibition of Nogo Receptor-1 Activity by Anti-Nogo Receptor-1 Antibody

In some embodiments, an anti-Nogo receptor-1 antibody or an antigen-binding fragment thereof for use in the methods of the invention inhibits the binding of Nogo receptor-1 to a ligand. The $IC_{50}$ of such inhibition can be measured by any method known in the art, e.g., by ELISA, RIA, or Functional Antagonism. In some embodiments, the $IC_{50}$ is between 0.1 and 500 nM. In some embodiments, the $IC_{50}$ is between 10 and 400 nM. In yet other embodiments, the antibody or portion thereof has an $IC_{50}$ of between 60 nM and 400 nM. The $IC_{50}$ of 7E11 and 1H2 were determined to be 400 nM and 60 nM, respectively, in a binding assay.

In some embodiments, the methods of the present invention also include use of NgR1-specific antibodies or antigen-binding fragments, variants, or derivatives which are antagonists of NgR1 activity. For example, the binding of certain NgR1 antibodies to NgR1 blocks NgR1-mediated inhibition of neuronal survival, neurite outgrowth, or axonal regeneration of central nervous system (CNS) neurons.

In other embodiments, the methods of the present invention include the use of an antibody, or antigen-binding fragment, variant, or derivative thereof which specifically or preferentially binds to at least one epitope of NgR1, where the epitope comprises, consists essentially of, or consists of at least about four to five amino acids of SEQ ID NO:10, at least seven, at least nine, or between at least about 15 to about 30 amino acids of SEQ ID NO:10. The amino acids of a given epitope of SEQ ID NO:10 as described may be, but need not be contiguous or linear. In certain embodiments, the at least one epitope of NgR1 comprises, consists essentially of, or consists of a non-linear epitope formed by the extracellular domain of NgR1 as expressed on the surface of a cell or as a soluble fragment, e.g., fused to an IgG Fc region. Thus, in certain embodiments the at least one epitope of NgR1 comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:10, where non-contiguous amino acids form an epitope through protein folding.

In other embodiments, the methods of the present invention include the use of an antibody, or antigen-binding fragment, variant, or derivative thereof which specifically or preferentially binds to at least one epitope of NgR1, where the epitope comprises, consists essentially of, or consists of, in addition to one, two, three, four, five, six or more contiguous or non-contiguous amino acids of SEQ ID NO:10 as described above, and an additional moiety which modifies the protein, e.g., a carbohydrate moiety may be included such that the NgR1 antibody binds with higher affinity to modified target protein than it does to an unmodified version of the protein. Alternatively, the NgR1 antibody does not bind the unmodified version of the target protein at all.

In certain embodiments, an antibody, or antigen-binding fragment, variant, or derivative thereof for use in the methods of the invention binds specifically to at least one epitope of NgR1 or fragment or variant described above, i.e., binds to such an epitope more readily than it would bind to an unrelated, or random epitope; binds preferentially to at least one epitope of NgR1 or fragment or variant described above, i.e., binds to such an epitope more readily than it would bind to a related, similar, homologous, or analogous epitope; competitively inhibits binding of a reference antibody which itself binds specifically or preferentially to a certain epitope of NgR1 or fragment or variant described above; or binds to at least one epitope of NgR1 or fragment or variant described above with an affinity characterized by a dissociation constant $K_d$ of less than about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M. In a particular aspect, the antibody or fragment thereof for use in the methods of the invention preferentially binds to a human NgR1 polypeptide or fragment thereof, relative to a murine NgR1 polypeptide or fragment thereof As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, an antibody, or antigen-binding fragment, variant, or derivative thereof for use in the methods of the invention binds NgR1 polypeptides or fragments or variants thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Alternatively, an antibody, or antigen-binding fragment, variant, or derivative thereof for use in the methods of the invention binds NgR1 polypeptides or fragments or variants thereof with an off rate (k(off)) of less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

In other embodiments, an antibody, or antigen-binding fragment, variant, or derivative thereof for use in the methods of the invention binds NgR1 polypeptides or fragments or variants thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. Alternatively, an antibody, or antigen-binding fragment, variant, or derivative thereof for use in the methods of the invention binds NgR1 polypeptides or fragments or variants thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

In one embodiment, an NgR1 antagonist for use in the methods of the invention is an antibody molecule, or immunospecific fragment thereof. Unless it is specifically noted, as used herein a "fragment thereof" in reference to an antibody refers to an immunospecific fragment, i.e., an antigen-specific fragment. In one embodiment, an antibody for use in the methods of the invention is a bispecific binding molecule, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific antibody has at least one binding domain specific for at least one epitope on NgR1. A bispecific antibody may be a tetravalent antibody that has two target binding domains specific for an epitope of NgR1 and two target binding domains specific for a second target. Thus, a tetravalent bispecific antibody may be bivalent for each specificity.

Certain embodiments of the present invention comprise administration of an NgR1 antagonist antibody, or immunospecific fragment thereof, in which at least a fraction of one or more of the constant region domains has been deleted or otherwise altered so as to provide desired biochemical characteristics such as reduced effector functions, the ability to non-covalently dimerize, increased ability to localize at the site of a injury, reduced serum half-life, or increased serum half-life when compared with a whole, unaltered antibody of approximately the same immunogenicity. For example, certain antibodies for use in the treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain NgR1 antagonist antibodies or immunospecific fragments thereof for use in the therapeutic methods described herein, the Fc portion may be mutated to alter, e.g., increase, decrease or modulate effector function using techniques known in the art. For example, the deletion or inactivation (through point mutations or other means) of a constant region domain may reduce or alter Fc receptor binding of the circulating modified antibody thereby increasing site-specific injury localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as site-specific injury localization, biodistribution and serum half-life, may easily be measured and quantified using well know immunological techniques without undue experimentation.

Modified forms of antibodies or immunospecific fragments thereof for use in the diagnostic and therapeutic methods disclosed herein can be made from whole precursor or parent antibodies using techniques known in the art. Exemplary techniques are discussed in more detail herein.

In certain embodiments both the variable and constant regions of NgR1 antagonist antibodies or immunospecific fragments thereof for use in the treatment methods disclosed herein are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems, as described in more detail elsewhere herein.

NgR1 antagonist antibodies or immunospecific fragments thereof for use in the methods disclosed herein can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

NgR1 antagonist antibodies or immunospecific fragments thereof for use in the methods disclosed herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In preferred embodiments, an NgR1 antagonist antibody or immunospecific fragment thereof for use in the methods disclosed herein will not elicit a deleterious immune response in the animal to be treated, e.g., in a human. In one embodiment, NgR1 antagonist antibodies or immunospecific fragments thereof for use in the methods disclosed herein may be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, $V_H$ and $V_L$ sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., NgR1 antagonist antibodies or immunospecific fragments thereof for use in the methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

NgR1 antagonist antibodies or fragments thereof for use in the methods of the present invention may be generated by any suitable method known in the art. Polyclonal antibodies can be produced by various procedures well known in the art. For example, an NgR1 immunospecific fragment can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Using art recognized protocols, in one example, antibodies are raised in mammals by multiple subcutaneous or intraperitoneal injections of the relevant antigen (e.g., purified NgR1 antigens or cells or cellular extracts comprising such antigens) and an adjuvant. This immunization typically elicits an immune response that comprises production of antigen-reactive antibodies from activated splenocytes or lymphocytes. While the resulting antibodies for use in the methods of the invention may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, Monoclonal Antibodies: Principles and Practice, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

Those skilled in the art will also appreciate that DNA encoding antibodies or antibody fragments (e.g., antigen binding sites) for use in the methods of the invention may also be derived from antibody phage libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243: 211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. In particular, DNA sequences encoding $V_H$ and $V_L$ regions are amplified from animal cDNA libraries (e.g., human or murine cDNA libraries of lymphoid tissues) or synthetic cDNA libraries. In certain embodiments, the DNA encoding the $V_H$ and $V_L$ regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the $V_H$ or $V_L$ regions are usually recombinantly fused to either the phage gene III or gene VIII. Phage expressing an antigen binding domain that binds to an antigen of interest (i.e., a NgR1 polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies for use in the methods of the invention include those described in U.S. Pat. Nos. 4,946,778 and 5,258,498; Huston et al., *Methods in Enzymology* 203: 46-88 (1991); Shu et al., *PNAS* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties. Humanized antibodies are antibody molecules from a non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5): 489-498 (1991); Studnicka et al., *Protein Engineering* 7(6): 805-814 (1994); Roguska. et al., *PNAS* 91:969-973 (1994)), and chain shuffling (U.S. Pat. No. 5,565,332).

Completely human antibodies are particularly desirable for therapeutic treatment of human patients. Human antibodies for use in the methods of the invention can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies for use in the methods of the invention can also be produced using transgenic mice which are incapable of expressing functional, endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/Technology 12:899-903 (1988); see also, U.S. Pat. No. 5,565,332).

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278:457-479 (1998) for a listing of human framework regions). Preferably, the polynucleotide generated by the combination of the framework regions and CDRs encodes an antibody that specifically binds to at least one epitope of a desired polypeptide, e.g., NgR1. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, Science 242:423-442 (1988); Huston et al., Proc. Natl. Acad. Sci. USA 85:5879-5883 (1988); and Ward et al., Nature 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in E. coli may also be used (Skerra et al., Science 242:1038-1041 (1988)).

NgR1 antagonist antibodies for use in the methods of the invention may also be human or substantially human antibodies generated in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, Biotechnology 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibodies for use in the methods disclosed herein can be produced by any method known in the art for the synthesis of antibodies, in particular, by chemical synthesis or preferably, by recombinant expression techniques as described herein.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic at any point during the isolation process or subsequent analysis.

Recombinant expression of an antibody, or fragment, derivative or analog thereof, e.g., a heavy or light chain of an antibody which is an NgR1 antagonist, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule for use in the methods of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Proc. Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260: 926-932 (1993); and Morgan and Anderson, *Ann. Rev. Biochem.* 62:191-217 (1993);, *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

Once an antibody molecule for use in the methods of the invention of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002/0123057 A1.

In one embodiment, a binding molecule or antigen binding molecule for use in the methods of the invention comprises a synthetic constant region wherein one or more domains are partially or entirely deleted ("domain-deleted antibodies"). In certain embodiments compatible modified antibodies will comprise domain deleted constructs or variants wherein the entire $C_H2$ domain has been removed ($\Delta C_H2$ constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody.

In certain embodiments, modified antibodies for use in the methods disclosed herein are minibodies. Minibodies can be made using methods described in the art (see, e.g., U.S. Pat. No. 5,837,821 or WO 94/09817A1).

In another embodiment, modified antibodies for use in the methods disclosed herein are CH2 domain deleted antibodies which are known in the art. Domain deleted constructs can be derived using a vector encoding an IgG1 human constant domain (see, e.g., WO 02/060955A2 and WO 02/096948A2). This exemplary vector was engineered to delete the $C_H2$ domain and provide a synthetic vector expressing a domain deleted IgG1 constant region.

In one embodiment, a NgR1 antagonist antibody or fragment thereof for use in the treatment methods disclosed herein comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The methods of the present invention also provides the use of antibodies that comprise, consist essentially of, or consist of, variants (including derivatives) of antibody molecules (e.g., the $V_H$ regions and/or $V_L$ regions) described herein, which antibodies or fragments thereof immunospecifically bind to a NgR1 polypeptide. Standard techniques known to those of skill in the art can be used to introduce mutations in the nucleotide sequence encoding a binding molecule, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein can be determined using techniques described herein or by routinely modifying techniques known in the art.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Uses of the antibodies in the methods of the present invention are described below.

Nucleic Acid Molecules

The present invention provides a nucleic acid that encodes a polypeptide for use in the methods of the invention. In some embodiments, the nucleic acid encodes a polypeptide selected from the group consisting of amino acid residues 26-344 of Nogo receptor-1 as shown in SEQ ID NOs: 13 and 15 or amino acid residues 27-344 of Nogo receptor-1 as shown in SEQ ID NO:15. In some embodiments, the nucleic acid molecule encodes a polypeptide selected from the group consisting of amino acid residues 26-310 of Nogo receptor-1 as shown in SEQ ID NOs: 14 and 16 or amino acid residues 27-310 of Nogo receptor-1 as shown in SEQ ID NO:16. As used herein, "nucleic acid" means genomic DNA, cDNA, mRNA and antisense molecules, as well as nucleic acids based on alternative backbones or including alternative bases whether derived from natural sources or synthesized. In some embodiments, the nucleic acid further comprises a transcriptional promoter and optionally a signal sequence each of which is operably linked to the nucleotide sequence encoding the polypeptides for use in the methods of the invention.

In some embodiments, a nucleic acid encoding a Nogo receptor-1 fusion protein is provided for use in the methods of the invention, including a fusion protein comprising a polypeptide selected from the group consisting of amino acid residues 26-344 of Nogo receptor-1 as shown in SEQ ID NOs: 13 and 15 or amino acid residues 27-344 of SEQ ID NO:15 and amino acid residues 26-310 of Nogo receptor-1 as shown in SEQ ID NOs: 14 and 16 or amino acid residues 27-310 of SEQ ID NO:16. In some embodiments, the nucleic acid encoding a Nogo receptor-1 fusion protein further comprises a transcriptional promoter and optionally a signal sequence. In some embodiments, the nucleotide sequence further encodes an immunoglobulin constant region. In some embodiments, the immunoglobulin constant region is a heavy chain constant region. In some embodiments, the nucleotide sequence further encodes an immunoglobulin heavy chain constant region joined to a hinge region. In some embodiments the nucleic acid further encodes Fc. In some embodiments, the Nogo receptor-1 fusion proteins comprise an Fc fragment.

The methods of the invention also include the use of polynucleotides that hybridize under moderately stringent or high stringency conditions to the noncoding strand, or complement, of a polynucleotide that encodes any one of the polypeptides for use in the methods of the invention. Stringent conditions are known to those skilled in the art and can be found in CURRENT PROTOCOLS IN MOLECULAR BIOLOGY, John Wiley & Sons, N.Y. (1989), 6.3.1-6.3.6.

The human Nogo receptor-1 polynucleotide is shown below as SEQ ID NO:27.

Full-Length Human Nogo receptor-1 is encoded by nucleotide 166 to nucleotide 1587 of SEQ ID NO:27:

```
agcccagcca gagccgggcg gagcggagcg cgccgagcct
cgtcccgcgg ccgggccggg gccgggccgt agcggcggcg
cctggatgcg gacccggccg cggggagacg ggcgcccgcc
ccgaaacgac tttcagtccc cgacgcgccc cgcccaaccc
ctacgatgaa gagggcgtcc gctggaggga gccggctgct
ggcatgggtg ctgtggctgc aggcctggca ggtggcagcc
ccatgcccag gtgcctgcgt atgctacaat gagcccaagg
tgacgacaag ctgcccccag cagggcctgc aggctgtgcc
cgtgggcatc cctgctgcca gccagcgcat cttcctgcac
ggcaaccgca tctcgcatgt gccagctgcc agcttccgtg
cctgccgcaa cctcaccatc ctgtggctgc actcgaatgt
gctgcccga attgatgcgg ctgccttcac tggcctggcc
ctcctggagc agctggacct cagcgataat gcacagctcc
ggtctgtgga ccctgccaca ttccacggcc tgggccgcct
acacacgctg cacctggacc gctgcgcct gcaggagctg
ggcccggggc tgttccgcgg cctggctgcc ctgcagtacc
tctacctgca ggacaacgcg ctgcaggcac tgcctgatga
caccttccgc gacctgggca acctcacaca cctcttcctg
cacggcaacc gcatctccag cgtgcccgag cgcgccttcc
gtgggctgca cagcctcgac cgtctcctac tgcaccagaa
```

-continued
```
ccgcgtggcc catgtgcacc cgcatgcctt ccgtgacctt
ggccgcctca tgacactcta tctgtttgcc aacaatctat
cagcgctgcc cactgaggcc ctggcccccc tgcgtgccct
gcagtacctg aggctcaacg acaacccctg ggtgtgtgac
tgccgggcac gcccactctg ggcctggctg cagaagttcc
gcggctcctc ctccgaggtg ccctgcagcc tcccgcaacg
cctggctggc cgtgacctca aacgcctagc tgccaatgac
ctgcagggct gcgctgtggc caccggccct taccatccca
tctggaccgg cagggccacc gatgaggagc cgctggggct
tcccaagtgc tgccagccag atgccgctga caaggcctca
gtactggagc ctggaagacc agcttcggca ggcaatgcgc
tgaagggacg cgtgccgccc ggtgacagcc cgccgggcaa
cggctctggc ccacggcaca tcaatgactc accctttggg
actctgcctg gctctgctga gcccccgctc actgcagtgc
ggcccgaggg ctccgagcca ccagggttcc ccacctcggg
ccctcgccgg aggccaggct gttcacgcaa gaaccgcacc
cgcagccact gccgtctggg ccaggcaggc agcggggtg
gcgggactgg tgactcagaa ggctcaggtg ccctacccag
cctcacctgc agcctcaccc cctgggcct ggcgctggtg
ctgtggacag tgcttgggcc ctgctgaccc ccagcggaca
caagagcgtg ctcagcagcc aggtgtgtgt acatacgggg
tctctctcca cgccgccaag ccagccgggc ggccgacccg
tggggcaggc caggccaggt cctccctgat ggacgcctg
```

The rat Nogo receptor-1 polynucleotide is shown below as SEQ ID NO:28 and is accession number NM_053613 in Genbank.

```
atgaagaggg cgtcctccgg aggaagccgg ctgccgacat
gggtgttatg gctacaggcc tggagggtag caacgccctg
ccctggtgcc tgtgtgtgct acaatgagcc caaggtcaca
acaagccgcc cccagcaggg cctgcaggct gtaccgctg
gcatcccagc ctccagccag agaatcttcc tgcacggcaa
ccgaatctct tacgtgccag ccgccagctt ccagtcatgc
cggaatctca ccatcctgtg gctgcactca aatgcgctgg
ccgggattga tgccgcggcc ttcactggtc tgaccctcct
ggagcaacta gatcttagtg acaatgcaca gctccgtgtc
gtggaccca ccacgttccg tggcctgggc cacctgcaca
cgctgcacct agaccgatgc ggcctgcagg agctggggcc
tggcctattc cgtgggctgg cagctctgca gtacctctac
ctacaagaca acaacctgca ggcacttccc gacaacacct
tccgagacct gggcaacctc acgcatctct ttctgcatgg
caaccgtatc cccagtgttc ctgagcacgc tttccgtggc
```

```
ttgcacagtc ttgaccgtct cctcttgcac cagaaccatg tggctcgtgt gcacccacat gccttccggg accttggccg actcatgacc ctctacctgt ttgccaacaa cctctccatg ctccccgcag aggtcctagt gcccctgagg tctctgcagt acctgcgact caatgacaac ccctgggtgt gtgactgcag ggcacgtccg ctctgggcct ggctgcagaa gttccaggt tcctcatccg gggtgcccag caacctaccc caacgcctgg caggccgtga tctgaagcgc ctggctacca gtgacttaga gggttgtgct gtggcttcgg ggcccttccg tcccttccag accaatcagc tcactgatga ggagctgctg ggcctcccca agtgctgcca gccggatgct gcagacaagg cctcagtact ggaacccggg aggccggcgt ctgttggaaa tgcactcaag ggacgtgtgc ctcccggtga cactccacca ggcaatggct caggcccacg gcacatcaat gactctccat ttgggacttt gcccggctct gcagagcccc cactgactgc cctgcggcct gggggttccg agccccggg actgcccacc acgggccccc gcaggaggcc aggttgttcc agaaagaacc gcaccgtag ccactgccgt ctgggccagg caggaagtgg gagcagtgga actggggatg cagaaggttc ggggccctg cctgccctgg cctgcagcct tgctcctctg ggccttgcac tggtactttg gacagtgctt gggccctgct ga
```

The mouse Nogo receptor-1 polynucleotide is shown below as SEQ ID NO:29 and is accession number NM_022982 in Genbank.

```
agccgcagcc cgcgagccca gcccggcccg gtagagcgga gcgccggagc ctcgtcccgc ggccgggccg ggaccgggcc ggagcagcgg cgcctggatg cggacccggc cgcgcgcaga cgggcgcccg ccccgaagcc gcttccagtg cccgacgcgc cccgctcgac cccgaagatg aagagggcgt cctccggagg aagcaggctg ctggcatggg tgttatggct acaggcctgg agggtagcaa caccatgccc tggtgcttgt gtgtgctaca atgagcccaa ggtaacaaca agctgccccc agcagggtct gcaggctgtg cccactggca tcccagcctc tagccagcga atcttcctgc atggcaaccg aatctctcac gtgccagctg cgagcttcca gtcatgccga aatctcacta tcctgtggct gcactctaat gcgctggctc ggatcgatgc tgctgccttc actggtctga ccctcctgga gcaactagat cttagtgata atgcacagct tcatgtcgtg gaccctacca cgttccacgg cctgggccac ctgcacacac tgcacctaga ccgatgtgc ctgcgggagc tgggtccgg cctattccgt ggactagcag ctctgcagta cctctaccta caagacaaca atctgcaggc
```

```
actccctgac aacaccttc gagacctggg caacctcacg catctctttc tgcatggcaa ccgtatcccc agtgtgcctg agcacgcttt ccgtggcctg cacagtcttg accgcctcct cttgcaccag aaccatgtgg ctcgtgtgca cccacatgcc ttccgggacc ttggccgcct catgaccctc tacctgtttg ccaacaacct ctccatgctg cctgcagagg tcctaatgcc cctgaggtct ctgcagtacc tgcgactcaa tgacaacccc tgggtgtgtg actgccgggc acgtccactc tgggcctggc tgcagaagtt ccgaggttcc tcatcagagg tgccctgcaa cctgccccaa cgcctggcag accgtgatct taagcgcctc gctgccagtg acctagaggg ctgtgctgtg gcttcaggac ccttccgtcc catccagacc agtcagctca ctgatgagga gctgctgagc ctccccaagt gctgccagcc agatgctgca gacaaagcct cagtactgga acccgggagg ccagcttctg ccggaaacgc cctcaaggga cgtgtgcctc ccggtgacac tccaccaggc aatggctcag gccctcggca catcaatgac tctccatttg aactttgcc cagctctgca gagccccac tgactgccct gcggcctggg ggttccgagc caccaggact tccaccact ggtccccgca ggaggccagg ttgttcccgg aagaatcgca cccgcagcca ctgccgtctg ggccaggcgg gaagtgggc cagtggaaca ggggacgcag agggttcagg ggctctgcct gctctggcct gcagccttgc tcctctgggc cttgcactgg tactttggac agtgcttggg ccctgctgac cagccaccag ccaccaggtg tgtgtacata tggggtctcc ctccacgccg ccagccagag ccagggacag gctctgaggg gcaggccagg ccctccctga cagatgcctc cccaccagcc caccccatc tccaccccat catgtttaca gggttccggg ggtggcgttt gttccagaac gccacctccc acccggatcg cggtatatag agatatgaat tttattttac ttgtgtaaaa tatcggatga cgtggaataa agagctcttt tcttaaaaaa aaaaaaaaaa aa
```

NgR1 Polynucleotide Antagonists

Specific embodiments comprise NgR1 polynucleotide antagonists for use in the methods of the invention which prevent expression of NgR1 (knockdown). NgR1 polynucleotide antagonists include, but are not limited to antisense molecules, ribozymes, siRNA, shRNA and RNAi. Typically, such binding molecules are separately administered to the animal (see, for example, O'Connor, J. Neurochem. 56:560 (1991), but such binding molecules may also be expressed in vivo from polynucleotides taken up by a host cell and expressed in vivo. See also Oligodeoxynucleotides as Antisense Inhibitors of Gene Expression, CRC Press, Boca Raton, Fla. (1988).

Expression of the NgR gene can, in some embodiments, be inhibited using RNA interference ("RNAi"). RNAi refers to the expression of an RNA which interferes with the expression of the targeted mRNA. RNAi is a phenomenon in which the introduction of double-stranded RNA (dsRNA) into a cell causes degradation of the homologous mRNA. First discovered in the nematode *Caenorhabditis elegans*, RNAi has since been found to operate in a wide range of organisms. An "RNAi nucleic acid" as used herein is a nucleic acid sequence generally shorter than 50 nucleotides in length, that causes gene silencing at the mRNA level.

For example, in mammalian cells, introduction of long dsRNA (>30 nucleotides) can initiate a potent antiviral response, exemplified by nonspecific inhibition of protein synthesis and RNA degradation. RNA interference provides a mechanism of gene silencing at the mRNA level. In recent years, RNAi has become an endogenous and potent gene-specific silencing technique that uses double-stranded RNAs (dsRNA) to mark a particular transcript for degradation in vivo. It also offers an efficient and broadly applicable approach for gene knock-out. In addition, RNAi technology can be used for therapeutic purposes. For example, RNAi targeting Fas-mediated apoptosis has been shown to protect mice from fulminant hepatitis. RNAi technology has been disclosed in numerous publications, such as U.S. Pat. Nos. 5,919,619, 6,506,559 and PCT Publication Nos. WO99/14346, WO01/70949, WO01/36646, WO00/63364, WO00/44895, WO01/75164, WO01/92513, WO01/68836 and WO01/29058.

Specifically, the RNAi silences a targeted gene via interacting with the specific mRNA (e.g. NgR1) through a siRNA (short interfering RNA). The dsRNA complex is then targeted for degradation by the cell. Additional RNAi molecules include Short hairpin RNA (shRNA); also short interfering hairpin. The shRNA molecule contains sense and antisense sequences from a target gene connected by a loop. The shRNA is transported from the nucleus into the cytoplasm, it is degraded along with the mRNA. Pol III or U6 promoters can be used to express RNAs for RNAi. A sequence capable of inhibiting gene expression by RNA interference can have any length. For instance, the sequence can have at least 10, 15, 20, 25, 30, 35, 40, 45, 50, 100 or more consecutive nucleotides. The sequence can be dsRNA or any other type of polynucleotide, provided that the sequence can form a functional silencing complex to degrade the target mRNA transcript.

RNAi is mediated by double stranded RNA (dsRNA) molecules that have sequence-specific homology to their "target" mRNAs (Caplen et al., *Proc Natl Acad Sci USA* 98:9742-9747, 2001). Biochemical studies in Drosophila cell-free lysates indicates that the mediators of RNA-dependent gene silencing are 18-25 nucleotide "small interfering" RNA duplexes (siRNAs). Accordingly, siRNA molecules are advantageously for use in the methods of the present invention. siRNAs can be produced endogenously by degradation of longer dsRNA molecules by an RNase III-related nuclease called Dicer. (Bernstein et al., *Nature* 409:363-366, 2001). siRNAs can also be introduced into a cell exogenously, or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing. Without wishing to be bound by any particular theory, it is believed that a RISC is guided to a target mRNA, where the siRNA duplex interacts sequence-specifically to mediate cleavage in a catalytic fashion (Bernstein et al., *Nature* 409: 363-366, 2001; Boutla et al., *Curr Biol* 11:1776-1780, 2001).

Cleavage of the mRNA takes place near the middle of the region bound by the siRNA strand. This sequence specific mRNA degradation results in gene silencing.

RNAi has been used to analyze gene function and to identify essential genes in mammalian cells (Elbashir et al., *Methods* 26:199-213, 2002; Harborth et al., *J Cell Sci* 114:4557-4565, 2001), including by way of non-limiting example neurons (Krichevsky et al., *Proc Natl Acad Sci USA* 99:11926-11929, 2002). RNAi is also being evaluated for therapeutic modalities, such as inhibiting or blocking the infection, replication and/or growth of viruses, including without limitation poliovirus (Gitlin et al., *Nature* 418:379-380, 2002) and HIV (Capodici et al., *J Immunol* 169:5196-5201, 2002), and reducing expression of oncogenes (e.g., the bcr-abl gene; Scherr et al., *Blood* September 26 epub ahead of print, 2002). RNAi has been used to modulate gene expression in mammalian (mouse) and amphibian (*Xenopus*) embryos (respectively, Calegari et al., *Proc Natl Acad Sci USA* 99:14236-14240, 2002; and Zhou, et al., *Nucleic Acids Res* 30:1664-1669, 2002), and in postnatal mice (Lewis et al., *Nat Genet* 32:107-108, 2002), and to reduce transgene expression in adult transgenic mice (McCaffrey et al., *Nature* 418:38-39, 2002). Methods have been described for determining the efficacy and specificity of siRNAs in cell culture and in vivo (see, e.g., Bertrand et al., *Biochem Biophys Res Commun* 296:1000-1004, 2002; Lassus et al., *Sci STKE* 2002 (147):PL13, 2002; and Leirdal et al., *Biochem Biophys Res Commun* 295:744-748, 2002).

Molecules that mediate RNAi, including without limitation siRNA, can be produced in vitro by chemical synthesis (Hohjoh, *FEBS Lett* 521:195-199, 2002), hydrolysis of dsRNA (Yang et al., *Proc Natl Acad Sci USA* 99:9942-9947, 2002), by in vitro transcription with T7 RNA polymerase (Donzeet et al., *Nucleic Acids Res* 30:e46, 2002; Yu et al., *Proc Natl Acad Sci USA* 99:6047-6052, 2002), and by hydrolysis of double-stranded RNA using a nuclease such as *E. coli* RNase III (Yang et al., *Proc Natl Acad Sci USA* 99:9942-9947, 2002).

siRNA molecules may also be formed by annealing two oligonucleotides to each other, typically have the following general structure, which includes both double-stranded and single-stranded portions:

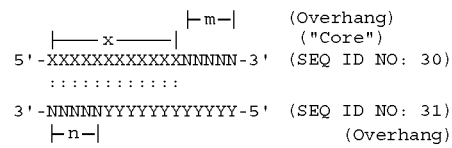

Wherein N, X and Y are nucleotides; X hydrogen bonds to Y; ":" signifies a hydrogen bond between two bases; x is a natural integer having a value between 1 and about 100; and m and n are whole integers having, independently, values between 0 and about 100. In some embodiments, N, X and Y are independently A, G, C, and T or U. Non-naturally occurring bases and nucleotides can be present, particularly in the case of synthetic siRNA (i.e., the product of annealing two oligonucleotides). The double-stranded central section is called the "core" and has base pairs (bp) as units of measurement; the single-stranded portions are overhangs, having nucleotides (nt) as units of measurement. The overhangs shown are 3' overhangs, but molecules with 5' overhangs are also within the scope of the invention. Also within the scope of the invention are siRNA molecules with no overhangs (i.e., m=0 and n=0), and those having an overhang on one side of the core but not the other (e.g., m=0 and n>1, or vice-versa).

Initially, RNAi technology did not appear to be readily applicable to mammalian systems. This is because, in mammals, dsRNA activates dsRNA-activated protein kinase (PKR) resulting in an apoptotic cascade and cell death (Der et al., *Proc. Natl. Acad. Sci. USA* 94:3279-3283, 1997). In addition, it has long been known that dsRNA activates the interferon cascade in mammalian cells, which can also lead to altered cell physiology (Colby et al., *Annu. Rev. Microbiol.* 25:333, 1971; Kleinschmidt et al., *Annu. Rev. Biochem.* 41:517, 1972; Lampson et al., *Proc. Natl. Acad. Sci. USA* 58:L782, 1967; Lomniczi et al., *J. Gen. Virol.* 8:55, 1970; and Younger et al., *J. Bacteriol.* 92:862, 1966). However, dsRNA-mediated activation of the PKR and interferon cascades requires dsRNA longer than about 30 base pairs. In contrast, dsRNA less than 30 base pairs in length has been demonstrated to cause RNAi in mammalian cells (Caplen et al., *Proc. Natl. Acad. Sci. USA* 98:9742-9747, 2001). Thus, it is expected that undesirable, non-specific effects associated with longer dsRNA molecules can be avoided by preparing short RNA that is substantially free from longer dsRNAs.

References regarding siRNA: Bernstein et al., *Nature* 409: 363-366, 2001; Boutla et al., *Curr Biol* 11:1776-1780, 2001; Cullen, *Nat Immunol.* 3:597-599, 2002; Caplen et al., *Proc Natl Acad Sci USA* 98:9742-9747, 2001; Hamilton et al., *Science* 286:950-952, 1999; Nagase et al., *DNA Res.* 6:63-70, 1999; Napoli et al., *Plant Cell* 2:279-289, 1990; Nicholson et al., *Mamm. Genome* 13:67-73, 2002; Parrish et al., *Mol Cell* 6:1077-1087, 2000; Romano et al., *Mol Microbiol* 6:3343-3353, 1992; Tabara et al., *Cell* 99:123-132, 1999; and Tuschl, *Chembiochem.* 2:239-245, 2001.

Paddison et al. (*Genes & Dev.* 16:948-958, 2002) have used small RNA molecules folded into hairpins as a means to effect RNAi. Accordingly, such short hairpin RNA (shRNA) molecules are also advantageously for use in the methods of the invention. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the dsRNA products of the DICER RNase and, in any event, have the same capacity for inhibiting expression of a specific gene.

Chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., *Nature* 344:565 (1990); Pieken et al., *Science* 253:314 (1991); Usman and Cedergren, *Trends in Biochem. Sci.* 17:334 (1992); Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein). All of the above references describe various chemical modifications that can be made to the base, phosphate, and/or sugar moieties of the nucleic acid molecules described herein. Modifications that enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-O-allyl, 2'-H, modifications (for a review see Usman and Cedergren, *TIBS.* 17:34 (1992); Usman et al., *Nucleic Acids Symp. Ser.* 31:163 (1994); Burgin et al., *Biochemistry* 35:14090 (1996)). Sugar modification of nucleic acid molecules have been extensively described in the art (see Eckstein et al., International Publication PCT No. WO 92/07065; Perrault et al., *Nature* 344: 565-568 (1990); Pieken et al., *Science* 253: 314-317 (1991); Usman and Cedergren, *Trends in Biochem. Sci.* 17: 334-339 (1992); Usman et al., International Publication PCT No. WO 93/15187; Sproat, U.S. Pat. No. 5,334,711 and Beigelman et al., *J. Biol. Chem.* 270:25702 (1995); Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Karpeisky et al., 1998, *Tetrahedron Lett.* 39:1131 (1998); Earnshaw and Gait, *Biopolymers (Nucleic Acid Sciences)* 48:39-55 (1998); Verma and Eckstein, *Annu. Rev. Biochem.* 67:99-134 (1998); and Burlina et al., *Bioorg. Med. Chem.* 5:1999-2010 (1997); all of the references are hereby incorporated in their totality by reference herein). Such publications describe general methods and strategies to determine the location of incorporation of sugar, base and/or phosphate modifications and the like into nucleic acid molecules without modulating catalysis, and are incorporated by reference herein. In view of such teachings, similar modifications can be used as described herein to modify the siRNA nucleic acid molecules for use in the methods of the invention so long as the ability of siRNA to promote RNAi in cells is not significantly inhibited.

The methods of the invention feature the use of modified siRNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, Nucleic Acid Analogues: Synthesis and Properties, in Modern Synthetic Methods, VCH, 331-417 (1995), and Mesmaeker et al., Novel Backbone Replacements for Oligonucleotides, in Carbohydrate Modifications in Antisense Research, ACS, 24-39 (1994).

While chemical modification of oligonucleotide internucleotide linkages with phosphorothioate, phosphorothioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

siRNA molecules having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, therapeutic nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA and DNA (Wincott et al., *Nucleic Acids Res.* 23:2677 (1995); Caruthers et al., *Methods in Enzymology* 211:3-19 (1992) (incorporated by reference herein)) have expanded the ability to modify nucleic acid molecules by introducing nucleotide modifications to enhance their nuclease stability, as described above.

Polynucleotides for use in the methods of the present invention can include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see, e.g., Lin and Matteucci, J. Am. Chem. Soc. 120: 8531-8532 (1998). A single G-clamp analog substitution within an oligonucleotide can result in substantially enhanced helical thermal stability and mismatch discrimination when hybridized to complementary oligonucleotides. The inclusion of such nucleotides in polynucleotides for use in the methods of the invention results in both enhanced affinity and specificity to nucleic acid targets, complementary sequences, or template strands. Polynucleotides of the present invention can also include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., International PCT Publication No. WO 00/66604 and WO 99/14226).

The present invention also features conjugates and/or complexes of siRNA molecules for use in the methods of the invention. Such conjugates and/or complexes can be used to facilitate delivery of siRNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. The present invention encompasses the use of novel conjugates and complexes for the delivery of molecules in the methods of the invention, including, but not limited to, small molecules, lipids, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the invention into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

Therapeutic polynucleotides (e.g., siRNA molecules) delivered exogenously optimally are stable within cells until reverse transcription of the RNA has been modulated long enough to reduce the levels of the RNA transcript. The nucleic acid molecules are resistant to nucleases in order to function as effective intracellular therapeutic agents. Improvements in the chemical synthesis of nucleic acid molecules described herein and in the art have expanded the ability to modify nucleic acid molecules by introducing nucleotide modifications to enhance their nuclease stability as described above.

The present invention also provides for the use of siRNA molecules having chemical modifications that maintain or enhance enzymatic activity of proteins involved in RNAi. Such nucleic acids are also generally more resistant to nucleases than unmodified nucleic acids. Thus, in vitro and/or in vivo the activity should not be significantly lowered.

Use of the polynucleotide-based molecules of the invention will lead to better treatment of the disease progression by affording the possibility of combination therapies (e.g., multiple siRNA molecules targeted to different genes; nucleic acid molecules coupled with known small molecule modulators; or intermittent treatment with combinations of molecules, including different motifs and/or other chemical or biological molecules). The treatment of subjects with siRNA molecules can also include combinations of different types of nucleic acid molecules, such as enzymatic nucleic acid molecules (ribozymes), allozymes, antisense, 2,5-A oligoadenylate, decoys, aptamers, etc.

In another aspect, an siRNA molecule for use in the methods of the invention can comprise one or more 5' and/or a 3'-cap structures, for example on only the sense siRNA strand, antisense siRNA strand, or both siRNA strands. By "cap structure" is meant chemical modifications, which have been incorporated at either terminus of the oligonucleotide (see, for example, Adamic et al., U.S. Pat. No. 5,998,203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples: the 5'-cap is selected from the group comprising inverted abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

The 3'-cap can be selected from a group comprising, 4',5'-methylene nucleotide; 1-(beta-D-erythrofuranosyl)nucleotide; 4'-thio nucleotide, carbocyclic nucleotide; 5'-aminoalkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, Tetrahedron 49:1925 (1993); incorporated by reference herein).

Various modifications to nucleic acid siRNA structure can be made to enhance the utility of these molecules for use in the methods of the invention. Such modifications will enhance shelf-life, half-life in vitro, stability, and ease of introduction of such oligonucleotides to the target site, e.g., to enhance penetration of cellular membranes, and confer the ability to recognize and bind to targeted cells.

Antisense technology can be used to control gene expression through antisense DNA or RNA, or through triple-helix formation. Antisense techniques are discussed for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes NgR1 may be used to design an antisense RNA oligonucleotide of from about 10 to 40 base pairs in length. A DNA oligonucleotide is designed to be complementary to a region of the gene involved in transcription thereby preventing transcription and the production of the target protein. The antisense RNA oligonucleotide hybridizes to the mRNA in vivo and blocks translation of the mRNA molecule into the target polypeptide.

In one embodiment, antisense nucleic acids specific for the NgR1 gene are produced intracellularly by transcription from an exogenous sequence. For example, a vector or a portion thereof, is transcribed, producing an antisense nucleic acid (RNA). Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the antisense molecule, can be by any promoter known in the art to act in vertebrate, preferably human cells, such as those described elsewhere herein.

Absolute complementarity of an antisense molecule, although preferred, is not required. A sequence complementary to at least a portion of an RNA encoding NgR1, means a sequence having sufficient complementarity to be able to hybridize with the RNA, forming a stable duplex; or triplex formation may be assayed. The ability to hybridize will depend on both the degree of complementarity and the length of the antisense nucleic acid. Generally, the larger the hybridizing nucleic acid, the more base mismatches it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of a messenger RNA, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333-335 (1994). Thus, oligonucleotides complementary to either the 5'- or 3'-non-translated, non-coding regions could be used in an antisense approach to inhibit translation of NgR1. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides, or at least 50 nucleotides.

Polynucleotides for use in the methods disclosed herein, including aptamers described below, can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci.* 84:648-652 (1987)); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958-976 (1988)) or intercalating agents. (See, e.g., Zon, *Pharm. Res.* 5:539-549(1988)). To this end, the oligonucleotide may be conjugated to another molecule, e.g., a peptide, hybridization triggered cross-linking agent, transport agent, hybridization-triggered cleavage agent, etc.

An antisense oligonucleotide for use in the methods disclosed herein may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N-6-adenine, 7-methylguanine, 5-methylaminomethyluracil, 5-methoxyaminomethyl-2-thiouracil, beta-D-mannosylqueosine, 5'methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3(3-amino-3-N2-carboxypropyl) uracil, (acp3)w, and 2,6-diaminopurine.

An antisense oligonucleotide for use in the methods disclosed herein may also comprise at least one modified sugar moiety selected from the group including, but not limited to, arabinose, 2-fluoroarabinose, xylulose, and hexose.

In yet another embodiment, an antisense oligonucleotide for use in the methods disclosed herein comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, an antisense oligonucleotide for use in the therapeutic methods disclosed herein is an α-anomeric oligonucleotide. An α-anomeric oligonucleotide forms specific double-stranded hybrids with complementary RNA in which, contrary to the usual situation, the strands run parallel to each other (Gautier et al., *Nucl. Acids Res.* 15:6625-6641(1987)). The oligonucleotide is a 2'-0-methylribonucleotide (Inoue et al., *Nucl. Acids Res.* 15:6131-6148 (1987)), or a chimeric RNA-DNA analogue (Inoue et al., *FEBS Lett.* 215:327-330(1987)).

Polynucleotides for use in the methods of the invention, including aptamers may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., *Nucl. Acids Res.* 16:3209 (1988), methylphosphonate oligonucleotides can be prepared by use of controlled pore glass polymer supports (Sarin et al., *Proc. Natl. Acad. Sci. U.S.A.* 85:7448-7451(1988)), etc.

Polynucleotide compositions for use in the methods disclosed herein further include catalytic RNA, or a ribozyme (See, e.g., PCT International Publication WO 90/11364, published Oct. 4, 1990; Sarver et al., *Science* 247:1222-1225 (1990). The use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). Preferably, the ribozyme is engineered so that the cleavage recognition site is located near the 5' end of the target mRNA, i.e., to increase efficiency and minimize the intracellular accumulation of non-functional mRNA transcripts.

As in the antisense approach, ribozymes for use in the diagnostic and therapeutic methods disclosed herein can be composed of modified oligonucleotides (e.g. for improved stability, targeting, etc.) and may be delivered to cells which express NgR1 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous NgR1 messages and inhibit translation. Since ribozymes unlike antisense molecules, are catalytic, a lower intracellular concentration is required for efficiency.

Aptamers

In another embodiment, the NgR antagonist for use in the methods of the present invention is an aptamer. An aptamer can be a nucleotide or a polypeptide which has a unique sequence, has the property of binding specifically to a desired target (e.g., a polypeptide), and is a specific ligand of a given target. Nucleotide aptamers of the invention include double stranded DNA and single stranded RNA molecules that bind to NgR1.

Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096, 5,580,737, 5,567, 588, 5,707,796, 5,763,177, 6,011,577, and 6,699,843, incorporated herein by reference in their entirety. Another screening method to identify aptamers is described in U.S. Pat. No. 5,270,163 (also incorporated herein by reference). The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets.

The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, preferably comprising a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; and amplifying the nucleic acids dissociated from the nucleic acid-target complexes to yield a ligand enriched mixture of nucleic acids. The steps of binding, partitioning, dissociating, and amplifying are repeated through as many cycles as desired to yield highly specific high affinity nucleic acid ligands to the target molecule.

Nucleotide aptamers may be used, for example, as diagnostic tools or as specific inhibitors to dissect intracellular signaling and transport pathways (James (2001) Curr. Opin. Pharmacol. 1:540-546). The high affinity and specificity of nucleotide aptamers makes them good candidates for drug discovery. For example, aptamer antagonists to the toxin ricin have been isolated and have 1050 values in the nanomolar range (Hesselberth J R et al. (2000) J Biol Chem 275:4937-4942). Nucleotide aptamers may also be used against infectious disease, malignancy, and viral surface proteins to reduce cellular infectivity.

Nucleotide aptamers for use in the methods of the present invention may be modified (e.g., by modifying the backbone or bases or conjugated to peptides) as described herein for other polynucleotides.

Using the protein structure of NgR1, screening for aptamers that act on NgR1 using the SELEX process would allow for the identification of aptamers that inhibit NgR1-mediated processes (e.g., NgR1-mediated inhibition of axonal regeneration).

Polypeptide aptamers for use in the methods of the present invention are random peptides selected for their ability to bind to and thereby block the action of NgR1. Polypeptide aptamers may include a short variable peptide domain attached at both ends to a protein scaffold. This double structural constraint greatly increases the binding affinity of the peptide aptamer to levels comparable to an antibody (nanomolar range). See, e.g., Hoppe-Seyler F et al. (2000) *J Mol Med* 78(8):426-430. The length of the short variable peptide is typically about 10 to 20 amino acids, and the scaffold may be any protein which has good solubility and compacity properties. One non-limiting example of a scaffold protein is the bacterial protein Thioredoxin-A. See, e.g., Cohen B A et al. (1998) *PNAS* 95(24): 14272-14277.

Polypeptide aptamers are peptides or small polypeptides that act as dominant inhibitors of protein function. Peptide aptamers specifically bind to target proteins, blocking their functional ability (Kolonin et al. (1998) *Proc. Natl. Acad. Sci.* 95: 14,266-14,271). Peptide aptamers that bind with high affinity and specificity to a target protein can be isolated by a variety of techniques known in the art. Peptide aptamers can be isolated from random peptide libraries by yeast two-hybrid screens (Xu, C. W., et al. (1997) *Proc. Natl. Acad. Sci.* 94:12, 473-12,478) or by ribosome display (Hanes et al. (1997) *Proc. Natl. Acad. Sci.* 94:4937-4942). They can also be isolated from phage libraries (Hoogenboom, H. R., et al. (1998) *Immunotechnology* 4:1-20) or chemically generated peptide libraries. Additionally, polypeptide aptamers may be selected using the selection of Ligand Regulated Peptide Aptamers (LiRPAs). See, e.g., Binkowski B F et al., (2005) *Chem & Biol* 12(7): 847-855, incorporated herein by reference. Although the difficult means by which peptide aptamers are synthesized makes their use more complex than polynucleotide aptamers, they have unlimited chemical diversity. Polynucleotide aptamers are limited because they utilize only the four nucleotide bases, while peptide aptamers would have a much-expanded repertoire (i.e., 20 amino acids).

Peptide aptamers for use in the methods of the present invention may be modified (e.g., conjugated to polymers or fused to proteins) as described for other polypeptides elsewhere herein.

Compositions

In some embodiments, the invention provides compositions comprising NgR1 polypeptides, NgR1 antibodies and antigen-binding fragments thereof, soluble Nogo receptors and fusion proteins thereof, and/or polynucleotides for use in the methods of the present invention.

In some embodiments, the compositions for use in the methods of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol and dextran. Optionally, the suspension may also contain stabilizers. Liposomes can also be used to encapsulate the molecules of this invention for delivery into the cell. Exemplary "pharmaceutically acceptable carriers" are any and all solvents, dispersion media, coatings, antibacterial and antifungal agents, isotonic and absorption delaying agents, and the like that are physiologically compatible, water, saline, phosphate buffered saline, dextrose, glycerol, ethanol and the like, as well as combinations thereof. In some embodiments, the composition comprises isotonic agents, for example, sugars, polyalcohols such as mannitol, sorbitol, or sodium chloride. In some embodiments, the compositions comprise pharmaceutically acceptable substances such as wetting agents or minor amounts of auxiliary substances such as wetting or emulsifying agents, preservatives or buffers, which enhance the shelf life or effectiveness of the antibodies, antigen-binding fragments, soluble Nogo receptors, fusion proteins, or polynucleotides used in the methods of the invention.

Supplementary active compounds also can be incorporated into the compositions for use in the methods of the invention. For example, NgR1 polypeptides, NgR1 antibodies or antigen-binding fragments thereof, soluble Nogo receptors or fusion proteins thereof, or polynucleotides may be coformulated with and/or coadministered with one or more additional therapeutic agents.

Compositions for use in the methods of the invention may be in a variety of forms, including, for example, liquid, semi-solid, and solid dosage forms, such as liquid solutions (e.g., injectable and infusible solutions), dispersions, or suspensions. The preferred form depends on the intended mode of administration and therapeutic application. In one embodiment, compositions are in the form of injectable or infusible solutions, such as compositions similar to those used for passive immunization of humans with other antibodies.

The composition can be formulated as a solution, micro emulsion, dispersion, liposome, or other ordered structure suitable to high drug concentration. Sterile injectable solutions can be prepared by incorporating an anti-Nogo receptor-1 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In some embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See e.g., *Sustained and Controlled Release Drug Delivery Systems*, J. R. Robinson, ed., Marcel Dekker, Inc., New York (1978).

The compositions for use in the methods of the invention may also comprise an NgR1 antagonist of the invention dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

The pharmaceutical compositions for use in the methods of the invention may include a "therapeutically effective amount" of an antibody, antigen-binding fragment, polypeptide(s), fusion protein, or polynucleotide. A "therapeutically effective amount" refers to an amount effective, at dosages and for periods of time necessary, to achieve the desired therapeutic result. A therapeutically effective amount of the NgR1 polypeptides, NgR1 antibodies and antigen-binding fragments thereof, soluble Nogo receptors and fusion proteins thereof, or polynucleotides may vary according to factors such as the disease state, age, sex, and weight of the individual. A therapeutically effective amount is also one in which any toxic or detrimental effects of the NgR1 polypeptides, NgR1 antibodies and antigen-binding fragments thereof, soluble Nogo receptors and fusion proteins thereof, or polynucleotides are outweighed by the therapeutically beneficial effects.

For treatment with an NgR1 antagonist of the invention, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage unit form as used herein refers to physically discrete units suited as unitary dosages for the mammalian subjects to be treated, each unit containing a predetermined quantity of active compound calculated to produce the desired therapeutic effect in association with the required pharmaceutical carrier. The specification for the dosage unit forms for use in the methods of the invention are dictated by and directly dependent on (a) the unique characteristics of the antibody, antigen-binding fragment, soluble receptor-1 polypeptide, Nogo receptor fusion protein, or polynucleotide and the particular therapeutic effect to be achieved, and (b) the limitations inherent in the art of compounding such an antibody, antigen-binding fragment, soluble receptor-1 polypeptide, Nogo receptor fusion protein, or polynucleotide for the treatment of sensitivity in individuals. In some embodiments a therapeutically effective dose range for Nogo receptor-1 antibodies or antigen-binding fragments thereof is 0.1-4 mg/kg per day. In some embodiments a therapeutically effective dose range for Nogo receptor-1 antibodies or antigen-binding fragments thereof is 0.2-4 mg/kg per day. In some embodiments a therapeutically effective dose range for Nogo receptor-1 antibodies or antigen-binding fragments thereof is 0.2 mg/kg per day.

The invention encompasses any suitable delivery method for an NgR1 antagonist to a selected target tissue, including bolus injection of an aqueous solution or implantation of a controlled-release system. Use of a controlled-release implant reduces the need for repeat injections. Other suitable methods include, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In certain methods of the invention, the Nogo-receptor antagonist must cross the blood-brain barrier. This crossing can result from the physico-chemical properties inherent in the Nogo-receptor antagonist molecule itself, from other components in a pharmaceutical formulation, or from the use of a mechanical device such as a needle, cannula or surgical instruments to breach the blood-brain barrier. Where the Nogo-receptor antagonist is a soluble Nogo receptor, anti-Nogo receptor antibody, or other molecule that does not inherently cross the blood-brain barrier, a suitable route of administration is intracranial, e.g., directly into the lateral ventricles, the intrathecal space, the cerebral cortex, or the spinal cord parenchyma. Where the Nogo receptor antagonist is a molecule that inherently crosses the blood-brain barrier, the route of administration may be by one or more of the various routes described herein and that are known in the art.

In the methods of the invention the Nogo-receptor antagonists are generally administered directly to the nervous system, intracerebroventricularly, or intrathecally, e.g., into the site of chronic SCI. For example, the Nogo-receptor antagonists for use in the methods of the invention may be directly infused into the brain. In some embodiments, the direct brain infusion of the Nogo-receptor antagonist is into an appropriate region of the brain. See, e.g., Gill et al., "Direct brain infusion of glial cell line-derived neurotrophic factor in Parkinson disease," *Nature Med.* 9: 589-95 (2003).

Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-91 (1992); Gaspar et al., "Permanent 125I Implants for Recurrent Malignant Gliomas," *Int. J. Radiation Oncology Biol. Phys.* 43(5):977-82 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation. The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

Methods of Using Nogo-Receptor Antagonists

This invention relates to methods of treating chronic nervous system diseases or injuries using Nogo-receptor antagonists. Chronic nervous system diseases or injuries include, but are not limited to, chronic spinal cord injury (SCI). Other examples of chronic nervous system diseases or injuries that could be treated with the methods of the present invention include, but are not limited to, chronic deficits after stroke, traumatic brain injury, or chronic progressive multiple sclerosis.

One embodiment of the present invention provides a method of treating chronic SCI in a mammal, comprising administering to a mammal in need thereof a therapeutically effective amount of a Nogo-receptor antagonist. Another embodiment provides that the Nogo-receptor antagonist stimulates axonal growth.

Another embodiment of the present invention provides a method of treating a mammal displaying signs or symptoms of chronic SCI, comprising administering to a mammal in need thereof a therapeutically effective amount of a Nogo-receptor antagonist to said mammal. Another embodiment provides that the Nogo-receptor antagonist stimulates axonal growth.

A further embodiment of the present invention provides a method for stimulating axonal growth, neurite outgrowth, or axonal regeneration following chronic SCI, comprising administering a therapeutically effective amount of a Nogo-receptor antagonist. Another embodiment of the present invention provides a method for reactivating axonal growth, for promoting neurite outgrowth, or for promoting neuronal survival following chronic SCI, comprising administering a therapeutically effective amount of a Nogo-receptor antagonist.

Any of the Nogo-receptor antagonists described herein may be used therapeutically in the methods of the invention. The Nogo receptor-1 polypeptides, Nogo receptor-1 antibodies and antigen-binding fragments thereof, soluble Nogo receptors and fusion proteins thereof, and polynucleotides for use in the methods of the present invention can be provided alone, or in combination, or in sequential combination with other agents that modulate a particular pathological process. As used herein, the Nogo receptor-1 antibodies, antigen-binding fragments, soluble Nogo receptor-1 and Nogo receptor fusion proteins, are said to be administered in combination with one or more additional therapeutic agents when the two are administered simultaneously, consecutively or independently.

The anti-Nogo receptor-1 antibodies, antigen-binding fragments, soluble Nogo receptor-1 polypeptides, Nogo receptor-1 fusion proteins for use in the methods of the present invention can be administered by bolus injection, chronic infusion, or implantation of a controlled-release system. Other routes of administration include, for example, directly into the central nervous system, intracerebroventricularly, or intrathecally. Additional routes of administration include, for example, parenterally, intraventricularly, orally, by inhalation spray, topically, rectally, nasally, buccally, vaginally, or via an implanted reservoir. Typical sites include, but are not limited to, damaged areas of the nervous system, such as the spinal cord, resulting from disease or injury, including but not limited to, spinal contusion. The dosage administered will be dependent upon the age, health, and weight of the recipient, kind of concurrent treatment, if any, frequency of treatment, and the nature of the effect desired. Therapeutically effective amounts can include from 0.001 mg/k to 10 mg/kg of Nogo-receptor antagonist, from 0.01 mg/kg to 1.0 mg/kg, or from 0.05 mg/kg to 5 mg/kg.

The Nogo-receptor antagonists for use in the methods of the invention can be utilized in vivo, ordinarily in mammals, such as humans, sheep, horses, cattle, pigs, dogs, cats, rats and mice, or in vitro. The Nogo-receptor antagonists can be used to treat chronic nervous system disease or injury, such as a chronic SCI, including but not limited to, a spinal contusion.

The Nogo-receptor antagonists for use in the methods of the invention can be administered at a time selected from the group consisting of: (a) greater than a week after the initial injury; (b) two weeks or greater after the initial injury; (c) three weeks or greater after the initial injury; (d) four weeks or greater after the initial injury; (e) two months or greater after the initial injury; (f) three months or greater after the initial injury; (g) four months or greater after the initial injury; (h) five months or greater after the initial injury; (i) six months or greater after the initial injury; (j) seven months or greater after the initial injury; (k) eight months or greater after the initial injury; (l) nine months or greater after the initial injury; (m) ten months or greater after the initial injury; (n) eleven months or greater after the initial injury; and (o) twelve months or greater after the initial injury. In one aspect, the Nogo-receptor antagonist is administered three months or greater after the initial injury.

Methods of Monitoring Treatment of Chronic Spinal Cord Injury (SCI)

The invention provides various methods for monitoring treatment of chronic SCI, including various behavioral testing methods. For example, for rat behavioral testing, the Basso, Beattie, Bresnahan (BBB) Locomotor Rating Scale can be used (D. M. Basso et al., *J. Neurotrauma* 13:343-59 (1996); D. M. Basso et al., *J. Neurotrauma* 12:1-21 (1995)). Additionally, grip strength can be measured using, e.g., a Columbus Instruments force meter. Grid walking can be used to assess the deficits in descending fine motor control after spinal cord injury (Metz et al., *Brain Res.* 883:165-177 (2000)). This performance requires forelimb-hindlimb coordination and voluntary movement control mediated by ventrolateral, corticospinal and rubrospinal fibers. During the pre-injury training, rats accurately place their hindlimbs on the grid bars. Such behavioral assessment methods can be used to measure the effect of, e.g., Nogo receptor antagonists on chronic SCI. Various additional methods are known in the art and can be used to assess treatment of chronic SCI in mammals.

Noninvasive Imaging Methods

The invention also provides methods of noninvasively monitoring axonal growth during and after treatment with an axonal growth promoting agent. Methods of noninvasively monitoring axonal growth in, for example, a chronic nervous system disease or injury such as chronic SCI, include imaging techniques that do not require the insertion of an instrument or device through the skin or a body orifice, such as Positron Emission Tomography (PET).

PET, which is a type of medical radionuclide imaging, is a diagnostic tool that involves the use of ionizing radiation to obtain accurate in vivo imaging. PET imaging systems create three-dimensional images of the in vivo biochemistry or physiology in a specific organ, tumor, or other metabolically active site based on the distribution of positron-emitting isotopes in those sites. See, e.g., U.S. Pat. No. 7,126,126. Analysis of the photons detected from the deterioration of these positrons is used to generate the tomographic images which may be quantified using a color scale to show the diffusion of the biochemical substances in the tissue indicating localization of biochemical and/or physiological processes.

Typically, one or more biologically appropriate compounds labelled with radionuclides are administered to a patient, as by ingestion, inhalation, or injection, e.g., into the bloodstream. For example, radionuclides used in PET may be a. short-lived radioactive isotope such as Flourine-18, Oxygen-15, Nitrogen-13, and Carbon-11 (with half-lives ranging from 110 minutes to 20 minutes). See, e.g., U.S. Pat. No. 7,126,126. The radionuclides may be incorporated into biochemical substances such as compounds normally used by the body that may include, e.g., sugars, water, and/or ammonia. For example, a biochemical substance, such as a radiolabelled sugar, may be injected into the bloodstream where the sugar becomes concentrated in the tissue of interest and the radionuclide decays emitting positrons.

Tracer amounts of these radiolabelled substances emanate gamma quanta while localized at a specific organ, tumor, or other metabolically active site. PET is then used to record the internal spatial distribution of the radionuclide as it propagates from the study area. In PET, events are detected from the decay or annihilation of positrons and electrons. When a positron is annihilated by an electron, two 511 keV gamma photons are simultaneously produced and travel in approximately opposite directions (N. Sharma et al., *Radiation Onc.* 3:25-37 (2008)). Gamma photons produced by an annihilation event can be detected by a pair of oppositely disposed scintillating detectors capable of producing a signal in response to the interaction of the gamma photons with a crystal of the scintillating detectors. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence, they also identify a line of response, or LOR, along which the annihilation event has occurred. See, e.g., U.S. Pat. No. 7,402,807.

Applications of PET include, e.g., analysis of kidney function, imaging blood-flow and heart function, scanning lungs for respiratory performance, determining the presence and/or spread of cancer, evaluating brain activity, determining the location of epileptic seizures, diagnosing brain disorders such as Alzheimer's and Parkinson's disease, and measuring thyroid function and activity.

SCI produces neurological deficits by severing nerve fibers. Serotonergic axons descend from the raphe to the spinal cord and contribute to motor tone and locomotion. Y. Huang et al., *J. Nucl. Med.* 49(Supplement 1):83P (2008). In rodents, for example, the raphespinal pathway is sensitive to axonal growth promoting interventions and is predictive of behavior outcomes. Using a noninvasive technique such as MRI to monitor such pathways and axonal growth promoting interventions has not previously been possible, in part, because of the branched, tortuous, and disorganized growth that occurs after treatment of SCI with axonal growth promoting agents. However, PET and neuro-targeted radioligands provide a more specific imaging modality to monitor such axonal growth.

Previous applications of PET have not used PET to image axon growth in the spinal cord, including the injured spinal cord. In particular, prior applications of PET have not used [$^{11}$C]2-[2-(dimethylaminomethylphenylthio)]-5-fluoromethylphenyl amine ([$^{11}$C]AFM), a serotonin transporter (SERT) ligand, to image axon growth in the spinal cord. The methods of the invention provide for such application of PET in noninvasively monitoring axonal growth after treatment with an axonal growth promoting agent.

One embodiment of the present invention provides a method of non-invasively monitoring axonal growth after treatment with an axonal growth promoting agent, comprising imaging [$^{11}$C]AFM binding to 5HTT in the affected spinal cord using Positron Emission Tomography.

Another embodiment of the present invention provides a method for monitoring axonal growth during treatment with an axonal growth promoting agent, comprising: (a) administering an axonal growth promoting agent to a mammal; and (b) imaging [$^{11}$C]AFM binding to 5HTT in the treated spinal cord using Positron Emission Tomography.

A further embodiment of the present invention provides method for determining axonal growth following treatment with an axonal growth promoting agent, comprising: (a) administering [$^{11}$C]AFM to a mammal treated with an axonal growth promoting agent; (b) imaging [$^{11}$C]AFM binding to 5HTT in said mammal using Positron Emission Tomography; and (c) measuring lumbar uptake of [$^{11}$C]AFM as a proportion of cervical uptake of [$^{11}$C]AFM. In one embodiment, an increased ratio of lumbar uptake to cervical uptake in a mammal treated with an axonal growth promoting agent compared to the ratio of a mammal not treated with an axonal growth promoting agent is indicative of axonal growth.

These methods can include monitoring treatment of chronic spinal cord injury using axonal growth promoting agents. Axonal growth promoting agents refer to any agent that promotes or stimulates the growth of axons. Examples of axonal growth promoting agents include, but are not limited to, any Nogo receptor antagonists described herein, including NgR1 polypeptides, NgR1 antibodies and antigen-binding fragments thereof, soluble Nogo receptors and fusion proteins thereof, and/or polynucleotides. Other examples of axonal growth promoting agents include agents such as, but not limited to, ibuprofen, stem cell transplants, anti-Nogo antibodies, or an exercise regimen.

It will be readily apparent to one of ordinary skill in the relevant arts that other suitable modifications and adaptations to the methods and applications described herein are obvious and may be made without departing from the scope of the invention or any embodiment thereof. In order that this invention may be better understood, the following examples are set forth. These examples are for purposes of illustration only and are not to be construed as limiting the scope of the invention in any manner.

EXAMPLE 1

Reactivation of Axonal Growth in a Chronic Spinal Cord Injury (SCI) Model 1.1 Chronic Rat Spinal Contusion Injury with Prolonged Intracerebroventricular Therapy Female Sprague-Dawley rats (11-12 weeks, 250-270 g) were anesthetized with intraperitoneal injection of ketamine (60 mg/kg) and xylazine (10 mg/kg). A laminectomy was conducted at the caudal portion of T6 and all of T7 spinal levels. A T7 moderate contusion injury (10 g, 25 mm) was produced with the MASCIS impactor (D. M. Basso et al., *J. Neurotrauma* 13:343-59 (1996); X. Wang et al., *Ann. Neurol.* 60:540-49 (2006); W. Young, *Prog. Brain Res.* 137:231-255 (2002)). After the contusion the locomotor performance was assessed at one-week intervals by using the BBB score in the open field. Locomotor scores reached a stable level of 8 by 7 weeks after injury.

In order to avoid any confounding unfavorable effect of the cannula implantation procedure on locomotor scores, a cannula (Alzet® Brain Infusion Kit II; Alza Scientific Products) was implanted into the right lateral ventricle at 10 weeks post-contusion injury as described previously (J. H. Park et al., *J. Neurosci.* 26:1386-95 (2006); J. K. Lee et al., *J. Neurosci.* 24:6209-6217 (2004)). Briefly, the scalp was opened, a burr hole was drilled through the skull, and a cannula was introduced into the right lateral ventricle at stereotaxic coordinates 0.6 mm posterior and 1.2 mm lateral to bregma and 4.0 mm deep to the pial surface. The cannula was connected to an osmotic minipump containing PBS placed subcutaneously over the scapulae. The cannula was fixed in place with cyanoacrylate, and the skin was sutured.

Two weeks after the cannula implantation (12 weeks post-contusion injury), the rats were reanesthetized and the minipumps were replaced with new osmotic minipumps (Alza Scientific Products) connected to the same cannula.

These pumps delivered 2.5 μL/hour for 28 days and were filled with 2.25 mg AA-NgR(310)ecto-Fc (0.29 mg/kg/day) or 2.25 mg IgG from rat serum (#14131-50 mg, Sigma®) in 2 mL PBS. The duration of treatment was 12 weeks. A new osmotic minipump filled with same amount of AA-NgR(310) ecto-Fc or rat IgG was switched every 4 weeks.

1.2 AA-NgR(310)ecto-Fc Protein

Purified rat protein was produced in CHO cells and purified as described previously (S. Li et al., *J. Neurosci.* 24:10511-20 (2004)) with one modification. Because the wild-type fusion protein exhibits a high percentage of disulfide bond heterogeneity, a variant was produced in which the two Cys residues at position 266 and 309 of the full length NgR1 were changed to Ala. This AA variant is homogenous with respect to disulfide bonding and is fully active in vitro.

1.3 Behavioral Testing

For the rat behavioral testing, the Basso, Beattie, Bresnahan (BBB) Locomotor Rating Scale was used (D. M. Basso et al., *J. Neurotrauma* 13:343-59 (1996); D. M. Basso et al., *J. Neurotrauma* 12:1-21 (1995)). All behavioral tests were performed by two researchers unaware of the identity of the compound in the minipump. Observations were made once per week and single monthly post-treatment values for each rat were determined by averaging values during weeks 1-4, 5-8, or 9-12.

Grip strength was measured using a Columbus Instruments force meter. Each rat was tested three times for each limb and the data were averaged.

1.4 Histology and Analysis

Animals were perfused transcardially with PBS, followed by 4% paraformaldehyde, PBS solution. The spinal cord 10 mm rostral to and 10 mm caudal to the lesion center was embedded in a glutaraldehyde-polymerized albumin matrix and cut parasagitally in the thickness of 40 μm on a vibratome. Transverse sections (40 μm) were collected from the spinal cord 11 to 16 mm rostral to and 11 to 16 mm caudal to the lesion center (X. Wang et al., *Ann. Neurol.* 60:540-49 (2006); S. Li et al., *J. Neurosci.* 24:10511-20 (2004); W. B. Cafferty et al., *J. Neurosci.* 27:2176-85 (2007); W. B. Cafferty and S. M. Strittmatter, *J. Neurosci.* 26:12242-50 (2006); S. Li et al., *Mol. Cell Neurosci.* 29:26-39 (2005); J. E. Kim et al., *Neuron* 44:439-51 (2004); S. Li and S. M. Strittmatter, *J. Neurosci.* 23:4219-27 (2003); J. E. Kim et al., *Neuron* 38:187-99 (2003); T. GrandPre et al., *Nature* 417:547-51 (2002)).

Sagittal sections of thoracic spinal cord were incubated with anti-5-hydroxytryptamine (anti-5-HT) antibody (1:10, 000; ImmunoStar, Hudson, Wis.) and then with Alexa Fluor® 568-labeled secondary antibody (Invitrogen) to detect raphespinal fibers (See id.). Transverse sections 11-16 mm caudal to the lesion center were incubated with anti-5-hydroxytryptamine antibody or anti-serotonin transporter antibody (1:10,000 or 1:1,000; ImmunoStar, Hudson, Wis.) and were visualized with appropriate secondary antibody conjugated to Alexa Fluor® 568 (Invitrogen).

Image analysis was accomplished with National Institutes of Health (NIH) image version 1.62, as described previously (See id.). For analysis of serotonin innervation, immunoreactive serotonin fibers in the ventral horn of transverse sections caudal to the lesion center were selected by thresholding; then the length of serotonin fiber per area was measured after using the skeletonize function. For camera lucida tracing of 5-HT-immunoreactive fibers, 10 serial sections at 200 μm intervals from each animal were photographed digitally, and fibers were traced on a computer using Adobe® Photoshop® 7.0 software (Adobe Systems, Mountain View, Calif.).

1.5 Results

Figures 1D, 1E, 1F, 1G, 1H, 1I:
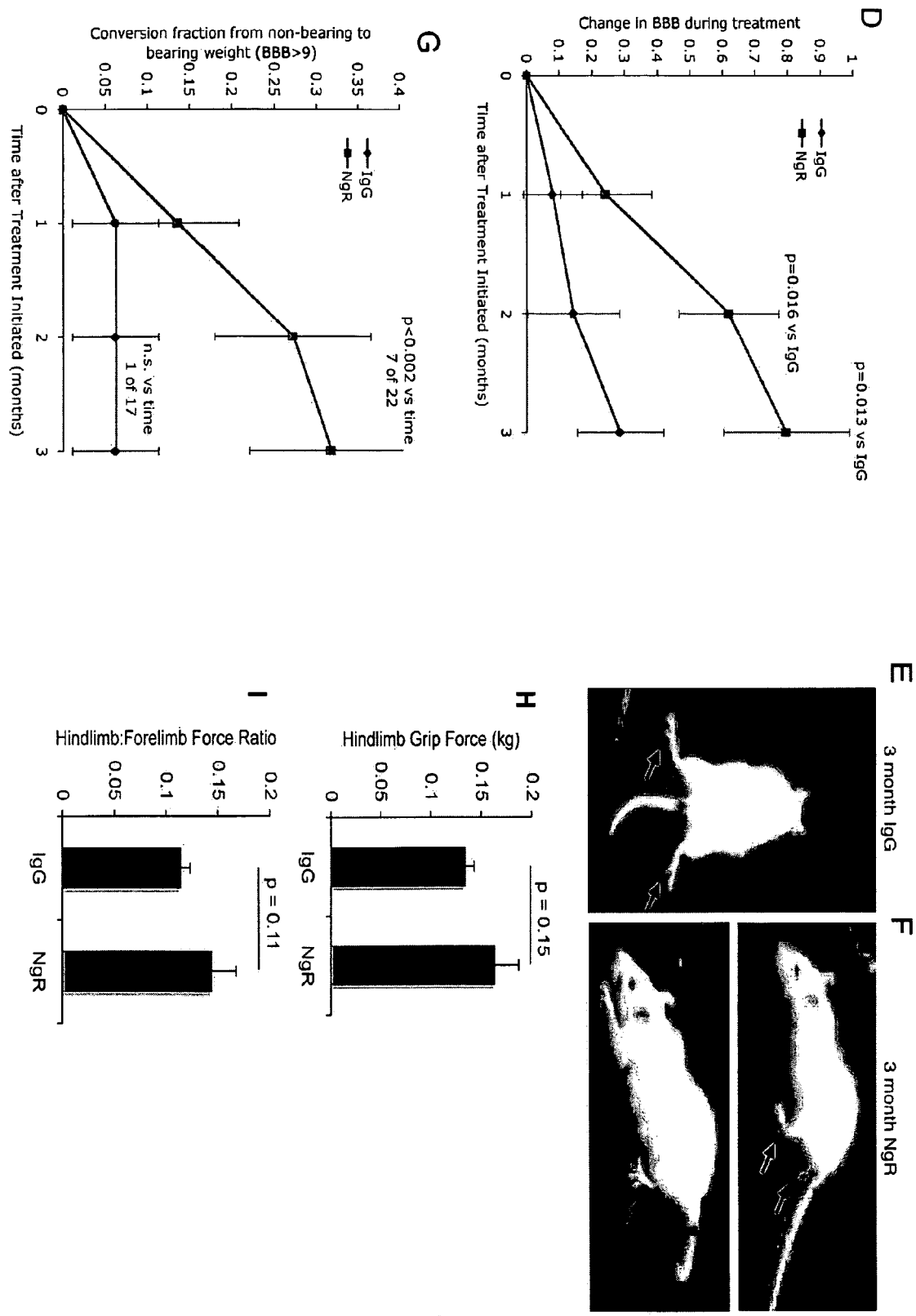
FIG. 1D is a graph depicting the change in BBB score for each rat in the two treatment groups. Data are mean±sem for n=21 or 25 per group. One-way ANOVA by treatment for each time point were determined using InStat and SPSS software.
FIG. 1E depicts an IgG control rat without weight support at the end of the treatment period.
FIG. 1F depicts two of the seven AA-NgR(310)ecto-Fc treated rats that regained weight support.
FIG. 1G is a graph depicting the fraction of rats without body weight support using the hindlimbs at the initiation of therapy that later recovered body weight support during treatment. Seven of 22 animals from the AA-NgR(310)ecto-Fc-treated group recovered this ability, while only 1 out of 17 animals in the IgG control group. A Friedman test for non-parametric repeated measures ANOVA was utilized to compare the effect of time for each group.
FIGS. 1H and 1I are graphs depicting the hindlimb grip force and the hindlimb:forelimb force ratio, respectively, for each treatment group. After three months of AA-NgR(310) ecto-Fc or rat IgG therapy, grip strength was measured. The force of the hindlimb grip or the ratio of the hindlimb to forelimb grip force is reported. Data are mean±sem for n=12 per group. The statistical significance of the indicated differences was assessed by ANOVA.

A cohort of 46 rats survived thoracic spinal cord contusion injuries and exhibited stable motor scores without fluctuation between 6-12 weeks after injury (FIG. 1A). The rats were monitored by BBB scoring (mean±sem, n=46). The BBB scores plateaued by six weeks after contusion, and the average BBB score at 12 weeks was 7.9±0.1, meaning that the majority of rats were capable of hindlimb movement, but not weight support (D. M. Basso et al., *J. Neurotrauma* 12:1-21 (1995); D. M. Basso et al., *J. Neurotrauma* 13:343-59 (1996)). A cannula connected to an osmotic minipump containing PBS was implanted into the right lateral ventricle at 10 weeks post-contusion injury (pump) without significant deficit from surgery. Two weeks after intracerebroventricular (i.c.v.) catheter placement (12 weeks post-contusion injury), the animals were assigned to one of two treatment groups and received either 2.25 mg AA-NgR(310)ecto-Fc or 2.25 mg control IgG protein in 2 mL PBS for 12 weeks at a dose of 0.29 mg/kg/d (X. Wang et al., *Ann. Neurol.* 60:540-49 (2006); S. Li et al., *J. Neurosci.* 24:10511-20 (2004); J. K. Lee et al., *J. Neurosci.* 24:6209-17 (2004)). All animal handling, behavioral scoring, neuroimaging and histological analysis were performed by personnel without knowledge of the assigned treatment group. The initial BBB scores from the IgG (n=21) and AA-NgR(310)ecto-Fc (n=25) treated groups were identical (FIG. 1B). There was a significant improvement over three months in the AA-NgR(310)ecto-Fc group, but not the control group (FIG. 1C). The improvement of each animal's BBB score in the AA-NgR(310)ecto-Fc treated group was significantly greater than in the control group (FIG. 1D). Because most control rats did not step or support weight with the hindlimbs, detailed gait analysis was not possible.

The most conspicuous behavioral change was the conversion from hindlimb non-weight-bearing to hindlimb weight-bearing locomotion (FIGS. 1E and 1F). Seven of 22 animals from the AA-NgR(310)ecto-Fc treated group converted to weight bearing, while only one out of 17 animals in the IgG control did so over this three month period (FIG. 1G). A Friedman test for nonparametric repeated measures ANOVA was utilized to compare the effect of time for each group. These data indicate that AA-NgR(310)ecto-Fc treatment of chronic spinal contusion improves neurological recovery.

The grip force of the affected hindlimbs and the intact forelimbs was measured in a random subset of these rats (FIGS. 1H and 1I). There was a trend towards improved hindlimb grip strength measured by absolute force or as a ratio to forelimb strength in the same animal. Thus, these date further indicated that AA-NgR(310)ecto-Fc treatment of chronic spinal contusion improves neurological recovery.

Figures 2A, 2B, 2C, 2D, 2E, 2F, 2G, 2H:
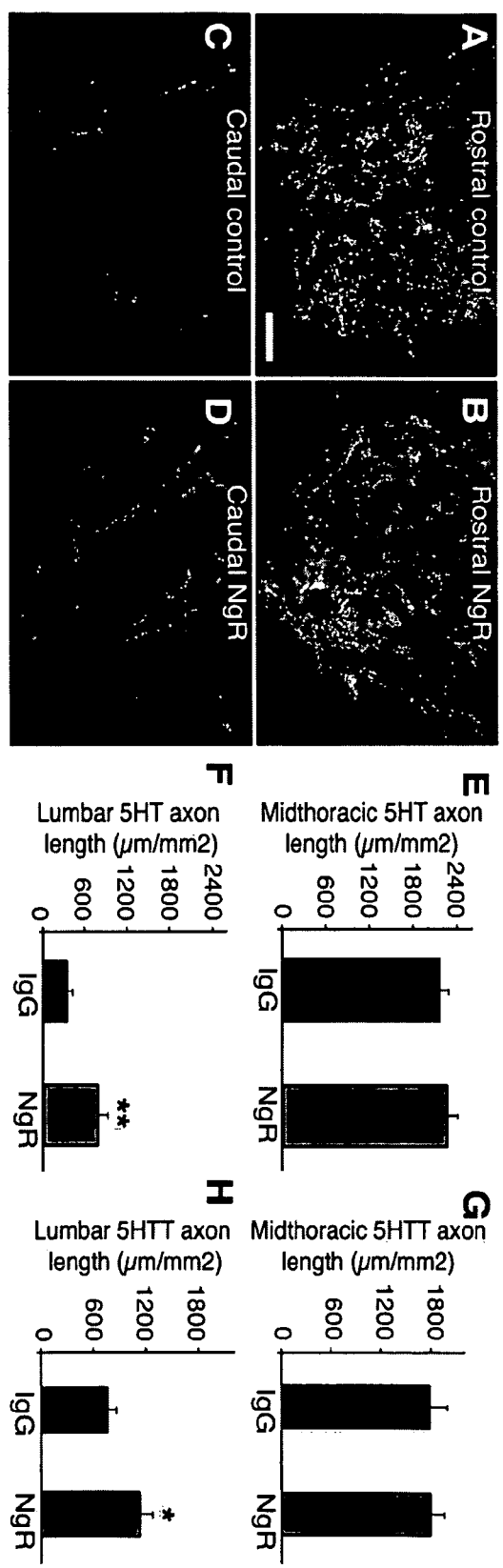
FIGS. 2A and 2C depict a rostral and a caudal transverse section, respectively, from the spinal cord of a rat in the IgG control group stained with anti-5-HT. Anti-serotonin immunohistochemistry demonstrates 5-HT fibers in the ventral horn of the spinal cord.
FIGS. 2B and 2D depict a rostral and a caudal transverse section, respectively, from the spinal cord of a rat in the AA-NgR(310)ecto-Fc-treated group stained with anti-5-HT. Anti-serotonin immunohistochemistry demonstrates 5-HT fibers in the ventral horn of the spinal cord. Note the decreased innervation caudal to the injury and the partial recovery in the AA-NgR(310)ecto-Fc treated rats. Scale bar, 25 µm.
FIGS. 2E and 2F are graphs depicting the length of midthoracic 5HT or lumbar 5HT axon length, respectively, from each treatment group. The length of 5HT-immunoreactive axon per unit area of ventral horn in the transverse plane was measured for chronic SCI rats completing 3 months treatment with either the IgG control or AA-NgR(310)ecto-Fc. The data are mean±sem for n=21-25 per group, and the increase in the NgR group in the distal cord is significant, $P<0.01$, ANOVA, **.
FIGS. 2G and 2H are graphs depicting anti-serotonin reuptake of adjacent spinal cord sections from each treatment group. Adjacent sections were processed for anti-serotonin reuptake site immunohistochemistry and measured as for 5HT in 2E and 2F. The data are mean±sem for n=21-25 per group, and the increase in the NgR group in the distal cord is significant, $P<0.05$, ANOVA, *.

Previous studies of NgR antagonism predict that the improved neurological function might be due to axonal growth (See id.; W. B. Cafferty et al., *Neuron* 54:195-99 (2007); L. Dimou et al., *J. Neurosci.* 26:5591-603 (2006); J. E. Kim et al., *Neuron* 44:439-51 (2004); J. E. Kim et al., *Neuron* 38:187-99 (2003); T. GrandPre et al., *Nature* 403: 439-44 (2000)). Post-mortem histological examination of acutely treated spinal injured rats has demonstrated the growth of descending raphespinal axons in the caudal spinal cord after NgR(310)ecto-Fc therapy in an acute SCI model (X. Wang et al., *Ann. Neurol.* 60:540-49 (2006); S. Li et al., *J. Neurosci.* 24:10511-20 (2004)). Similarly, increased serotonin (5HT) fiber length was observed in the lumbar spinal cord after treatment of chronic SCI (FIG. 2A-F, FIG. 3A-C). Anti-serotonin immunohistochemistry demonstrated 5-HT fibers in the ventral horn of the spinal cord (FIG. 2A-D). There was also decreased innervation caudal to the injury and partial recovery in the AA-NgR(310)ecto-Fc treated rats. (FIGS. 2B and D). The length of 5HT-immunoreactive axon per unit area of ventral horn in the transverse plane was measured for chronic SCI rats completing three months treatment with either the IgG control or AA-NgR(310)ecto-Fc. (FIGS. 2E and 2F).

Figure 3A:
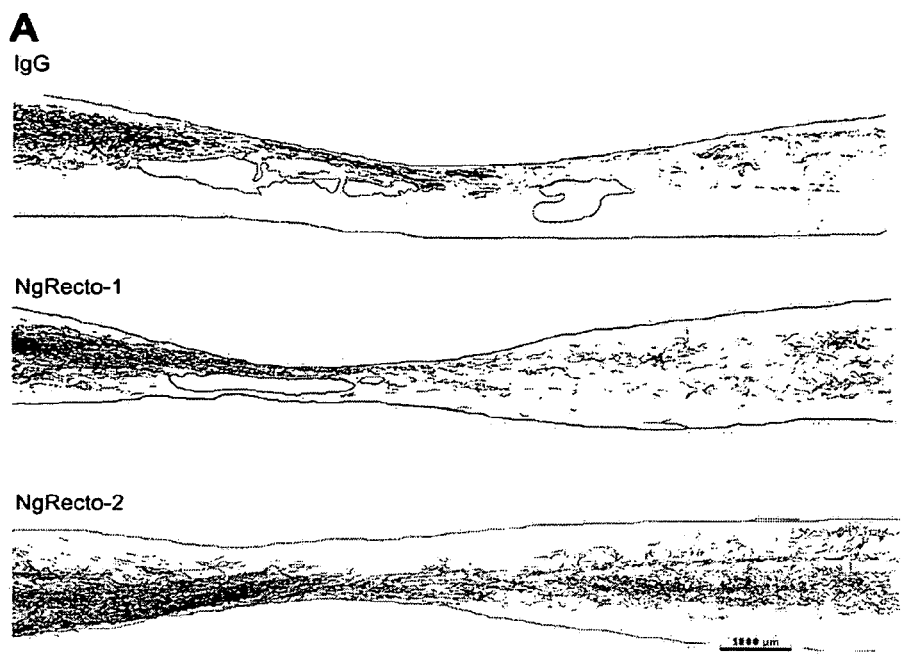
FIG. 3A depicts camera lucida drawings of serotonergic fibers from one IgG-treated and two AA-NgR(310)ecto-Fc-treated animals. Each drawing is a composite assembled from a set of 10 parasagittal sections spaced at intervals of 200 µm across the spinal cord. The contusion cavities are encircled near the center of each image. Increased numbers of serotonergic fibers are observed in the caudal spinal cord in the AA-NgR(310)ecto-Fc-treated (NgRecto-1, NgRecto-2) animals compared with the IgG-treated animals. Scale bar is 1000 µm.
Figure 3B:
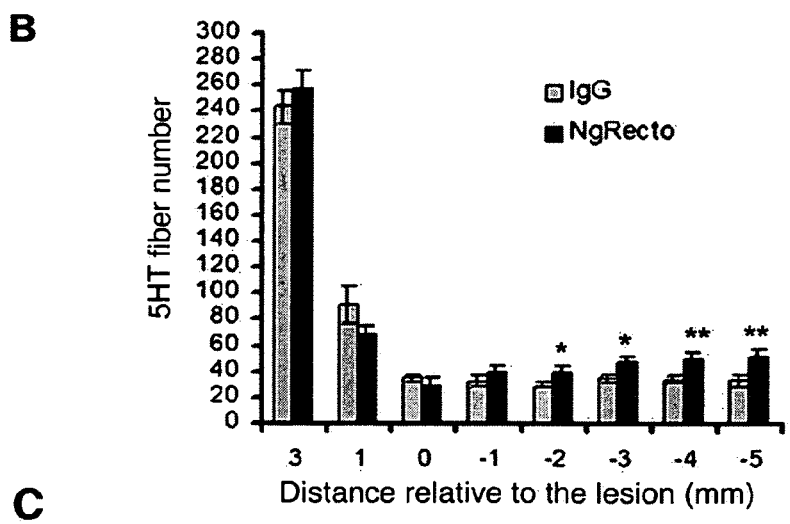
FIG. 3B is a graph depicting serotonergic (5HT) fiber number at various distances rostral and caudal to the center of the lesion from AA-NgR(310)ecto-Fc-treated (black bars) and control animals (gray bars). *, $p<0.05$; **, $p<0.01$, ANOVA. For the x-axis, a positive value is rostral to the center of the lesion, and a negative value is caudal to the center of lesion.

Sagittal sections demonstrate increased raphepspinal fibers throughout the caudal spinal cord of NgR(310)ecto-Fc treated rats (FIGS. 3A and 3B). Each camera lucida drawing is a composite assembled from a set of 10 parasagittal sections spaced at intervals of 200 µm across the spinal cord. The contusion cavities are encircled near the center of each image (FIG. 3A). Increased numbers of serotonergic fibers are observed in the caudal spinal cord in the AA-NgR(310)ecto-Fc-treated (NgRecto-1, NgRecto-2) animals compared with the IgG treated animals (FIG. 3A). Although not wishing to be bound by any particular theory, these data provide histological support for local axon growth from uninjured and injured fibers being the mechanism of behavioral improvement by AA-NgR(310)ecto-Fc in chronic spinal contusion.

Figure 3C:
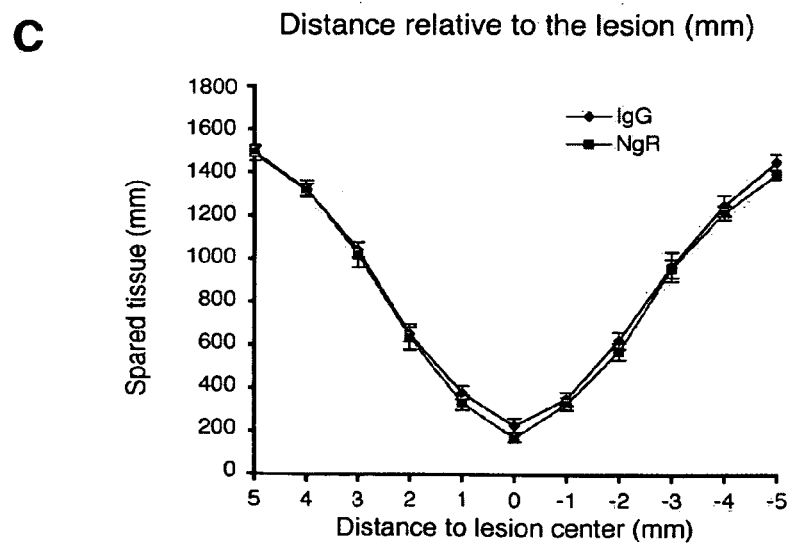
FIG. 3C is a graph depicting no effect of chronic AA-NgR (310)ecto-Fc treatment on spinal atrophy. Ten serial longitudinal sections at 200 µm intervals from each animal were used for spared tissue measurement. The dorsal-ventral extent of spared tissue was measured as a function of rostral-caudal distance from the lesion center. For the x-axis, a positive value is rostral to the center of the contusion, and a negative value is caudal to the center of the lesion. There is no difference in the extent of spared tissue between the two treatment groups. Mean±sem from 6 rats in each group.

In addition, measurement of the dorsal-ventral extent of spared tissue as a function of rostral-caudal distance showed no effect on spinal atropy following treatment with AA-NgR (310)ecto-Fc as compared to IgG (FIG. 3C). Ten serial longitudinal sections at 200 µm intervals from each animal were used for spared tissue measurement. The dorsal-ventral extent of spared tissue was measured as a function of rostral-caudal distance from the lesion center. There was no difference in the extent of spared tissue between the two treatment groups (FIG. 3C).

These studies demonstrated that axonal growth can be stimulated by AA-NgR(310)ecto-Fc therapy long after spontaneous neurological recovery has ceased and that the axonal growth stimulated by AA-NgR(310)ecto-Fc therapy is associated with substantial neurological benefits in the chronic rat spinal contusion model.

EXAMPLE 2

Pet Imaging of Axonal Growth During Chronic SCI Therapy 2.1 [$^{11}$C]AFM Imaging by PET At the end of a three month treatment period 11 rats in the AA-NgR(310)ecto-Fc group and 13 rats in the IgG group were anesthetized under isofluorane inhalation and [$^{11}$C] AFM images were obtained by Positron Emission Tomography (PET). The general methods for PET imaging of serotonin transporters (5HTT) have been described (Y. Huang et al., J. Cereb. Blood Flow Metab. 22:1377-98 (2002); Y. Huang et al., Nucl. Med. Biol. 31:543-56 (2004)). The imaging chamber was a bi-level plexi-glass rectangular box, with one rat housed on the top and two rats on the bottom. Oxygen and isoflurane (2-3%) was delivered to the top level via tubing and waste gas was removed via tubing in the front of the chamber. Holes were made in the first level floor to allow for the passage of anesthetic and waste gas. The rats were positioned at the front of the chamber lying on their right sides. Their tails were passed through holes at the front of the chamber to allow for the placement of a butterfly catheter and the delivery of the radiotracer and competing drug. Data were collected on the High Resolution Research Tomograph (HRRT) PET scanner for 120 minutes following i.v. injection of ~1 mCi [$^{11}$C] AFM for each rat. Summed images were created from 30-60 minutes post-injection and the spinal cord identified in the sagittal plane. Two 1×1×5 rectangular regions-of-interest (ROI) were defined on the cervical and lumbar areas of the spinal cord for each rat imaged. The mean radioactivity concentrations within the ROI were extracted from the image, and the ratio of lumbar-to-cervical activity uptake was calculated.

2.2 Results

Clinical trials of axonal growth promoting therapies will be facilitated by a design that utilizes chronic and stable injuries rather than the variable natural history of acute injury. In addition, proof of concept trials would be greatly enhanced by methods to directly monitor the presence of axonal growth non-invasively. Diffusion tensor imaging by magnetic resonance has demonstrated massive disruption of highly fasciculated spinal cord tracts after injury (Y. Huang et al., J. Cereb. Blood Flow Metab. 22:1377-98 (2002)), but it is extremely doubtful that this method can image the branched, tortuous, and disorganized growth that occurs after spinal cord injury in response to AA-NgR(310)ecto-Fc treatment (X. Wang et al., Ann. Neurol. 60:540-49 (2006); S. Li et al., J. Neurosci. 24:10511-20 (2004); J. K. Lee et al., J. Neurosci. 24:6209-17 (2004); W. B. Cafferty et al., Neuron 54:195-99 (2007); L. Dimou et al., J. Neurosci. 26:5591-603 (2006); J. E. Kim et al., Neuron 44:439-51 (2004); J. E. Kim et al., Neuron 38:187-99 (2003); T. GrandPre et al., Nature 403:439-44 (2000)).

For visualizing raphespinal axon growth in the caudal spinal cord, a presynpatic marker of this axonal subset is required. PET ligands for serotonin reuptake sites are available, and [$^{11}$C]AFM shows highly selective binding to serotonin transporters (5HTT) in vivo (Y. Huang et al., J. Cereb. Blood Flow Metab. 22:1377-98 (2002); Y. Huang et al., Nucl. Med. Biol. 31:543-56 (2004)). To verify the feasibility of such a marker in spinal contusion, 5HTT-immunoreactive fibers were assessed histologically. Adjacent section were processed for anti-serotonin reuptake site immunohistochemistry and measured as for 5HT in FIGS. 2E and 2F. An increase in 5HTT fiber length in the caudal spinal cord of AA-NgR (310)ecto-Fc treated rats was very similar to that documented for 5HT itself (FIGS. 2G and 2H). Therefore, PET images were obtained from the spinal cord of anesthetized rats.

Figures 2I, 2J, 2K, 2L, 2M, 2N, 2O:
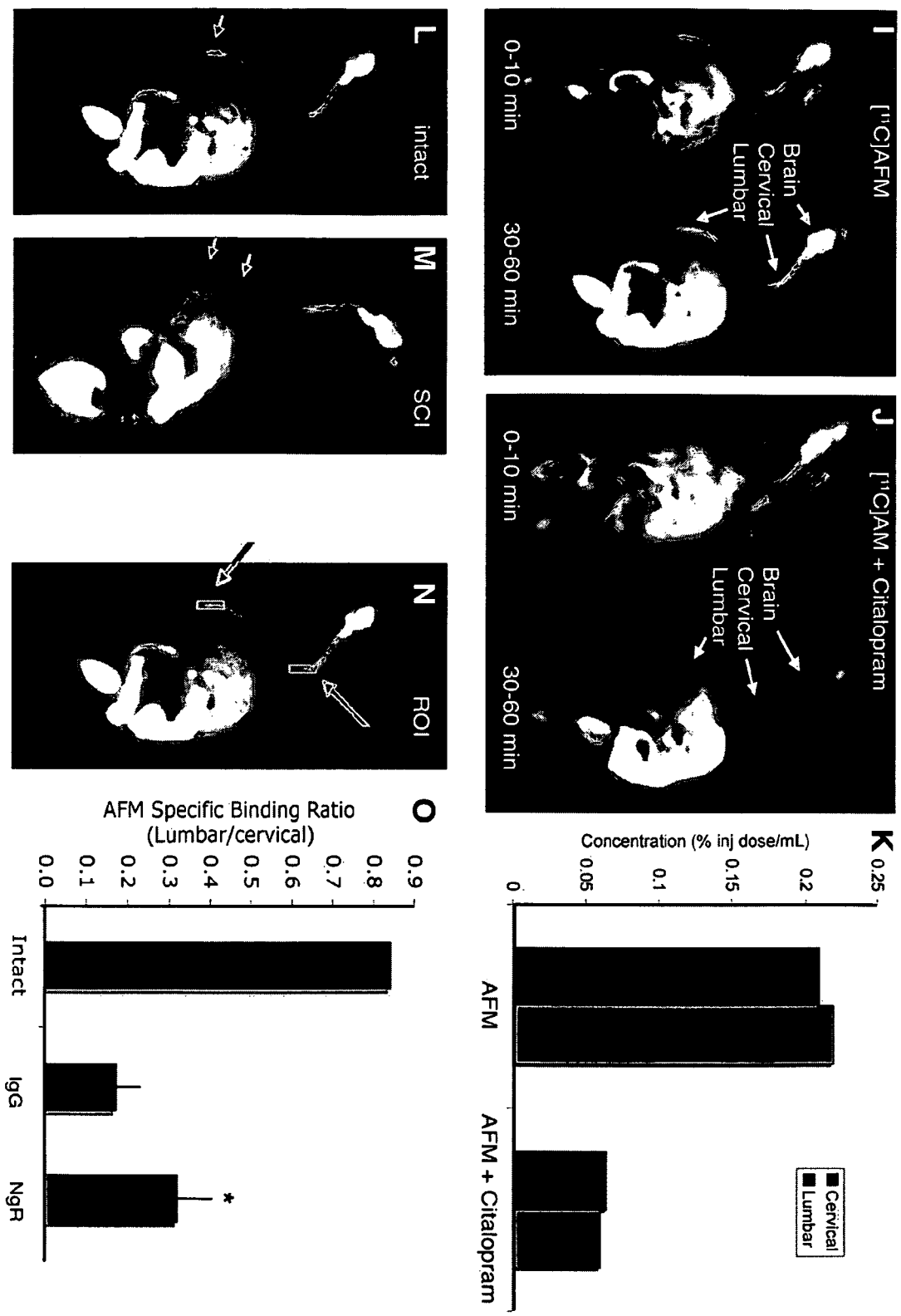
FIGS. 2I and 2J are PET images from anesthetized rats. [$^{11}$C]AFM radioactivity was visualized at the indicated times after an intravenous injection of the tracer (injected radioactivity 0.4 mCi, specific activity 8.4 mCi/nmol) with or without the co-injection of unlabeled competitive ligand, citalopram (2 mg/kg, i.v.). The initial distribution of the tracer is broad with or without citalopram at 0-10 min. Specific uptake of [$^{11}$C]AFM at 30-60 min in the brain, cervical spinal cord, and lumbar spinal cord is blocked by citalopram.
FIG. 2K is a graph depicting the concentration of tracer in the cervical and lumbar spinal cord. The concentration of the [$^{11}$C]AFM tracer in the cervical and lumbar enlargement of the spinal cord was quantitated as a percentage of the injected dose with or without citalopram.
FIGS. 2L and 2M are PET images from anesthetized rats with an intact spinal cord and a midthoracic transection. A rat with an intact spinal cord was imaged with [$^{11}$C]AFM and compared to a rat with a midthoracic transection one week earlier. Uptake at 30-60 minute is illustrated. The site of the lesion is indicated by the green arrow, and the reduced uptake in the lumbar cord of the injured rat is indicated by the red arrow.
FIG. 2N is a PET image from an anesthetized rat with chronic spinal cord contusion. For quantitation of [$^{11}$C]AFM uptake in the spinal cord of chronic spinal contusion rats, two regions of interest were selected as illustrated by the boxes in this intact rat image.
FIG. 2O is a graph depicting the [$^{11}$C]AFM specific binding ratio of lumbar to cervical uptake. The ratio of lumbar to cervical [$^{11}$C]AFM uptake at 30-60 minute post-tracer injection was determined in rats completing 3 months of therapy. The data are mean±sem for n=11-13 per group, and the increase in the NgR group in the distal cord is significant, $P<0.05$, Student's one-tailed t-test, *.

[$^{11}$C]AFM radioactivity was visualized at the indicated times after an intravenous injection of the tracer (injected radioactivity 0.4 mCi, specific activity 8.4 mCi/nmol) with or without the co-injection of unlabeled competitive 5HTT ligand, citalopram (2 mg/kb, i.v.). The initial distribution of the tracer is broad with or without citalopram at 0-10 min (FIG. 2I). The radioligand [$^{11}$C]AFM exhibited strong uptake in the brain and spinal cord at 30-60 minutes post-injection (FIG. 2I). More than 70% of this uptake was displaced by unlabelled citalopram (FIGS. 2J and 2K). The concentration of the [$^{11}$C]AFM tracer in the cervical and lumbar enlargement of the spinal cord was quantitated as a percentage of the injected dose with or without citalopram.

A rat with an intact spinal cord was imaged with [$^{11}$C]AFM and compared to a rat with midthoracic transaction one week earlier. Uptake at 30-60 is illustrated in FIGS. 2L and 2M. The site of the lesion is indicated by the green arrow, and the reduced uptake in the lumbar cord of the injured rat is indicated by the red arrow (FIGS. 2L and 2M). In rats with thoracic spinal injury, the cervical [$^{11}$C]AFM signal was similar to that in uninjured animals but the signal in the lumbar enlargement was reduced dramatically (FIGS. 2L and 2M), matching the immunohistological results with either anti-5HT or anti-5HTT.

For quantitation of [$^{11}$C]AFM uptake in the spinal cord of chronic spinal contusion rats, two regions of interest were selected as illustrated by the boxes in the intact rat image in FIG. 2N. The ratio of lumbar to cervical [$^{11}$C]AFM uptake at 30-60 minute post-tracer injection was determined in rats completing three months of therapy (FIG. 2O). In rats treated with AA-NgR(310)ecto-Fc for 3 months, the lumbar uptake as a proportion of the cervical uptake was two fold greater than in control rats (FIGS. 2N and 2O).

Thus, PET imaging of 5HTT with [$^{11}$C]AFM provided a non-invasive method to monitor axonal growth after treatment with axonal growth promoting compounds, such as AA-NgR(310)ecto-Fc.

Biological Deposits

Hybridomas HB 7E11 (ATCC® accession No. PTA-4587), HB 1H2 (ATCC® accession No. PTA-4584), HB 3G5 (ATCC® accession No. PTA-4586), HB 5B10 (ATCC® accession No. PTA-4588) and HB 2F7 (ATCC® accession No. PTA-4585) were deposited with the American Type Culture Collection ("ATCC®"), 10801 University Boulevard, Manassas, Va. 20110-2209, USA, on Aug. 9, 2002.

As those skilled in the art will appreciate, numerous changes and modifications may be made to the preferred embodiments of the invention without departing from the spirit of the invention. It is intended that all such variations fall within the scope of the invention.

---

It is claimed that:

1. A method of treating chronic spinal cord injury in a mammal in need thereof, comprising administering to the mammal a therapeutically effective amount of a Nogo-receptor antagonist, wherein treatment with said Nogo-receptor antagonist is initiated about twelve weeks after the spinal cord injury and wherein the administering is by chronic infusion or implantation of a controlled-release system.

2. The method of claim 1, wherein said Nogo-receptor antagonist stimulates axonal growth.

3. The method of claim 1, wherein said chronic spinal cord injury is a spinal contusion.

4. The method of claim 1, wherein said Nogo-receptor antagonist is administered directly into the central nervous system, intracerebroventricularly, or intrathecally.

5. The method of claim 1, wherein said Nogo-receptor antagonist is administered parenterally, intraventricularly, or via an implanted reservoir.

6. The method of claim 1, wherein the therapeutically effective amount is from 0.001 mg/kg to 10 mg/kg of Nogo-receptor antagonist.

7. The method of claim 6, wherein said therapeutically effective amount is from 0.01 mg/kg to 1.0 mg/kg.

8. The method of claim 1, wherein said Nogo-receptor antagonist is a Nogo receptor-1 polypeptide.

9. The method of claim 8, wherein said Nogo receptor-1 polypeptide is a soluble Nogo receptor-1 polypeptide.

10. The method of claim 9, wherein said soluble Nogo receptor-1 polypeptide is 90% identical to a reference amino acid sequence selected from the group consisting of:
    (a) amino acids 26 to 310 of SEQ ID NO:10 or 11;
    (b) amino acids 26 to 344 of SEQ ID NO:10 or 11;
    (c) amino acids 26 to 445 of SEQ ID NO:10 or 11;
    (d) amino acids 26 to 309 of SEQ ID NO:10 or 11;
    (e) amino acids 27 to 310 of SEQ ID NO:10 or 11;
    (f) amino acids 28 to 344 of SEQ ID NO:10 or 11;
    (g) amino acids 29 to 445 of SEQ ID NO:10 or 11;
    (h) amino acids 30 to 309 of SEQ ID NO:10 or 11;
    (i) amino acids 1 to 310 of SEQ ID NO:10 or 11;
    (j) amino acids 1 to 344 of SEQ ID NO:10 or 11;
    (k) amino acids 1 to 445 of SEQ ID NO:10 or 11;
    (l) amino acids 1 to 309 of SEQ ID NO:10 or 11; and
    (n) a combination of one or more of said reference amino acid sequences.

11. The method of claim 10, wherein said soluble Nogo receptor-1 polypeptide is selected from the group consisting of:
    (a) amino acids 26 to 310 of SEQ ID NO:10 or 11;
    (b) amino acids 26 to 344 of SEQ ID NO:10 or 11;
    (c) amino acids 26 to 445 of SEQ ID NO:10 or 11;
    (d) amino acids 26 to 309 of SEQ ID NO:10 or 11;
    (e) amino acids 27 to 310 of SEQ ID NO:10 or 11;
    (f) amino acids 27 to 344 of SEQ ID NO:10 or 11;
    (g) amino acids 27 to 445 of SEQ ID NO:10 or 11;
    (h) amino acids 27 to 309 of SEQ ID NO:10 or 11;
    (i) amino acids 1 to 310 of SEQ ID NO:10 or 11;
    (j) amino acids 1 to 344 of SEQ ID NO:10 or 11;
    (k) amino acids 1 to 445 of SEQ ID NO:10 or 11;
    (l) amino acids 1 to 309 of SEQ ID NO:10 or 11; and
    (n) a combination of one or more of said reference amino acid sequences.

12. The method of claim 8, wherein said Nogo receptor-1 polypeptide further comprises a non-NgR1 moiety.

13. The method claim 12, wherein said non-NgR1 moiety is a heterologous polypeptide fused to said Nogo receptor-1 polypeptide.

14. The method of claim 13, wherein said heterologous polypeptide is selected from the group consisting of:
    (a) serum albumin;
    (b) an Fc region;
    (c) a signal peptide;
    (d) a polypeptide tag; and
    (e) a combination of two or more of said heterologous polypeptides.

15. The method of claim 14, wherein said Fc region is selected from the group consisting of: an IgA Fc region; an IgD Fc region; an IgG Fc region, an IgE Fc region; and an IgM Fc region.

16. The method of claim 15, wherein said Fc region is an IgG Fc region.

17. The method of claim 16, further comprising a peptide linker situated between the Nogo receptor-1 polypeptide and said IgG Fc region.

18. The method of claim 17, wherein said peptide linker comprises SEQ ID NO:2 $(G_4S)_2$.

19. The method of claim 14, wherein said polypeptide tag is selected from the group consisting of: FLAG tag; Strep tag; poly-histidine tag; VSV-G tag; influenza virus hemagglutinin (HA) tag; and c-Myc tag.

20. The method of claim 12, wherein said non-NgR1 moiety is a polymer conjugated to said Nogo receptor-1 polypeptide.

21. The method of claim 20, wherein said polymer is selected from the group consisting of a polyalkylene glycol, a sugar polymer, and a polypeptide.

22. The method of claim 20, wherein said Nogo receptor-1 polypeptide is conjugated to 1, 2, 3, or 4 polymers.

23. The method of claim 22, wherein the total molecular weight of the polymers is from 5,000 Da to 100,000 Da.

24. The method of claim 8, wherein said Nogo receptor-1 polypeptide is a cyclic polypeptide.

25. The method of claim 24, wherein said cyclic polypeptide further comprises a first molecule linked at the N-terminus and a second molecule linked at the C-terminus; wherein said first molecule and said second molecule are joined to each other to form said cyclic molecule.

26. The method of claim 25, wherein said first and second molecules are selected from the group consisting of: a biotin molecule, a cysteine residue, and an acetylated cysteine residue.

* * * * *

UNITED STATES PATENT AND TRADEMARK OFFICE
CERTIFICATE OF CORRECTION

| | |
|---|---|
| PATENT NO. | : 8,992,918 B2 |
| APPLICATION NO. | : 12/922370 |
| DATED | : March 31, 2015 |
| INVENTOR(S) | : Stephen M. Strittmatter |

It is certified that error appears in the above-identified patent and that said Letters Patent is hereby corrected as shown below:

In the specification, column 1, line 13, after the section entitled "Cross-Reference to Related Applications" but before the section entitled "Reference to a Sequence Listing" please insert the following:

--U.S. GOVERNMENT SUPPORT

This invention was made with government support under NS042304 awarded by National Institutes of Health. The government has certain rights in the invention.--

Signed and Sealed this
Seventh Day of June, 2016

Michelle K. Lee
*Director of the United States Patent and Trademark Office*